US012753206B2

(12) United States Patent
Sakamoto et al.

(10) Patent No.: US 12,753,206 B2
(45) Date of Patent: Oct. 6, 2026

(54) VIPR2 ANTAGONIST PEPTIDE

(71) Applicant: ICHIMARU PHARCOS CO., LTD., Gifu (JP)

(72) Inventors: Kotaro Sakamoto, Gifu (JP); Yukio Ago, Hiroshima (JP)

(73) Assignee: ICHIMARU PHARCOS CO., LTD., Gifu (JP)

( * ) Notice: Subject to any disclaimer, the term of this patent is extended or adjusted under 35 U.S.C. 154(b) by 776 days.

(21) Appl. No.: 17/995,097

(22) PCT Filed: Mar. 19, 2021

(86) PCT No.: PCT/JP2021/011316

§ 371 (c)(1),
(2) Date: Sep. 29, 2022

(87) PCT Pub. No.: WO2021/200529

PCT Pub. Date: Oct. 7, 2021

(65) Prior Publication Data

US 2023/0174582 A1 Jun. 8, 2023

(30) Foreign Application Priority Data

Mar. 30, 2020 (JP) ................................ 2020-059721

(51) Int. Cl.

*C07K 7/64* (2006.01)
*A61K 38/00* (2006.01)
*A61K 47/54* (2017.01)
*A61P 25/28* (2006.01)

(52) U.S. Cl.

CPC .............. *C07K 7/64* (2013.01); *A61K 47/545* (2017.08); *A61P 25/28* (2018.01); *A61K 38/00* (2013.01)

(58) Field of Classification Search

None
See application file for complete search history.

(56) References Cited

U.S. PATENT DOCUMENTS

| | | | |
|---|---|---|---|
| 5,811,392 | A | 9/1998 | Gilon et al. |
| 2009/0263320 | A1 | 10/2009 | Cuthbertson |

FOREIGN PATENT DOCUMENTS

| | | | |
|---|---|---|---|
| JP | H10504802 A | 5/1998 | |
| JP | 2008510679 A | 4/2008 | |
| WO | 9533765 A1 | 12/1995 | |
| WO | 2005123767 A1 | 12/2005 | |

OTHER PUBLICATIONS

Sakamoto et al. (Biochem Biophys Res Commun. Sep. 10, 2018;503(3):1973-1979) (Year: 2018).*

Cleveland Clinic (downloaded from URL:<Neurodegenerative Diseases: What They Are & Types (clevelandclinic.org)>) (Year: 2024).*

David P. Fairlie et al., "Stapling Peptides Using Cysteine Crosslinking", Peptide science, May 14, 2016, vol. 106, No. 6, Wiley Online Library, p. 843-p. 852, 10pp.

David Vaudry et al., "Pituitary Adenylate Cyclase-Activating Polypeptide and Its Receptors: 20 Years after the Discovery", The American Society for Pharmacology and Experimental Therapeutics, 2009, vol. 61, No. 3, p. 283-p. 357, 76pp.

Jian-Ming Li et al., "Modulation of Immune Checkpoints and Graft-versus-Leukemia in Allogeneic Transplants by Vasoactive Intestinal Peptide", HHS Public Access Author manuscript, vol. 76, No. 23, Dec. 1, 2016, 27pp.

Kotaro Sakamoto et al., "Discovery of artificial VIPR2-antagonist peptides possessing receptor- and ligand-selectivity", Biochemical and Biophysical Research Communications, Aug. 1, 2018, vol. 503, p. 1973-p. 1979, Elsevier Inc., 7pp.

Sandrine Passemard et al., "VIP-induced Neuroprotection of the Developing Brain", Current Pharmaceutical Design, 2011, vol. 17, No. 10, p. 1036-p. 1039, Bentham Science Publishers Ltd., 4pp.

Shiyu Chen et al., "Dithiol amino acids can structurally shape and enhance the ligand-binding properties of polypeptides", nature chemistry, Aug. 31, 2014, vol. 6, No. 11, p. 1009-p. 1016, Macmillan Publishes Limited., 8pp.

Terry W. Moody et al. "Neuropeptides as Autocrine Growth Factors in Cancer Cells", Current Pharmaceutical Design, 2003, vol. 9, No. 6, p. 495-p. 509, Bentham Science Publishers Ltd., 15pp.

Vladimir Vacic et al., "Duplications of the neuropeptide receptor gene VIPR2 confer significant risk for schizophrenia", Research Letter, Mar. 24, 2011, vol. 471, p. 499-p. 503, Macmillan Publishers Limited, 6pp.

Xinli Tian et al., "Dosage sensitivity intolerance of VIPR2 microduplication is disease causative to manifest schizophrenia-like phenotypes in a novel BAC transgenic mouse model", Molecular Psychiatry, Aug. 23, 2019, Springer Nature Limited, 18pp.

Yu Heng Lau et al., "Peptide stapling techniques based on different macrocyclisation chemistries", The Royal Society of Chemistry, 2015, vol. 44, No. 91, p. 91-p. 102, 12pp.

(Continued)

*Primary Examiner* — Sergio Coffa
(74) *Attorney, Agent, or Firm* — HAUPTMAN HAM, LLP

(57) ABSTRACT

A VIPR2 antagonist peptide includes a cyclic peptide comprising an amino acid sequence represented by formula (17): c[$X^1$-Pro-$X^3$-$Tyr^4$-$Leu^5$-$Pro^6$-c($X^7$-$X^8$-$Leu^9$-$Cys^{10}$]-$X^{11}$)-$X^{12}$-$X^{13}$ (17), wherein $X^1$ denotes cysteine, Mpa (3-mercaptopropionic acid), or D-cysteine; $X^3$ denotes N-methylglycine, N-methylalanine, 2-azetidine-2-carboxylic acid, proline, hydroxyproline, 3,4-dehydroprolone, pipecolic acid, serine, or lysine; $X^8$ denotes tyrosine, proline, or arginine; $X^7$ and $X^{11}$ denotes any combination of lysine and aspartic acid, ornithine and glutamic acid, aspartic acid and lysine, glutamic acid and ornithine, lysine and glutamic acid, or glutamic acid and lysine; $X^{12}$ and $X^{13}$, each independently denotes leucine, isoleucine, or norleucine; $X^1$ and $Cys^{10}$ form a disulfide bond between their side chains, and $X^7$ and $X^{11}$ form an amide bond between their side chains, thereby forming two cyclic structures in a molecule of the peptide of formula (17); and an N-terminal amino group and a C-terminal carboxyl group may be modified.

7 Claims, 8 Drawing Sheets

Specification includes a Sequence Listing.

(56) References Cited

OTHER PUBLICATIONS

Yukio Ago et al., "Reductions in synaptic proteins and selective alteration of prepulse inhibition in male C57BL/6 mice after post-natal administration of a VIP receptor (VIPR2) agonist", Psychopharmacology, vol. 232, Jan. 11, 2015, p. 2181-p. 2189, Springer, 10pp.
Yuta Hara et al., "Improvement by Methylphenidate and Atomoxetine of Social Interaction Deficits and Recognition Memory Impairment in a Mouse Model of Valproic Acid-Induced Autism", Autism research, 2016, No. 9, p. 926-p. 939, 14pp.
International Search Report in PCT/JP2021/011316, mailed Jun. 1, 2021. 6pp.
Written Opinion in PCT/JP2021/011316, mailed Jun. 1, 2021. 7pp.

* cited by examiner

Seq-1 Seq-2 Seq-3 Seq-4 Seq-5 Seq-6 Seq-7 Seq-8 Seq-9 Seq-10

SEQUENCE LISTING

```
<160> NUMBER OF SEQ ID NOS: 11

<210> SEQ ID NO 1
<211> LENGTH: 13
<212> TYPE: PRT
<213> ORGANISM: Artificial Sequence
<220> FEATURE:
<223> OTHER INFORMATION: VIPR2 antagonistic bicyclic peptide 1
<220> FEATURE:
<221> NAME/KEY: MOD_RES
<222> LOCATION: (1)..(1)
<223> OTHER INFORMATION: 3-mercaptopropanoic acid (Mpa)
<220> FEATURE:
<221> NAME/KEY: DISULFID
<222> LOCATION: (1)..(10)
<223> OTHER INFORMATION: S-S(1-10)
<220> FEATURE:
<221> NAME/KEY: MISC_FEATURE
<222> LOCATION: (7)..(11)
<223> OTHER INFORMATION: Cyclization by amide linkage (7-11)
<220> FEATURE:
<221> NAME/KEY: MOD_RES
<222> LOCATION: (13)..(13)
<223> OTHER INFORMATION: AMIDATION

<400> SEQUENCE: 1

Xaa Pro Pro Tyr Leu Pro Lys Tyr Leu Cys Asp Leu Ile
1               5                   10


<210> SEQ ID NO 2
<211> LENGTH: 11
<212> TYPE: PRT
<213> ORGANISM: Artificial Sequence
<220> FEATURE:
<223> OTHER INFORMATION: VIPR2 antagonistic bicyclic peptide 2
<220> FEATURE:
<221> NAME/KEY: MOD_RES
<222> LOCATION: (1)..(1)
<223> OTHER INFORMATION: 3-mercaptopropanoic acid (Mpa)
<220> FEATURE:
<221> NAME/KEY: THIOETH
<222> LOCATION: (1)..(8)
<223> OTHER INFORMATION: Cyclization (1-8) by the reaction with
      1,4-diiodobutane (DIBut)
<220> FEATURE:
<221> NAME/KEY: MOD_RES
<222> LOCATION: (2)..(2)
<223> OTHER INFORMATION: N-methyl tyrosine (NmeTyr)
<220> FEATURE:
<221> NAME/KEY: MISC_FEATURE
<222> LOCATION: (5)..(9)
<223> OTHER INFORMATION: Cyclization by amide linkage (5-9)
<220> FEATURE:
<221> NAME/KEY: MOD_RES
<222> LOCATION: (11)..(11)
<223> OTHER INFORMATION: AMIDATION

<400> SEQUENCE: 2

Xaa Tyr Leu Pro Lys Tyr Leu Cys Asp Leu Ile
1               5                   10


<210> SEQ ID NO 3
<211> LENGTH: 11
<212> TYPE: PRT
<213> ORGANISM: Artificial Sequence
<220> FEATURE:
```

```
<223> OTHER INFORMATION: VIPR2 antagonistic bicyclic peptide 3
<220> FEATURE:
<221> NAME/KEY: MOD_RES
<222> LOCATION: (1)..(1)
<223> OTHER INFORMATION: 3-mercaptopropanoic acid (Mpa)
<220> FEATURE:
<221> NAME/KEY: THIOETH
<222> LOCATION: (1)..(8)
<223> OTHER INFORMATION: Cyclization (1-8) by the reaction with
      1,5-diiodopentane (DIPen)
<220> FEATURE:
<221> NAME/KEY: MOD_RES
<222> LOCATION: (2)..(2)
<223> OTHER INFORMATION: N-methyl tyrosine (NmeTyr)
<220> FEATURE:
<221> NAME/KEY: MISC_FEATURE
<222> LOCATION: (5)..(9)
<223> OTHER INFORMATION: Cyclization by amide linkage (5-9)
<220> FEATURE:
<221> NAME/KEY: MOD_RES
<222> LOCATION: (11)..(11)
<223> OTHER INFORMATION: AMIDATION

<400> SEQUENCE: 3

Xaa Tyr Leu Pro Lys Tyr Leu Cys Asp Leu Ile
1               5                   10


<210> SEQ ID NO 4
<211> LENGTH: 11
<212> TYPE: PRT
<213> ORGANISM: Artificial Sequence
<220> FEATURE:
<223> OTHER INFORMATION: VIPR2 antagonistic bicyclic peptide 4
<220> FEATURE:
<221> NAME/KEY: MOD_RES
<222> LOCATION: (1)..(1)
<223> OTHER INFORMATION: 3-mercaptopropanoic acid (Mpa)
<220> FEATURE:
<221> NAME/KEY: THIOETH
<222> LOCATION: (1)..(8)
<223> OTHER INFORMATION: Cyclization (1-8) by the reaction with
      1,6-diiodohexane (DIHex)
<220> FEATURE:
<221> NAME/KEY: MOD_RES
<222> LOCATION: (2)..(2)
<223> OTHER INFORMATION: N-methyl tyrosine (NmeTyr)
<220> FEATURE:
<221> NAME/KEY: MISC_FEATURE
<222> LOCATION: (5)..(9)
<223> OTHER INFORMATION: Cyclization by amide linkage (5-9)
<220> FEATURE:
<221> NAME/KEY: MOD_RES
<222> LOCATION: (11)..(11)
<223> OTHER INFORMATION: AMIDATION

<400> SEQUENCE: 4

Xaa Tyr Leu Pro Lys Tyr Leu Cys Asp Leu Ile
1               5                   10


<210> SEQ ID NO 5
<211> LENGTH: 11
<212> TYPE: PRT
<213> ORGANISM: Artificial Sequence
<220> FEATURE:
<223> OTHER INFORMATION: VIPR2 antagonistic bicyclic peptide 5
<220> FEATURE:
<221> NAME/KEY: MOD_RES
<222> LOCATION: (1)..(1)
<223> OTHER INFORMATION: 3-mercaptopropanoic acid (Mpa)
<220> FEATURE:
<221> NAME/KEY: THIOETH
<222> LOCATION: (1)..(8)
<223> OTHER INFORMATION: Cyclization (1-8) by the reaction with
      1,2-bis(bromomethyl)benzene (DBoXy (1-8)
<220> FEATURE:
```

<221> NAME/KEY: MOD_RES
<222> LOCATION: (2)..(2)
<223> OTHER INFORMATION: N-methyl tyrosine (NmeTyr)
<220> FEATURE:
<221> NAME/KEY: MISC_FEATURE
<222> LOCATION: (5)..(9)
<223> OTHER INFORMATION: Cyclization by amide linkage (5--9)
<220> FEATURE:
<221> NAME/KEY: MOD_RES
<222> LOCATION: (11)..(11)
<223> OTHER INFORMATION: AMIDATION

<400> SEQUENCE: 5

Xaa Tyr Leu Pro Lys Tyr Leu Cys Asp Leu Ile
1 5 10

<210> SEQ ID NO 6
<211> LENGTH: 11
<212> TYPE: PRT
<213> ORGANISM: Artificial Sequence
<220> FEATURE:
<223> OTHER INFORMATION: VIPR2 antagonistic bicyclic peptide 6
<220> FEATURE:
<221> NAME/KEY: MOD_RES
<222> LOCATION: (1)..(1)
<223> OTHER INFORMATION: 3-mercaptopropanoic acid (Mpa)
<220> FEATURE:
<221> NAME/KEY: THIOETH
<222> LOCATION: (1)..(8)
<223> OTHER INFORMATION: Cyclization (1-8) by the reaction with 1,3-bis(bromomethyl)benzene (DBmXy )
<220> FEATURE:
<221> NAME/KEY: MOD_RES
<222> LOCATION: (2)..(2)
<223> OTHER INFORMATION: N-methyl tyrosine (NmeTyr)
<220> FEATURE:
<221> NAME/KEY: MISC_FEATURE
<222> LOCATION: (5)..(9)
<223> OTHER INFORMATION: Cyclization by amide linkage (5-9)
<220> FEATURE:
<221> NAME/KEY: MOD_RES
<222> LOCATION: (11)..(11)
<223> OTHER INFORMATION: AMIDATION

<400> SEQUENCE: 6

Xaa Tyr Leu Pro Lys Tyr Leu Cys Asp Leu Ile
1 5 10

<210> SEQ ID NO 7
<211> LENGTH: 11
<212> TYPE: PRT
<213> ORGANISM: Artificial Sequence
<220> FEATURE:
<223> OTHER INFORMATION: VIPR2 antagonistic bicyclic peptide 7
<220> FEATURE:
<221> NAME/KEY: MOD_RES
<222> LOCATION: (1)..(1)
<223> OTHER INFORMATION: 3-mercaptopropanoic acid (Mpa)
<220> FEATURE:
<221> NAME/KEY: THIOETH
<222> LOCATION: (1)..(8)
<223> OTHER INFORMATION: Cyclization (1-8) by the reaction with 1,4-bis(bromomethyl)benzene (DBpXy)
<220> FEATURE:
<221> NAME/KEY: MOD_RES
<222> LOCATION: (2)..(2)
<223> OTHER INFORMATION: N-methyl tyrosine (NmeTyr)
<220> FEATURE:
<221> NAME/KEY: MISC_FEATURE
<222> LOCATION: (5)..(9)
<223> OTHER INFORMATION: Cyclization by amide linkage (5-9)
<220> FEATURE:
<221> NAME/KEY: MOD_RES
<222> LOCATION: (11)..(11)
<223> OTHER INFORMATION: AMIDATION

<400> SEQUENCE: 7

Xaa Tyr Leu Pro Lys Tyr Leu Cys Asp Leu Ile
1 5 10

<210> SEQ ID NO 8
<211> LENGTH: 11
<212> TYPE: PRT
<213> ORGANISM: Artificial Sequence
<220> FEATURE:
<223> OTHER INFORMATION: VIPR2 antagonistic bicyclic peptide 8
<220> FEATURE:
<221> NAME/KEY: MOD_RES
<222> LOCATION: (1)..(1)
<223> OTHER INFORMATION: 3-mercaptopropanoic acid (Mpa)
<220> FEATURE:
<221> NAME/KEY: MISC_FEATURE
<222> LOCATION: (1)..(5)
<223> OTHER INFORMATION: trifurcate linkage by TBMB (1-5-8)
<220> FEATURE:
<221> NAME/KEY: MOD_RES
<222> LOCATION: (2)..(2)
<223> OTHER INFORMATION: N-methyl tyrosine (NmeTyr)
<220> FEATURE:
<221> NAME/KEY: MOD_RES
<222> LOCATION: (4)..(4)
<223> OTHER INFORMATION: METHYLATION, (MeGly)
<220> FEATURE:
<221> NAME/KEY: MISC_FEATURE
<222> LOCATION: (5)..(8)
<223> OTHER INFORMATION: trifurcate linkage by TBMB (1-5-8)
<220> FEATURE:
<221> NAME/KEY: MOD_RES
<222> LOCATION: (11)..(11)
<223> OTHER INFORMATION: AMIDATION

<400> SEQUENCE: 8

Xaa Tyr Leu Gly Cys Tyr Leu Cys Ser Leu Ile
1 5 10

<210> SEQ ID NO 9
<211> LENGTH: 11
<212> TYPE: PRT
<213> ORGANISM: Artificial Sequence
<220> FEATURE:
<223> OTHER INFORMATION: VIPR2 antagonistic bicyclic peptide 9
<220> FEATURE:
<221> NAME/KEY: MOD_RES
<222> LOCATION: (1)..(1)
<223> OTHER INFORMATION: 3-mercaptopropanoic acid (Mpa)
<220> FEATURE:
<221> NAME/KEY: MISC_FEATURE
<222> LOCATION: (1)..(5)
<223> OTHER INFORMATION: trifurcate linkage by TBMB (1-5-8)
<220> FEATURE:
<221> NAME/KEY: MOD_RES
<222> LOCATION: (2)..(2)
<223> OTHER INFORMATION: N-methyl tyrosine (NmeTyr)
<220> FEATURE:
<221> NAME/KEY: MOD_RES
<222> LOCATION: (4)..(4)
<223> OTHER INFORMATION: METHYLATION, (MeGly)
<220> FEATURE:
<221> NAME/KEY: MISC_FEATURE
<222> LOCATION: (5)..(8)
<223> OTHER INFORMATION: trifurcate linkage by TBMB (1-5-8)
<220> FEATURE:
<221> NAME/KEY: MOD_RES
<222> LOCATION: (9)..(9)
<223> OTHER INFORMATION: (S)-2,3-Diaminopropanoic acid (Dap)
<220> FEATURE:
<221> NAME/KEY: MOD_RES
<222> LOCATION: (11)..(11)
<223> OTHER INFORMATION: AMIDATION -continued

<400> SEQUENCE: 9

Xaa Tyr Leu Gly Cys Tyr Leu Cys Xaa Leu Ile
1 5 10

<210> SEQ ID NO 10
<211> LENGTH: 13
<212> TYPE: PRT
<213> ORGANISM: Artificial Sequence
<220> FEATURE:
<223> OTHER INFORMATION: VIPR2 antagonistic bicyclic peptide 10
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(10)
<223> OTHER INFORMATION: S-S(1-10)
<220> FEATURE:
<221> NAME/KEY: MISC_FEATURE
<222> LOCATION: (7)..(11)
<223> OTHER INFORMATION: Cyclization by amide linkage (7-11)
<220> FEATURE:
<221> NAME/KEY: MOD_RES
<222> LOCATION: (13)..(13)
<223> OTHER INFORMATION: AMIDATION

<400> SEQUENCE: 10

Cys Pro Pro Tyr Leu Pro Lys Tyr Leu Cys Asp Leu Ile
1 5 10

<210> SEQ ID NO 11
<211> LENGTH: 16
<212> TYPE: PRT
<213> ORGANISM: Artificial Sequence
<220> FEATURE:
<223> OTHER INFORMATION: cyclic peptide VIpep-3
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(10)

<400> SEQUENCE: 11

Cys Pro Pro Tyr Leu Pro Arg Arg Leu Cys Thr Leu Leu Leu Arg Ser
1 5 10 15

VIPR2 ANTAGONIST PEPTIDE

CROSS REFERENCE

This application is a National Phase of International Application No. PCT/JP2021/011316 filed Mar. 19, 2021, which claims priority based on Japanese Patent Application No. 2020-059721 filed in Japan on Mar. 30, 2020, the entire contents of which are incorporated herein by reference in their entirety.

The sequence listing provided in the file entitled F-08_SequenceListing.txt, which is an ASCII text file that was created on Sep. 21, 2022, and which comprises 7,120 byes, is hereby incorporated by reference in its entirety.

TECHNICAL FIELD

Embodiments relate to peptides and the like that inhibit the activity of VIPR2, and more particularly to cyclic peptides and the like having a specific amino acid sequences and cyclic structures.

BACKGROUND ART

Vasoactive intestinal peptide receptor 2 (VIPR2), also known as VPAC2, is a class B G protein-coupled receptor (GPCR). It is expressed throughout the body, including central nervous systems and peripheral tissues such as sensory organs, digestive organs, and reproductive organs, and exhibits diverse physiological functions by interacting with its ligands, Vasoactive intestinal peptide (VIP) and Pituitary adenylate cyclase-activating polypeptide (PACAP). For example, VIP and PACAP signaling through VIPR2 and its subtype receptors, Vasoactive intestinal peptide receptor 1 (VIPR1 or VPAC1) and Pituitary adenylate cyclase-activating polypeptide type-1 receptor (PAC1), is known to have neuroprotective effects (Non-Patent Literature 1 and Non-Patent Literature 2). Interestingly, on the other hand, it has recently been reported that high expression or hyperactivation of VIPR2 may be involved in the development of schizophrenia and autism spectrum disorder (Non-Patent Literature 3, Non-Patent Literature 4, and Non-Patent Literature 5). It has also been reported that inhibition of VIP signaling inhibits cancer growth and stimulates immunity (Non-Patent Literature 6 and Non-Patent Literature 7).

In 2011, Vacic et al. reported that some schizophrenia patients and some patients with autism spectrum disorders have a duplication in the gene region encoding VIPR2, and their lymphocytes have increased VIPR2 mRNA expression levels and also reported that they were hypersensitive to VIP (see Non-Patent Literature 3). Also in 2015, Ago et al. reported that administration of a VIPR2-selective agonist, Ro25-1553 to artificially create a state of overactivation of VIPR2 in the postnatal mouse results in a reduction of cognitive functions of mature individuals of the mouse (Non-Patent Literature 4). Furthermore, in 2019, Tian et al. generated a transgenic mouse with a duplication in the gene region encoding VIPR2 and reported that the mouse exhibited symptoms of abnormal dopamine function, cognitive dysfunction, and social behavior (Non-Patent Literature 5). These findings strongly suggest that excessive signaling through VIPR2 is involved in the pathogenesis of psychiatric disorders such as schizophrenia and autism spectrum disorders.

Schizophrenia, which affects an estimated 24 million people worldwide, is a psychiatric disorder that causes positive symptoms (e.g., hallucinations and delusions), negative symptoms (e.g., decreased motivation), and cognitive dysfunction that not only reduces an individual's social functioning but also results in a high suicide rate. Although the heritability is as high as 80%, no specific disease-causing gene common to all patients has been identified, and the development of new drugs and treatment methods is desired. Autism spectrum disorders are said to affect about 1 to 2 per 1,000 people worldwide and cause impaired social and interpersonal communication skills. There are no clear prevention or treatment methods for the disorder, which is largely due to congenital factors.

As mentioned above, some schizophrenia patients and some autism spectrum disorder patients have been reported to overexpress VIPR2, suggesting that overexpression of VIPR2 may be involved in the pathogenesis of the disease. In other words, if genomic analysis identifies the presence of a duplication in the gene region encoding VIPR2, administration of VIPR2 inhibitors is expected to be effective as a means of preventing and/or treating the onset of schizophrenia and autism spectrum disorders.

In 2018, the inventor developed and reported a cyclic antagonist peptide VIpep-3: Ac-c(Cys-Pro-Pro-Tyr-Leu-Pro-Arg-Arg-Leu-Cys)-Thr-Leu-Leu-Leu-Arg-Ser-OH (SEQ ID No.11) that binds to a VIPR2 extracellular region of the recombinant protein and inhibits the signaling pathway of VIP and PACAP through VIPR2 in cellular studies (Non-Patent Literature 8).

CITATION LIST

Non-Patent Literature

[Non-Patent Literature 1] Vaudry D, Falluel-Morel A, Bourgault S, Basille M, Burel D, Wurtz O, Fournier A, Chow B K, Hashimoto H, Galas L, and Vaudry H. Pharmacol Rev. 2009, 61(3):283-357.

[Non-Patent Literature 2] Passemard S, Sokolowska P, Schwendimann L, and Gressens P. Curr Pharm Des. 2011, 17(10): 1036-1039.

[Non-Patent Literature 3] Vacic V, McCarthy S, Malhotra D, Murray F, Chou H H, Peoples A, Makarov V, Yoon S, Bhandari A, Corominas R, Iakoucheva L M, Krastoshevsky O, Krause V, Larach-Walters V, Welsh D K, Craig D, Kelsoe J R, Gershon E S, Leal S M, Dell Aquila M, Morris D W, Gill M, Corvin A, Insel P A, McClellan J, King M C, Karayiorgou M, Levy D L, DeLisi L E, and Sebat J. Nature. 2011, 471(7339):499-503.

[Non-Patent Literature 4] Ago Y, Condro M C, Tan Y V, Ghiani C A, Colwell C S, Cushman J D, Fanselow M S, Hashimoto H, and Waschek J A. Psychopharmacology (Berl). 2015,232 (12):2181-2189.

[Non-Patent Literature 5] Tian X, Richard A, EI-Saadi M W, Bhandari A, Bhandari A, Latimer B, Van Savage I, Holmes K, Klein R L, Dwyer D, Goeders N E, Yang X W, and Lu X H. Psychiatry 2019, doi: 10.1038/s41 380-019-0492-3.

[Non-Patent Literature 6] Moody T W, Chan D, Fahrenkrug J, and Jensen R T. Curr. Pharm Des. 2003, 9(6):49 5-509.

[Non-Patent Literature 7] Li J M, Petersen C T, Li J X, Panjwani R, Chandra D J, Giver C R, Blazar B R, and Waller E K. Cancer Res. 2016, 76(23):6802-6815.

[Non-Patent Literature 8] Sakamoto K, Koyama K, Koyama R, Kamada Y, Miwa M, and Tani A. Biochem Biophys Res Commun. 2018, 503:1973-1979.

[Non-Patent Literature 9] Fairlie D P and Dantas de Araujo. Biopolymers. 2016, 106(6): 843-852.

[Non-Patent Literature 10] Lau Y H, de Andrade P, Wu Y, and Spring D R. Chem Soc Rev. 2015, 44(1) 91-102.
[Non-Patent Literature 11] Chen S, Gopalakrishnan R, Schaer T, Marger F, Hovius R, Bertrand D, Pojer F, and Heinis C. Nat Chem 2014, 6(11) 1009-1016.
[Non-Patent Literature 12] Hara Y, Ago Y, Taruta A, Katashiba K, Hasebe S, Takano E, Onaka Y, Hashimoto H, Matsuda T, and Takuma K. Autism Res. 2016, 9(9) 926-939.

SUMMARY OF INVENTION

Technical Problem

The above VIpep-3 found by the inventor is a cyclic antagonist peptide that tightly binds to the extracellular domain of human VIPR2 and inhibits the VIP-VIPR2 signaling pathway. However, because VIpep-3 consists entirely of natural amino acids, there are concerns about its low resistance to protease degradation.

The embodiments were made in view of such problems and are intended to provide novel VIPR2 antagonist peptides suitable for use as pharmaceuticals, diagnostic agents, and/or research reagents.

Solution to Problem

In the course of conducting optimization studies of VIpep-3, the inventor discovered a group of novel VIPR2 antagonist peptides. To solve the above problem, the inventor investigated (1) substitution of the amino acid residues, (2) reduction of molecular weight by deletion of N-terminal and/or C-terminal amino acid residues, and (3) introduction of bicyclic structure. As a result, a novel group of sequences of VIPR2 antagonist peptides with protease degradation resistance and VIPR2 antagonist activity has been discovered and the embodiments have been completed.

An aspect of the embodiments include: [1] A cyclic peptide or a pharmaceutically acceptable salt of the peptide comprising an amino acid sequence represented by formula (1):

$$c[X^{N}\text{-}X^{4}\text{-}X^{5}\text{-}X^{6}\text{-}c(X^{7}\text{-}X^{8}\text{-}X^{9}\text{-}X^{10}]\text{—}X^{11})\text{-}X^{12}\text{-}X^{13}\text{-}X^{14}\text{-}X^{15}\text{-}X^{16} \quad (1)$$

or formula (2):

$$c[X^{N}\text{-}X^{4}\text{-}X^{5}\text{-}X^{6}\text{-}c(X^{7}\text{-}X^{8}\text{-}X^{9}\text{-}X^{10})]\text{—}X^{11}\text{-}X^{12}\text{-}X^{13}\text{-}X^{14}\text{-}X^{15}\text{-}X^{16} \quad (2)$$

Here, $X^N$ and $X^{10}$, and $X^7$ and $X^{11}$ in formula (1), and $X^N$, $X^7$ and $X^{10}$ in formula (2), independently of each other, covalently bind to form two cyclic structures in a molecule; each of the covalent bonds is any linkage between a main-chain and a side-chain, or between side-chains thereof, or may be an indirect covalent bond via a linker.

In formulae (1) and (2) above, $X^N$ denotes $X^1$-$X^2$-$X^3$; and $X^1$, $X^2$, $X^3$, $X^7$, $X^{10}$ and $X^{11}$ each independently denotes, in a case where involving cyclization of the molecule, an amino acid residue having an amino group, a carboxyl group, a thiol group, an allyl group, an alkynyl group, an azido group or a halogen atom, or a derivative thereof, or in a case of not involving cyclization of the molecule; $X^1$ and $X^2$ each independently denotes any amino acid residue or deletion, and $X^3$ and $X^{11}$ each independently denotes any amino acid residue. $X^5$, $X^9$, $X^{12}$, and $X^{13}$ each independently denotes an amino acid reside having a hydrocarbon group optionally containing a substituent, or a derivative thereof; $X^4$ denotes an amino acid reside having an aromatic carbocyclic group optionally containing a substituent, or a derivative thereof; $X^6$ and $X^8$ each independently denotes any amino acid residue; $X^{14}$, $X^{15}$ and $X^{16}$ each independently denotes any amino acid residue or deletion; and an N-terminal amino group and a C-terminal carboxyl group may be modified or deleted.

Preferred or other embodiments and the preferred examples of each of the amino acid residues of $X^1$ to $X^{16}$ in the above cyclic peptides are described in detail below, but the preferred embodiments are independent of each other, and the respective embodiments may be combined arbitrarily.

Effects of the Invention

The embodiments provide novel cyclic peptides useful for the use of VIPR2 antagonists as drugs, diagnostics, and/or research reagents.

DESCRIPTION OF EMBODIMENTS

Figure 1:
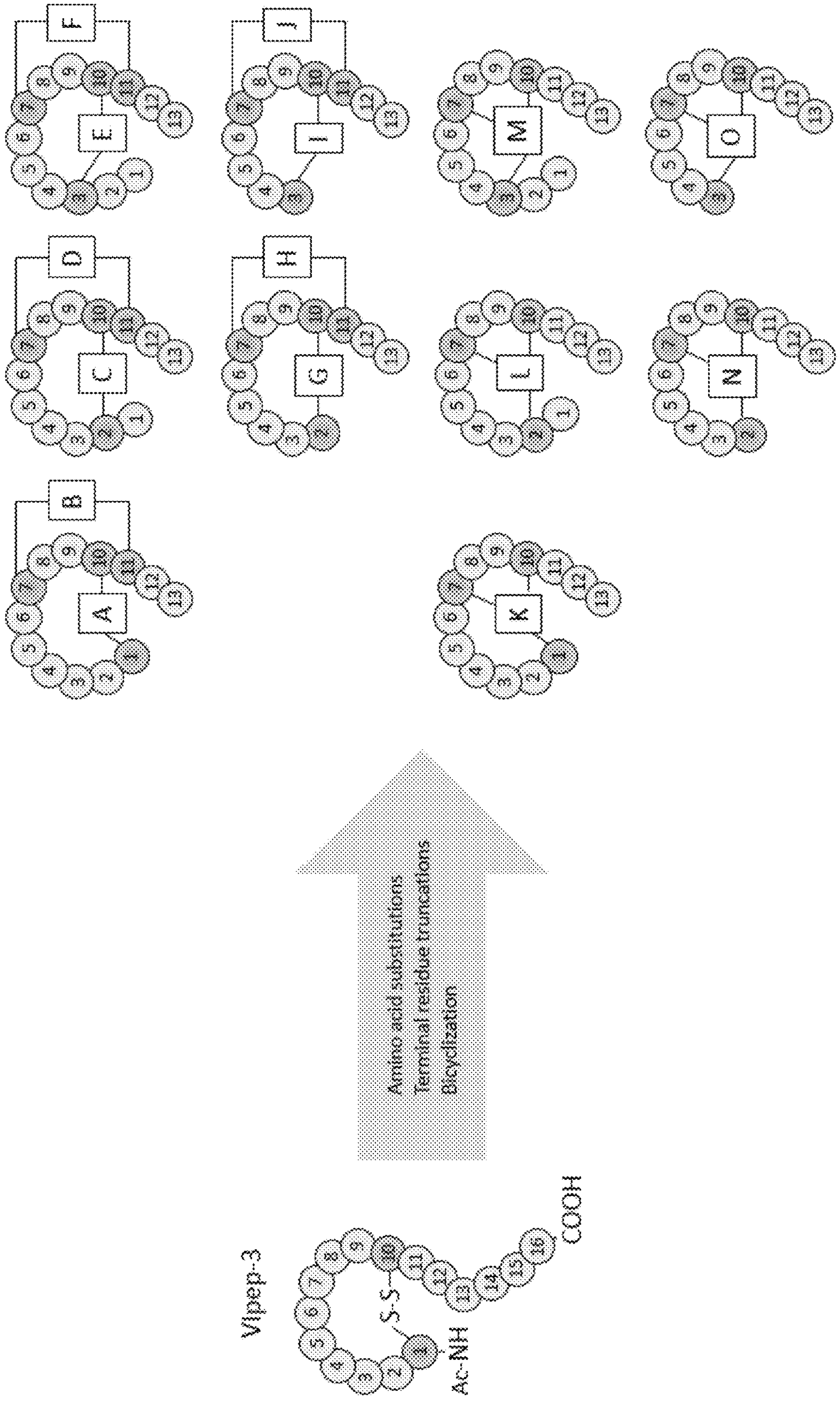
FIG. 1 shows the amino acid sequences involved in functions of VIpep-3 such as VIPR2 binding activity (pharmacophore) and cyclic structure constraint (S—S bond). The structures of the peptide of the embodiments, which is a modification of VIpep-3, are also outlined.

Next, suitable embodiments will be described with reference to the drawings. The embodiments described below are not intended to limit the claimed invention.

Definition

A peptide herein refers to two or more amino acids (for example, 2 to 20 amino acids) connected by an amide bond (peptide bond). In accordance with the conventional peptide notation, the left end is the N-terminal (amino terminal) and the right end is the C-terminal (carboxy terminal). The first carbon atom adjacent to the carbonyl group that forms the peptide bond is referred to as Cα carbon.

In the present specification, "any amino acid, or a derivative thereof" is used in its broadest sense and includes, in addition to natural amino acids, artificial amino acids with non-natural structures, chemically synthesized compounds with properties known in the industry to be characteristic of amino acids, as well as carboxylic acids with functional groups. Examples of unnatural amino acids include, but are not limited to, D-amino acids, α/α-disubstituted amino acids whose main chain structure differs from the natural type (e.g. α-methylated amino acids such as 2-aminoisobutyric acid), N-alkyl-amino acids (such as N-methylated amino acids), N-substituted glycine (peptoid), amino acids with elongated main chains (β-homo amino acids and γ-homo amino acids), amino acids whose side chain structure differs from the natural type (such as cyclohexylalanine, allylglycine, 2-(2-pyridyl)-glycine, 3-(1H-benzoimidazol-2-yl)-alanine), amino acids with partially substituted side chains (such as norleucine, diaminopropanoic acid and 3-(2-pyridyl)-alanine), amino acids with an extra functional group on the side chain, amino acids with extra C, alkyl, or methyl groups on the side chain (such as homonorleucine and γ-methyl leucine), amino acids with halogen atoms (F, Cl, Br, I) in the side chain (such as 3-chloroalanine), carboxylic acids with halogen atoms (F, Cl, Br, I) in the side chain (such as 3-chloropropanoic acid), carboxylic acids with functional groups on the side chain (such as 3-butenoic acid), amino acids with an extra N or amino group on the side chain (such as β-azidoalanine and ornithine), amino acids with an extra 0 or methoxy group on the side chain (such as O-methyl-serine and O-methyl-threonine), amino acids with extra hydroxy groups in the side chain (such as 3-hydroxy-phenylalanine), amino acids with an extra carboxy group (—COOH) in the side chain (such as 3-carboxy-phenylalanine), amino acids with an extra S in the side chain (such as ethionine), amino acids in which the carboxylic acid functional group in the side chain is protected by an ester (such as aspartic acid-4-methyl ester), amino acids in which a thiol group (—S—) in the side chain is oxidized to a sulfinyl group (—S(═O)—) or a sulfonyl group (—S(═O)$_2$—) (such as methionine sulfoxide), and the like.

In the present specification, a hydrocarbon group which may have a substituent refers to, for example, $C_{1-10}$ alkyl groups such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl; $C_{2-10}$ alkenyl groups, such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl; $C_{2-10}$ alkynyl groups, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4-methyl-2-pentynyl; $C_{3-10}$ cycloalkyl groups, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, adamantly; $C_{3-10}$ cycloalkenyl groups such as cyclopropenyl, cyclobutenyl, cyclopentenyl, cyclohexenyl, cycloheptenyl, cyclooctenyl, and the like. An aromatic carbon ring group that may have a substituent refers to, for example, a phenyl group or a naphthyl group. An aromatic heterocyclic group that may have a substituent group means but are not limited to, for example, pyridyl, thienyl, furfuryl, pyrrolyl, imidazolyl, pyrazolyl, thiazolyl, isothiazolyl, oxazolyl, isoxazolyl, pyrazinyl, pyrimidinyl, pyridazinyl, 1,2,4-oxadiazolyl 1,2,4-oxadiazolyl, 1,3,4-oxadiazolyl, 1,2,4-thiadiazolyl, 1,3,4-thiadiazolyl, triazolyl, tetrazolyl, triazinyl, and other 5 or 6 membered monocyclic aromatic heterocyclic groups; and also a 8 or 14 membered fused polycyclic (preferably 2 or 3 ring) aromatic heterocyclic group, such as benzofuranyl, benzothienyl, benzimidazolyl, benzoxazolyl, benzoisoxazolyl, benzothiazolyl, benzoisothiazolyl, benzotriazolyl, imidazopyridinyl, thienopyridinyl, flopyridinyl, pyrrolopyridinyl, pyrazolopyridinyl, oxazolopyridinyl oxazolopyridinyl, thiazolopyridinyl, imidazopyrazinyl, imidazopyrimidinyl, thienopyrimidinyl, flopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, prinyl, isoquinolyl, quinolyl, phthalazinyl, naphthyridinyl, quinoxalinyl, quinazolinyl, cinolinyl, carbazolyl, β-carbolinyl, phenanthridinyl, acridinyl, phenazinyl, phenothiazinyl, phenoxazinyl, and the like.

As used herein, "VIPR2" refers to mammalian proteins such as mouse, rat, dog, monkey, and human.

In this specification, the phrase, "having VIPR2 antagonist activity" means that in in vitro studies, the peptides of the embodiments (1) inhibit the binding of the previously reported biotin-labeled form of the VIPR2 antagonist peptide, VIpep-3 to VIPR2 recombinant proteins, (2) inhibit the binding of the previously reported biotin-labeled form of the VIPR2 antagonist peptide, VIpep-3 to VIPR2-expressing cells, (3) bind to VIPR2 recombinant proteins in a concentration-dependent manner, (4) bind to VIPR2-expressing cells in a concentration-dependent manner, (5) inhibit the increase in calcium concentration in VIPR2-expressing cells when added prior to or co-added with VIP, (6) suppress the increase in cAMP concentration in VIPR2-expressing cells when added prior to or co-incubated with VIP, (7) inhibit the recruitment of β-arrestin in VIPR2-expressing cells when added prior to or co-added with VIP, and so on, and when any one of these effects is shown, referred to as "having VIPR2 antagonist activity". The presence or absence of VIPR2 antagonist activity can be confirmed according to methods known to those skilled in the art with reference to Non-Patent Literature 7, etc., but are not limited to these methods.

Cyclic Peptide

Figure 2:
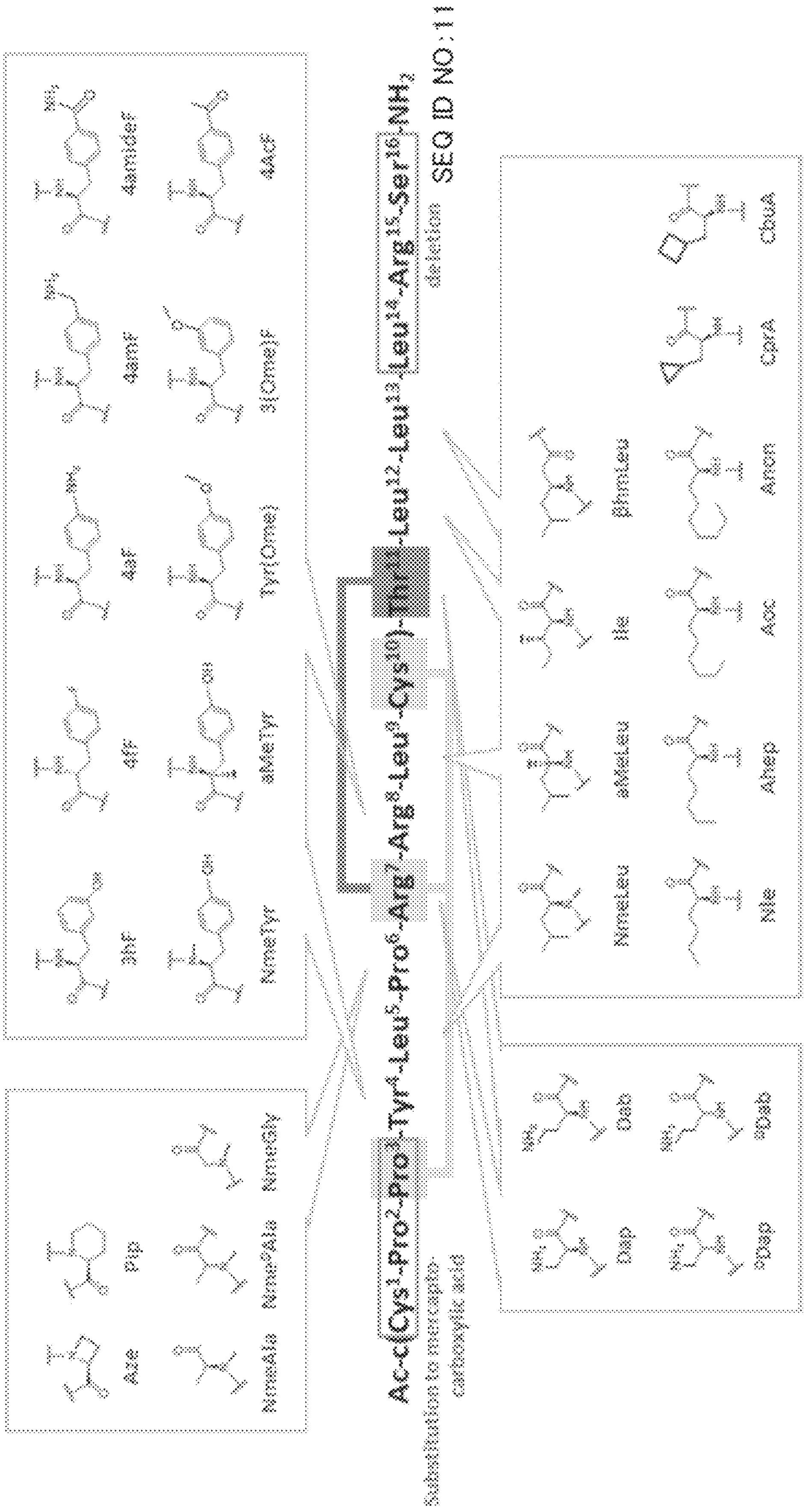
FIG. 2 shows examples of amino acid residues used in the amino acid substitution study at each amino acid position in VIpep-3 and the positions of amino acid residues for bicyclization study.

The structure of one embodiment of the cyclic peptide is illustrated in FIG. 1. FIG. 1 schematically shows features involved in VIPR2 binding activity (pharmacophore), and the structure involved in the function of the cyclic structure regulation (S—S bond), which was the basis for the cyclic peptide design, and relationship between VIpep-3 and the modified cyclic peptide of this embodiments. The first to 13th amino acid residues of VIpep-3 correspond to the first to 13th amino acid residues of the cyclic peptide of this embodiment, but the first amino acid, or the first and second amino acid residues may be deleted in the cyclic peptide of this embodiment. The cyclization between the first and tenth cysteine residues in VIpep-3 is more stabilized in this embodiment of cyclic peptide, as (1) two cyclic structures by bond A between the first and tenth amino acid residues and bond B between the seventh and eleventh amino acid residues; (2) two cyclic structures by bond C between the second and tenth amino acid residue and bond D between the seventh and eleventh amino acid residue, or two cyclic structures with bond G between the second and tenth amino acid residue and bond H between the seventh and eleventh amino acid residue; (3) two cyclic structures by bond E between the third and tenth amino acid residues and bond F between the seventh and eleventh amino acid residues, or two cyclic structures by bond I between the third and tenth amino acid residue and bond J between the seventh and eleventh amino acid residue, (4) two cyclic structures with bond K between the first, seventh, and tenth amino acid residues; (5) two cyclic structures with bond L or bond N between the second, seventh and tenth amino acid residues; or (6) two cyclic structures with bond M or bond O between the third, seventh and tenth amino acid residues. Examples of amino acid residues provided for substitution at each amino acid position of VIpep-3 and the positions of amino acid residues considered for bicyclization are shown in FIG. 2.

[1] The cyclic peptides shown in FIG. 1 can be more specifically represented by the following formula (1):

$$c[X^{N}\text{-}X^{4}\text{-}X^{5}\text{-}X^{6}\text{-}c(X^{7}\text{-}X^{8}\text{-}X^{9}\text{-}X^{10}]\text{—}X^{11})\text{-}X^{12}\text{-}X^{13}\text{-}X^{14}\text{-}X^{15}\text{-}X^{16} \quad (1)$$

or formula (2):

$$c[X^{N}\text{-}X^{4}\text{-}X^{5}\text{-}X^{6}\text{-}c(X^{7}\text{-}X^{8}\text{-}X^{9}\text{-}X^{10})]\text{—}X^{11}\text{-}X^{12}\text{-}X^{13}\text{-}X^{14}\text{-}X^{15}\text{-}X^{16} \quad (2).$$

Here, $X^N$ and $X^{10}$, and $X^7$ and $X^{11}$ in formula (1), and $X^N$, $X^7$ and $X^{10}$ in formula (2), independently of each other, covalently bind to form two cyclic structures in a molecule; each of the covalent bonds is any linkage between a main-chain and a side-chain, or between side-chains thereof, or may be an indirect covalent bond via a linker.

In formulae (1) and (2) above, $X^N$ denotes $X^1$-$X^2$-$X^3$; and $X^1$, $X^2$, $X^3$, $X^7$, $X^{10}$ and $X^{11}$ each independently denotes, in a case where involving cyclization of the molecule, an amino acid residue having an amino group, a carboxyl group, a thiol group, an allyl group, an alkynyl group, an azido group or a halogen atom, or a derivative thereof, or in a case of not involving cyclization of the molecule, $X^1$ and $X^2$ each independently denotes any amino acid residue or deletion, and $X^3$ and $X^{11}$ each independently denotes any amino acid residue. $X^5$, $X^9$, $X^{12}$, and $X^{13}$ each independently denotes an amino acid reside having a hydrocarbon group optionally containing a substituent, or a derivative thereof, $X^4$ denotes an amino acid reside having an aromatic carbocyclic group optionally containing a substituent, or a derivative thereof; $X^6$ and $X^8$ each independently denotes any amino acid residue; $X^{14}$, $X^{15}$ and $X^{16}$ each independently denotes any amino acid residue or deletion; and an N-terminal amino group and a C-terminal carboxyl group may be modified or deleted.

[2] A preferred embodiment of formula (1) is a cyclic peptide or a pharmaceutically acceptable salt of the peptide comprising the amino acid sequence represented by the following formula (3):

$$c[X^{1}\text{-}X^{2}\text{-}X^{3}\text{-}X^{4}\text{-}X^{5}\text{-}X^{6}\text{-}c(X^{7}\text{-}X^{8}\text{-}X^{9}\text{-}X^{10}]\text{—}X^{11})\text{-}X^{12}\text{-}X^{13} \quad (3).$$

In formula (3), $X^1$ and $X^{10}$, and $X^7$ and $X^{11}$, independently of each other, covalently bind to form two cyclic structures in a molecule, wherein the covalent bond is formed between a main or side chain of $X^1$ and a side chain of $X^{10}$, and between a side chain of $X^7$ and a side chain of $X^{11}$; and $X^1$ through $X^{13}$ are same as described in [1].

In one embodiment, $X^1$ represents cysteine, D-cysteine, 3-mercaptopropanoic acid, 2,3-diaminopropanoic acid, D-2,3-diaminopropanoic acid, beta-alanine, aspartic acid, or glutamic acid, and $X^{10}$ represents cysteine, D-cysteine, 2,3-diaminopropanoic acid, D-2,3-diaminopropanoic acid, aspartic acid, or glutamic acid, $X^2$ and $X^3$ each independently represent any amino acid residue, preferably proline, and $X^4$ and $X^8$ each independently represent an amino acid residue having an aromatic carbon, preferably tyrosine, phenylalanine, or a derivative thereof, $X^5$, $X^9$, $X^{12}$ and $X^{13}$ each independently represent leucine, isoleucine or a derivative thereof, $X^7$ and $X^{11}$ each independently represent lysine, ornithine, arginine, 2,3-diaminopropanoic acid, 2,4-diaminobutane 2,4-diaminobutanoic acid, aspartic acid, glutamic acid, cysteine, homocysteine, or a derivative thereof.

[3] Here, a linkage between Cα carbon atoms of $X^1$ and $X^{10}$ preferably comprises a structure represented by the following formula (4):

$$C\alpha^{1}\text{—}(CH_2)_A\text{-}L^{1}\text{-}(CH_2)_B\text{—}C\alpha^{10} \quad (4)$$

In the formula, A and B each independently denotes an integer from 0 to 2, and the sum of A and B is an integer from 1 to 4. The linker $L^1$ is S, S—S, $CH_2$—$CH_2$, S—$CH_2$, $CH_2$—S, O—$CH_2$, $CH_2$—O, CH═CH, NH—C(═O), N($CH_3$)—C(═O), NH—C(═S), N($CH_3$)—C(═S), O—C(═O), C(═O)—NH, C(═O)—N($CH_3$), C(═S)—NH, C(═S)—N($CH_3$), C(═O)—O, $CH_2$—$CH_2$—$CH_2$, S—$CH_2$—$CH_2$, $CH_2$—$CH_2$—S, $CH_2$—S—$CH_2$, O—$CH_2$—$CH_2$, $CH_2$—$CH_2$—O, $CH_2$—O—$CH_2$, S—$CH_2$—S, S—C(═$CH_2$)—S, S—$(CH_2)_2$—S, or triazole.

Among these, it is preferred that $L^1$ represents S—S, NH—C(═O), $CH_2$—S—$CH_2$, CH═CH, or $CH_2$—$CH_2$, and even more preferably when $L^1$ represents S—S or NH—C(═O). When $L^1$ represents S—S, for example, it is a structure in which $X^1$ and $X^{10}$ are both amino acid residues having thiol groups or derivatives thereof, and a disulfide bond is formed under oxidative conditions. When $L^1$ represents NH—C(═O), for example, $X^1$ is an amino acid residue having an amino group in the side chain, $X^{10}$ is an amino acid residue having a carboxy group in the side chain, and the structure is cyclized by dehydration condensation of the amino group and the carboxy group. Amino acid residues with thiol groups on the side chain include, for example, cysteine, D-cysteine, 3-mercaptopropanoic acid, homocysteine, and D-homocysteine, etc. Amino acid residues having amino groups on the side chain include, for example, 2,3-diaminopropanoic acid, D-2,3-diaminopropanoic acid, or beta-alanine, etc. Amino acid residues having carboxy groups in the side chain include, for example, aspartic acid and glutamic acid.

[4] Another preferred embodiment of formula (1) above is a cyclic peptide or a pharmaceutically acceptable salt of the peptide comprising the amino acid sequence represented by the following formula (5):

$$c[X^2\text{-}X^3\text{-}X^4\text{-}X^5\text{-}X^6\text{-}c(X^7\text{-}X^8\text{-}X^9\text{-}X^{10}]\text{-}X^{11})\text{-}X^{12}\text{-}X^{13} \quad (5)$$

In Formula (5), $X^2$ and $X^{10}$, and $X^7$ and $X^{11}$, independently of each other, covalently bind to form two cyclic structures in a molecule, and each of the covalent bonds is a linkage between a main-chain or side chain of $X^2$ and a side chain of $X^{10}$, or between a side chain of $X^7$ and a side chain of $X^{11}$, while $X^2$ through $X^{13}$ are same as described in [1].

[5] Here, a linkage between Cα carbon atoms of $X^2$ and $X^{10}$ preferably comprises a structure represented by the following formula (6):

$$C\alpha^2\text{—}(CH_2)_A\text{-}L^2\text{-}(CH_2)_B\text{—}C\alpha^{10} \quad (6)$$

In the formula, A and B each independently denotes an integer from 0 to 6, the sum of A and B is an integer from 4 to 7; and $L^2$ is S, S—S, $CH_2$—$CH_2$, S—$CH_2$, $CH_2$—S, O—$CH_2$, $CH_2$—O, CH═CH, NH—C(═O), N ($CH_3$)—C(═O), NH—C(═S), N($CH_3$)—C(═S), O—C(═O), C(═O)—NH, C(═O)—N($CH_3$), C(═S)—NH, C(═S)—N($CH_3$), C(═O)—O, $CH_2$—$CH_2$—$CH_2$, S—$CH_2$—$CH_2$, $CH_2$—$CH_2$—S, $CH_2$—S—$CH_2$, O—$CH_2$—$CH_2$, $CH_2$—$CH_2$—O, $CH_2$—O—$CH_2$, S—$CH_2$—S, S—C(═$CH_2$)—S, S—$(CH_2)_2$—S, S—$(CH_2)_3$—S, S—$(CH_2)_4$—S, S—$(CH_2)_5$—S, S—$CH_2$—CH═CH—$CH_2$—S, S—$CH_2$—C(═O)—NH, NH—C(═O)—$CH_2$—S, S—$CH_2$—$C_6H_4$—$CH_2$—S (the attached site of methylene group to the phenyl ring is any one of ortho, meta and para), S—$CH_2$-$C_{10}H_6$—$CH_2$—S, S—$CH_2$—C(═O)—$CH_2$—S or S—$CH_2$—C(═$CH_2$)—$CH_2$—S, triazole or dithiotetrafluorobenzene.

Among these, it is preferred that $L^2$ represents S—$(CH_2)_2$—S, S—S, S—$(CH_2)_3$—S, S—$(CH_2)_4$—S, S—$(CH_2)_5$—S. For example, $X^2$ and $X^{10}$ are both amino acid residues having thiol groups or derivatives thereof, and a thioether bond can be formed between the thiol group of these residues and alkyl halide linkers such as 1,2-diiodoethane, 1,3-diiodopropane, and 1,4-diiodobutane.

[6] Still other preferred embodiment of formula (1) above is a cyclic peptide or a pharmaceutically acceptable salt of the peptide comprising the amino acid sequence represented by the following formula (7):

$$c[X^3\text{-}X^4\text{-}X^5\text{-}X^6\text{-}c(X^7\text{-}X^8\text{-}X^9\text{-}X^{10}]\text{—}X^{11})\text{-}X^{12}\text{-}X^{13} \quad (7)$$

In formula (7), $X^3$ and $X^{10}$, and $X^7$ and $X^{11}$ covalently bind to each other to form two cyclic structures in a molecule;

each of the covalent bonds is a linkage of either between main-chain and side chain, or between side chain and side chain thereof; and $X^3$ through $X^{13}$ are same as described in [1].

In one embodiment, $X^3$ represents cysteine, D-cysteine, homocysteine, D-homocysteine, 3-mercaptopropanoic acid, 3-mercaptohexanoic acid, 6-mercaptohexanoic acid, or 8-mercaptohexanoic acid, and $X^{10}$ represents cysteine, D-cysteine, homocysteine, or D-homocysteine, $X^4$ and $X^8$ each independently represent an amino acid residue having an aromatic carbon ring group, preferably tyrosine, phenylalanine, or a derivative thereof, and $X^5$, $X^9$, $X^{12}$ and $X^{13}$ each independently represent leucine, isoleucine or their derivatives, $X^7$ and $X^{11}$ each independently represent lysine, ornithine, arginine, 2,3-diamidino 2,3-diaminopropanoic acid, 2,4-diaminobutanoic acid, aspartic acid, glutamic acid, or their derivatives.

[7] Here, a linkage between Cα carbon atoms of $X^3$ and $X^{10}$ preferably comprises a structure represented by the following formula (8):

$$C\alpha^3\text{—}(CH_2)_A\text{-}L^3\text{-}(CH_2)_B\text{—}C\alpha^{10} \quad (8)$$

In the formula, A and B each independently denotes an integer from 0 to 10, the sum of A and B is an integer from 7 to 10, and $L^7$ is S, S—S, $CH_2$—$CH_2$, S—$CH_2$, $CH_2$—S, O—$CH_2$, $CH_2$—O, CH═CH, NH—C(═O), N ($CH_3$)—C(═O), NH—C(═S), N($CH_3$)—C(═S), O—C(═O), C(═O)—NH, C(═O)—N($CH_3$), C(═S)—NH, C(═S)—N($CH_3$), C(═O)—O, $CH_2$—$CH_2$—$CH_2$, S—$CH_2$—$CH_2$, $CH_2$—$CH_2$—S, $CH_2$—S—$CH_2$, O—$CH_2$—$CH_2$, $CH_2$—$CH_2$—O, $CH_2$—O—$CH_2$, S—$CH_2$—S, S—C(═$CH_2$)—S, S—$(CH_2)_2$—S, S—$(CH_2)_3$—S, S—$(CH_2)_4$—S, S—$CH_2$—$C_6H_4$—$CH_2$—S(the attached site of methylene group to the phenyl ring is any one of ortho, meta and para), S—$CH_2$-$C_{10}H_6$—$CH_2$—S, S—$CH_2$—C(═O)—$CH_2$—S or S—$CH_2$—C(═$CH_2$)—$CH_2$—S, triazole or dithiotetrafluorobenzene.

Among these, it is preferred that $L^3$ represents S—$(CH_2)_3$—S, S—$(CH_2)_4$—S, S—$(CH_2)_5$—S, S—$(CH_2)_6$—S, or S—$CH_2$—$C_6H_4$—$CH_2$—S(the bonding site of the methylene group to the phenylene ring may be ortho, meta and para). For example, $X^3$ and $X^{10}$ are both amino acid residues having thiol groups or derivatives thereof, and thioether bonds can be formed between the thiol groups of these residues and alkyl halide linkers such as 1,3-diiodopropane, 1,4-diiodobutane, 1,5-diiodopentane, 1,6-diiodohexane, 1,2-bisbromomethylbenzene, 1,3-bisbromomethylbenzene, or 1,4-bisbromomethylbenzene.

[8] Other preferred embodiments of the above formulae (1), (3), (5) and (7) is a cyclic peptide or a pharmaceutically acceptable salt of the peptide comprising the amino acid sequence represented by the following formula (9):

$$C\alpha^7\text{—}(CH_2)_A\text{-}L^7\text{-}(CH_2)_B\text{—}C\alpha^{11} \quad (9)$$

In the formula, A and B each independently denotes an integer from 0 to 7, a sum of A and B is an integer from 2 to 7, and $L^7$ is S, S—S, $CH_2$—$CH_2$, S—$CH_2$, $CH_2$—S, O—$CH_2$, $CH_2$—O, CH═CH, NH—C(═O), N ($CH_3$)—C(═O), NH—C(═S), N ($CH_3$)—C(═S), O—C(═O), C(═O)—NH, C(═O)—N($CH_3$), C(═S)—NH, C(═S)—N ($CH_3$), C(═O)—O, $CH_2$—$CH_2$—$CH_2$, S—$CH_2$—$CH_2$, $CH_2$—$CH_2$—S, $CH_2$—S—$CH_2$, O—$CH_2$—$CH_2$, $CH_2$—$CH_2$—O, $CH_2$—O—$CH_2$, S—$CH_2$—S, S—C(═$CH_2$)—S, S—$(CH_2)_2$—S, S—$(CH_2)_3$—S, S—$(CH_2)_4$—S, S—$CH_2$—CH═CH—$CH_2$—S, S—$CH_2$—C(═O)—NH, NH—C(═O)—$CH_2$—S, S—$CH_2$—$C_6H_4$—$CH_2$—S(the attached site of methylene group to the phenylene ring is any one of ortho, meta and para), S—$CH_2$—C(═O)—$CH_2$—S, or S—$CH_2$—C(═$CH_2$)—$CH_2$—S, triazole, or dithiotetrafluorobenzene.

Among these, it is preferred that $L^7$ represents NH—C(═O), S—S, or S—$(CH_2)_3$—S. The case where $L^7$ represents NH—C(═O) means, for example, that $X^7$ is an amino acid residue having an amino group in the side chain and $X^{11}$ is an amino acid residue having a carboxy group in the side chain, and the cyclized structure by dehydration-condensation of these amino groups and carboxy groups. When $L^7$ represents S—S, for example, $X^7$ and $X^{11}$ are both amino acid residues having a thiol group or their derivatives, and the structure is formed by disulfide bond formation under oxidative conditions. When $L^7$ represents S—$(CH_2)_3$—S means, for example, that $X^7$ and $X^{11}$ are both amino acid residues having a thiol group or derivatives thereof, and a thioether bond can be formed between the thiol groups of these residues and an alkyl halide linker such as 1,3-diiodopropane. Amino acid residues having amino groups in the side chain include, for example, lysine and ornithine. Amino acid residues having carboxy groups in the side chain include, for example, aspartic acid and glutamic acid. Amino acid residues having thiol groups in the side chain include, for example, cysteine, D-cysteine, homocysteine, D-homocysteine, etc.

[9] A preferred embodiment of formula (2) above is a cyclic peptide or a pharmaceutically acceptable salt of the peptide comprising the amino acid sequence represented by the following formula (10):

$$c[X^3\text{-}X^4\text{-}X^5\text{-}X^6\text{-}c(X^7\text{-}X^8\text{-}X^9\text{-}X^{10})]—X^{11}\text{-}X^{12}\text{-}X^{13} \qquad (10)$$

In formula (10), $X^3$, $X^7$ and $X^{11}$ covalently bind to each other to form two cyclic structures in a molecule; and $X^3$ through $X^{13}$ are same as described in [1]

In one embodiment, $X^3$ represents cysteine, D-cysteine, homocysteine, D-homocysteine, or 3-mercaptopropanoic acid, $X^7$ and $X^{10}$ each independently represent cysteine, D-cysteine, homocysteine, or D-homocysteine, $X^4$ and $X^8$ each independently represent an amino acid residue having an aromatic carbon ring group, preferably tyrosine, phenylalanine, or a derivative thereof, and $X^5$, $X^9$, $X^{12}$ and $X^{13}$ each independently represents leucine, isoleucine, or their derivatives, and $X^{11}$ represents serine, threonine, diaminopropanoic acid, diaminobutanoic acid, or their derivatives.

[10] Here, in the cyclic peptide shown in formulae (2) or (10) above, a linkage between Cα carbon atoms of $X^1$, $X^7$ and $X^{11}$, $X^2$, $X^7$ and $X^{11}$, or $X^3$, $X^7$ and $X^{11}$ preferably comprises a structure represented by the following formula (11):

(11)

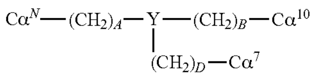

In the formula, N denotes 1, 2, or 3, and A, B, and D each independently denotes 1 or 2, and Y denotes $[(S—CH_3)_3—C_6H_3]$, $[(S—CH_2—CH_2—C({=}O))_3—C_3N_3H_6]$, $[(S—CH_2—C({=}O)—NH)_3\text{-}C_6H_3]$, $[(NH—C({=}O))_3—C_6H_3]$, $[(S—CH_3)_3—C_3N_3H_6]$ or $[(S—CH_2—C({=}O))_3—C_3N_3H_6]$.

Among these, it is preferred that Y represents $[(S—CH_3)_3—C_6H_3]$. For example, if $X^3$ is 3-mercaptopropanoic acid (Mpa) and $X^7$ and $X^{10}$ are both an amino acid residue having a thiol group such as cysteine (Cys), the thioether bond between the thiol group of these residues and an alkyl halide linker such as 1,3,5-tris(bromomethyl)benzene allows the peptide to be cyclized.

[11] Also, in the cyclic peptides shown in formula (2) or (10) above, a linkage between the Cα carbon atoms of $X^1$, $X^7$ and $X^{11}$, $X^2$, $X^7$ and $X^{11}$, or $X^3$, $X^7$ and $X^{11}$ is preferred to have the structure represented by the following formula (12):

(12)

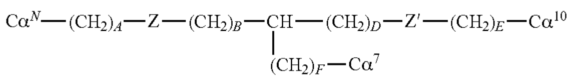

In the formula, N denotes 1, 2, or 3, A, B, D, E, and F each independently denotes an integer of 1 or 2, and Z and Z' each independently denotes S, S—S, S—$CH_2$—S, S—C(=$CH_2$)—S, S—$(CH_2)_2$—S, S—$(CH_2)_3$—S, S—$(CH_2)_4$—S, S—$CH_2$—CH=CH—$CH_2$—S, S—$CH_2$—C(=O)—NH, NH—C(=O)—$CH_2$—S, S—$CH_2$—$C_6H_4$—$CH_2$—S (the attached site of methylene group to the phenylene ring can be ortho, meta or para), S—$CH_2$-$C_6H_4$-$C_6H_4$—$CH_2$—S, S—$CH_2$-$C_{10}H_6$—$CH_2$—S, S—$CH_2$—C(=O)—$CH_2$—S, S—$CH_2$—C(=$CH_2$)—$CH_2$—S, or dithiotetrafluorobenzene.

[12] In the cyclic peptides shown in formulae (1) to (3), (5), (7) and (10) above, it is preferred that $X^5$, $X^9$, $X^{12}$ and $X^{13}$ are each independently an amino acid residue represented by the following formula (13):

(13)

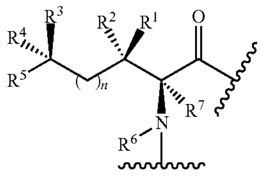

In the formula, the wavy line denotes the point of attachment to the carbonyl group forming an amide bond in the main chain or a nitrogen atom, $R^1$, $R^2$, $R^6$ and $R^7$ each independently denotes a hydrogen atom or a methyl group, and $R^3$, $R^4$, $R^5$ each independently denotes a hydrogen atom, a methyl group, or a halogen atom (F, Cl, Br, I), and n denotes an integer from 0 to 10. Particularly preferred among these are leucine, N-methylated leucine, α-methylated leucine, isoleucine, β-homoleucine, norvaline, norleucine, 2-aminoheptanoic acid, 2-aminooctanoic acid, 2-aminononanoic acid and the like.

Alternatively, $X^5$, $X^9$, $X^{12}$ and $X^{13}$ may be an amino acid residue represented by the following equations (14):

(14)

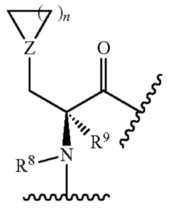

In the formula, the wavy line denotes the point of attachment to the carbonyl group forming an amide bond in the main chain or a nitrogen atom, Z denotes C or N, $R^8$ and $R^9$, each denotes a hydrogen atom or a methyl group, and n denotes an integer from 1 to 6. Particularly preferred among these are cyclopropylalanine and cyclobutylalanine.

[13] In the cyclic peptides shown in formulae (1) to (3), (5), (7) and (10) above, it is preferable that $X^4$ is an amino acid residue represented by the following formula (15):

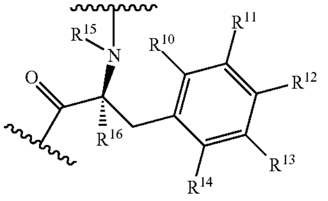

(15)

In the formula, the wavy line denotes the point of attachment with the carbonyl group forming an amide bond in the main chain, or a nitrogen atom, and $R^{10}$, $R^{11}$, $R^{12}$, $R^{13}$ and $R^{14}$ each independently denotes a hydrogen atom, a hydroxy group, a hydroxymethyl group, a methoxy group, a methoxymethyl group, an amino group, an aminomethyl group, a monomethylated amino group, a dimethylated amino group, a trimethylated amino group, a monomethylated aminomethyl group, a dimethylated aminomethyl group, a trimethylated aminomethyl group, an acetyl group, an amide group, a methyl group, a tert-butyl group, a methyl halide, or a halogen atom (F, Cl, Br, I), and $R^{15}$ and $R^{16}$ each denotes a hydrogen atom or a methyl group.

Among these, it is preferred that $X^4$ denotes tyrosine, 3-hydroxyphenylalanine, 4-fluorophenylalanine, 4-aminophenylalanine, 4-aminomethylphenylalanine, 4-amidophenylalanine, N-methylated tyrosine, α-methylated tyrosine, O-methyl-tyrosine, 3-methoxy-phenylalanine and 4-acetyl-phenylalanine.

[14] In the cyclic peptides shown in formulas (1) to (3), (5), (7) and (10) above, it is preferred that $X^8$ is an amino acid residue having an aromatic carbon ring group that may have a substituent, or a derivative thereof.

[15] As a specific embodiment of $X^8$ which has an aromatic carbon ring group, it is preferred that an amino acid residue is represented by the following formula (16):

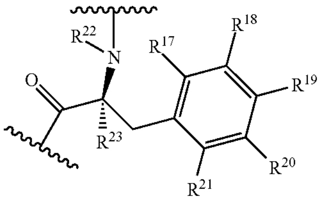

(16)

In the formula, the wavy line denotes the point of attachment with the carbonyl group forming an amide bond in the main chain, or a nitrogen atom, and $R^{17}$, $R^{18}$, $R^{19}$, $R^{20}$ and $R^{21}$ each independently denotes a hydrogen atom, a hydroxy group, a hydroxymethyl group, a methoxy group, a methoxymethyl group, an amino group a tert-butyl group, a methyl halide group, or a halogen atom (F, Cl, Br, I), and $R^{22}$ and $R^{23}$ each denotes a hydrogen atom or a methyl group.

Among these, it is further preferred that $X^8$ denotes tyrosine, 3-hydroxyphenylalanine, 4-fluorophenylalanine, 4-aminophenylalanine, 4-aminomethylphenylalanine, 4-amidophenylalanine, N-methylated tyrosine, α-methylated tyrosine, O-methyl-tyrosine, 3-methoxy-phenylalanine and 4-acetyl-phenylalanine.

[16] Furthermore, in the above formulae (1) to (3), (5), (7) and (10), it is preferred that $X^6$ denotes glycine, N-methylated glycine, alanine, N-methylated alanine, D-alanine, N-methylated D-alanine, 2-aminoisobutyric acid, N-methylated 2-aminoisobutyric acid, 2-azetidine-2-carboxylic acid, D-2-azetidine-2-carboxylic acid, proline, D-proline, thioproline, D-thioproline, 3,4-dehydroproline, D-3,4-dehydroproline, pipecolinic acid, D-pipecolinic acid.

Among these, it is more preferred that $X^6$ denotes proline, N-methylated glycine, N-methylated alanine, 2-azetidine-2-carboxylic acid, and pipecolinic acid.

[17] The cyclic peptide in one aspect of embodiments comprises an amino acid sequence represented by the following formula (17):

$$c[X^1\text{-Pro-}X^3\text{-Tyr}^4\text{-Leu}^5\text{-Pro}^6\text{-}c(X^7\text{-}X^8\text{-Leu}^9\text{-Cys}^{10}]\text{-}X^{11})\text{-}X^{12}\text{-}X^{13} \quad (17).$$

In formula (17), $X^1$ denotes cysteine, Mpa (3-mercaptopropionic acid), or D-cysteine; $X^3$ denotes N-methylglycine, N-methylalanine, 2-azetidine-2-carboxylic acid, proline, hydroxyproline, 3,4-dehydroprolone, pipecolic acid, serine, or lysine; $X^8$ denotes tyrosine, proline, or arginine; $X^7$ and $X^{11}$ denotes any combination of lysine and aspartic acid, ornithine and glutamic acid, aspartic acid and lysine, glutamic acid and ornithine, lysine and glutamic acid, or glutamic acid and lysine; $X^{12}$ and $X^{13}$, each independently denotes leucine, isoleucine or norleucine; $X^1$ and $Cys^{10}$ form a disulfide bond between their side chains, and $X^7$ and $X^{11}$ form an amide bond between their side chains, thereby forming two cyclic structures in a molecule of the peptide of formula (17); and an N-terminal amino group and a C-terminal carboxyl group may be modified or deleted.

[18] A more preferred embodiment of the cyclic peptide in formula (17) is such a peptide that $X^1$ denotes cysteine; $X^3$ denotes proline or serine; $X^7$ denotes lysine; $X^8$ denotes tyrosine; $X^{11}$ denotes aspartic acid; $X^{12}$ and $X^{13}$, each independently denotes leucine, isoleucine or norleucine; and an N-terminal amino group is acetylated, and a C-terminal carboxyl group is amidated.

The individual cyclic peptides in the above [17] or [18] can be enumerated as follows:

(SEQ ID No. 10)
$Ac\text{-}c[Cys^1\text{-}Pro^2\text{-}Pro^3\text{-}Tyr^4\text{-}Leu^5\text{-}Pro^6\text{-}c(Lys^7\text{-}Tyr^8\text{-}Leu^9\text{-}Cys^{10}]\text{-}Asp^{11})\text{-}Leu^{12}\text{-}Ile^{13}\text{-}NH_2$ $Ac\text{-}c[Cys^1\text{-}Pro^2\text{-}Ser^3\text{-}Tyr^4\text{-}Leu^5\text{-}Pro^6\text{-}c(Lys^7\text{-}Tyr^8\text{-}Leu^9\text{-}Cys^{10}]\text{-}Asp^{11})\text{-}Leu^{12}\text{-}Ile^{13}\text{-}NH_2$ $Ac\text{-}c[Cys^1\text{-}Pro^2\text{-}Pro^3\text{-}Tyr^4\text{-}Leu^5\text{-}Pro^6\text{-}c(Orn^7\text{-}Tyr^8\text{-}Leu^9\text{-}Cys^{10}]\text{-}Glu^{11})\text{-}Leu^{12}\text{-}Ile^{13}\text{-}NH_2$ $Ac\text{-}c[Cys^1\text{-}Pro^2\text{-}Ser^3\text{-}Tyr^4\text{-}Leu^5\text{-}Pro^6\text{-}c(Orn^7\text{-}Tyr^8\text{-}Leu^9\text{-}Cys^{10}]\text{-}Glu^{11})\text{-}Leu^{12}\text{-}Ile^{13}\text{-}NH_2$ -continued Ac-c[$Cys^1$-$Pro^2$-$Pro^3$-$Tyr^4$-$Leu^5$-$Pro^6$-c($Asp^7$-$Tyr^8$-$Leu^9$-$Cys^{10}$]-$Lys^{11}$)-$Leu^{12}$-$Ile^{13}$-$NH_2$ Ac-c[$Cys^1$-$Pro^2$-$Ser^3$-$Tyr^4$-$Leu^5$-$Pro^6$-c($Asp^7$-$Tyr^8$-$Leu^9$-$Cys^{10}$]-$Lys^{11}$)-$Leu^{12}$-$Ile^{13}$-$NH_2$ Ac-c[$Cys^1$-$Pro^2$-$Pro^3$-$Tyr^4$-$Leu^5$-$Pro^6$-c($Glu^7$-$Tyr^8$-$Leu^9$-$Cys^{10}$]-$Orn^{11}$)-$Leu^{12}$-$Ile^{13}$-$NH_2$ Ac-c[$Cys^1$-$Pro^2$-$Ser^3$-$Tyr^4$-$Leu^5$-$Pro^6$-c($Glu^7$-$Tyr^8$-$Leu^9$-$Cys^{10}$]-$Orn^{11}$)-$Leu^{12}$-$Ile^{13}$-$NH_2$ Ac-c[$Cys^1$-$Pro^2$-$Pro^3$-$Tyr^4$-$Leu^5$-$Pro^6$-c($Lys^7$-$Tyr^8$-$Leu^9$-$Cys^{10}$]-$Asp^{11}$)-$Leu^{12}$-$Leu^{13}$-$NH_2$ Ac-c[$Cys^1$-$Pro^2$-$Ser^3$-$Tyr^4$-$Leu^5$-$Pro^6$-c($Lys^7$-$Tyr^8$-$Leu^9$-$Cys^{10}$]-$Asp^{11}$)-$Leu^{12}$-$Leu^{13}$-$NH_2$ Ac-c[$Cys^1$-$Pro^2$-$Pro^3$-$Tyr^4$-$Leu^5$-$Pro^6$-c($Orn^7$-$Tyr^8$-$Leu^9$-$Cys^{10}$]-$Glu^{11}$)-$Leu^{12}$-$Leu^{13}$-$NH_2$ Ac-c[$Cys^1$-$Pro^2$-$Ser^3$-$Tyr^4$-$Leu^5$-$Pro^6$-c($Orn^7$-$Tyr^8$-$Leu^9$-$Cys^{10}$]-$Glu^{11}$)-$Leu^{12}$-$Leu^{13}$-$NH_2$ Ac-c[$Cys^1$-$Pro^2$-$Pro^3$-$Tyr^4$-$Leu^5$-$Pro^6$-c($Asp^7$-$Tyr^8$-$Leu^9$-$Cys^{10}$]-$Lys^{11}$)-$Leu^{12}$-$Leu^{13}$-$NH_2$ Ac-c[$Cys^1$-$Pro^2$-$Ser^3$-$Tyr^4$-$Leu^5$-$Pro^6$-c($Asp^7$-$Tyr^8$-$Leu^9$-$Cys^{10}$]-$Lys^{11}$)-$Leu^{12}$-$Leu^{13}$-$NH_2$ Ac-c[$Cys^1$-$Pro^2$-$Pro^3$-$Tyr^4$-$Leu^5$-$Pro^6$-c($Glu^7$-$Tyr^8$-$Leu^9$-$Cys^{10}$]-$Orn^{11}$)-$Leu^{12}$-$Leu^{13}$-$NH_2$ Ac-c[$Cys^1$-$Pro^2$-$Ser^3$-$Tyr^4$-$Leu^5$-$Pro^6$-c($Glu^7$-$Tyr^8$-$Leu^9$-$Cys^{10}$]-$Orn^{11}$)-$Leu^{12}$-$Leu^{13}$-$NH_2$ Ac-c[$Cys^1$-$Pro^2$-$Pro^3$-$Tyr^4$-$Leu^5$-$Pro^6$-c($Lys^7$-$Tyr^8$-$Leu^9$-$Cys^{10}$]-$Asp^{11}$)-$Nle^{12}$-$Ile^{13}$-$NH_2$ Ac-c[$Cys^1$-$Pro^2$-$Ser^3$-$Tyr^4$-$Leu^5$-$Pro^6$-c($Lys^7$-$Tyr^8$-$Leu^9$-$Cys^{10}$]-$Asp^{11}$)-$Nle^{12}$-$Ile^{13}$-$NH_2$ Ac-c[$Cys^1$-$Pro^2$-$Pro^3$-$Tyr^4$-$Leu^5$-$Pro^6$-c($Orn^7$-$Tyr^8$-$Leu^9$-$Cys^{10}$]-$Glu^{11}$)-$Nle^{12}$-$Ile^{13}$-$NH_2$ Ac-c[$Cys^1$-$Pro^2$-$Ser^3$-$Tyr^4$-$Leu^5$-$Pro^6$-c($Orn^7$-$Tyr^8$-$Leu^9$-$Cys^{10}$]-$Glu^{11}$)-$Nle^{12}$-$Ile^{13}$-$NH_2$ Ac-c[$Cys^1$-$Pro^2$-$Pro^3$-$Tyr^4$-$Leu^5$-$Pro^6$-c($Asp^7$-$Tyr^8$-$Leu^9$-$Cys^{10}$]-$Lys^{11}$)-$Nle^{12}$-$Ile^{13}$-$NH_2$ Ac-c[$Cys^1$-$Pro^2$-$Ser^3$-$Tyr^4$-$Leu^5$-$Pro^6$-c($Asp^7$-$Tyr^8$-$Leu^9$-$Cys^{10}$]-$Lys^{11}$)-$Nle^{12}$-$Ile^{13}$-$NH_2$ Ac-c[$Cys^1$-$Pro^2$-$Pro^3$-$Tyr^4$-$Leu^5$-$Pro^6$-c($Glu^7$-$Tyr^8$-$Leu^9$-$Cys^{10}$]-$Orn^{11}$)-$Nle^{12}$-$Ile^{13}$-$NH_2$ Ac-c[$Cys^1$-$Pro^2$-$Ser^3$-$Tyr^4$-$Leu^5$-$Pro^6$-c($Glu^7$-$Tyr^8$-$Leu^9$-$Cys^{10}$]-$Orn^{11}$)-$Nle^{12}$-$Ile^{13}$-$NH_2$ Ac-c[$Cys^1$-$Pro^2$-$Pro^3$-$Tyr^4$-$Leu^5$-$Pro^6$-c($Lys^7$-$Tyr^8$-$Leu^9$-$Cys^{10}$]-$Asp^{11}$)-$Nle^{12}$-$Leu^{13}$-$NH_2$ Ac-c[$Cys^1$-$Pro^2$-$Ser^3$-$Tyr^4$-$Leu^5$-$Pro^6$-c($Lys^7$-$Tyr^8$-$Leu^9$-$Cys^{10}$]-$Asp^{11}$)-$Nle^{12}$-$Leu^{13}$-$NH_2$ Ac-c[$Cys^1$-$Pro^2$-$Pro^3$-$Tyr^4$-$Leu^5$-$Pro^6$-c($Orn^7$-$Tyr^8$-$Leu^9$-$Cys^{10}$]-$Glu^{11}$)-$Nle^{12}$-$Leu^{13}$-$NH_2$ Ac-c[$Cys^1$-$Pro^2$-$Ser^3$-$Tyr^4$-$Leu^5$-$Pro^6$-c($Orn^7$-$Tyr^8$-$Leu^9$-$Cys^{10}$]-$Glu^{11}$)-$Nle^{12}$-$Leu^{13}$-$NH_2$ Ac-c[$Cys^1$-$Pro^2$-$Pro^3$-$Tyr^4$-$Leu^5$-$Pro^6$-c($Asp^7$-$Tyr^8$-$Leu^9$-$Cys^{10}$]-$Lys^{11}$)-$Nle^{12}$-$Leu^{13}$-$NH_2$ Ac-c[$Cys^1$-$Pro^2$-$Ser^3$-$Tyr^4$-$Leu^5$-$Pro^6$-c($Asp^7$-$Tyr^8$-$Leu^9$-$Cys^{10}$]-$Lys^{11}$)-$Nle^{12}$-$Leu^{13}$-$NH_2$ Ac-c[$Cys^1$-$Pro^2$-$Pro^3$-$Tyr^4$-$Leu^5$-$Pro^6$-c($Glu^7$-$Tyr^8$-$Leu^9$-$Cys^{10}$]-$Orn^{11}$)-$Nle^{12}$-$Leu^{13}$-$NH_2$ -continued Ac-c[$Cys^1$-$Pro^2$-$Ser^3$-$Tyr^4$-$Leu^5$-$Pro^6$-c($Glu^7$-$Tyr^8$-$Leu^9$-$Cys^{10}$]-$Orn^{11}$)-$Nle^{12}$-$Leu^{13}$-$NH_2$ Ac-c[$Cys^1$-$Pro^2$-$Pro^3$-$Arg^4$-$Leu^5$-$Pro^6$-c($Lys^7$-$Arg^8$-$Leu^9$-$Cys^{10}$]-$Asp^{11}$)-$Leu^{12}$-$Ile^{13}$-$NH_2$ Ac-c[$Cys^1$-$Pro^2$-$Ser^3$-$Arg^4$-$Leu^5$-$Pro^6$-c($Lys^7$-$Arg^8$-$Leu^9$-$Cys^{10}$]-$Asp^{11}$)-$Leu^{12}$-$Ile^{13}$-$NH_2$ Ac-c[$Cys^1$-$Pro^2$-$Pro^3$-$Arg^4$-$Leu^5$-$Pro^6$-c($Orn^7$-$Arg^8$-$Leu^9$-$Cys^{10}$]-$Glu^{11}$)-$Leu^{12}$-$Ile^{13}$-$NH_2$ Ac-c[$Cys^1$-$Pro^2$-$Ser^3$-$Arg^4$-$Leu^5$-$Pro^6$-c($Orn^7$-$Arg^8$-$Leu^9$-$Cys^{10}$]-$Glu^{11}$)-$Leu^{12}$-$Ile^{13}$-$NH_2$ Ac-c[$Cys^1$-$Pro^2$-$Pro^3$-$Arg^4$-$Leu^5$-$Pro^6$-c($Asp^7$-$Arg^8$-$Leu^9$-$Cys^{10}$]-$Lys^{11}$)-$Leu^{12}$-$Ile^{13}$-$NH_2$ Ac-c[$Cys^1$-$Pro^2$-$Ser^3$-$Arg^4$-$Leu^5$-$Pro^6$-c($Asp^7$-$Arg^8$-$Leu^9$-$Cys^{10}$]-$Lys^{11}$)-$Leu^{12}$-$Ile^{13}$-$NH_2$ Ac-c[$Cys^1$-$Pro^2$-$Pro^3$-$Arg^4$-$Leu^5$-$Pro^6$-c($Glu^7$-$Arg^8$-$Leu^9$-$Cys^{10}$]-$Orn^{11}$)-$Leu^{12}$-$Ile^{13}$-$NH_2$ Ac-c[$Cys^1$-$Pro^2$-$Ser^3$-$Arg^4$-$Leu^5$-$Pro^6$-c($Glu^7$-$Arg^8$-$Leu^9$-$Cys^{10}$]-$Orn^{11}$)-$Leu^{12}$-$Ile^{13}$-$NH_2$ Ac-c[$Cys^1$-$Pro^2$-$Pro^3$-$Arg^4$-$Leu^5$-$Pro^6$-c($Lys^7$-$Arg^8$-$Leu^9$-$Cys^{10}$]-$Asp^{11}$)-$Leu^{12}$-$Leu^{13}$-$NH_2$ Ac-c[$Cys^1$-$Pro^2$-$Ser^3$-$Arg^4$-$Leu^5$-$Pro^6$-c($Lys^7$-$Arg^8$-$Leu^9$-$Cys^{10}$]-$Asp^{11}$)-$Leu^{12}$-$Leu^{13}$-$NH_2$ Ac-c[$Cys^1$-$Pro^2$-$Pro^3$-$Arg^4$-$Leu^5$-$Pro^6$-c($Orn^7$-$Arg^8$-$Leu^9$-$Cys^{10}$]-$Glu^{11}$)-$Leu^{12}$-$Leu^{13}$-$NH_2$ Ac-c[$Cys^1$-$Pro^2$-$Ser^3$-$Arg^4$-$Leu^5$-$Pro^6$-c($Orn^7$-$Arg^8$-$Leu^9$-$Cys^{10}$]-$Glu^{11}$)-$Leu^{12}$-$Leu^{13}$-$NH_2$ Ac-c[$Cys^1$-$Pro^2$-$Pro^3$-$Arg^4$-$Leu^5$-$Pro^6$-c($Asp^7$-$Arg^8$-$Leu^9$-$Cys^{10}$]-$Lys^{11}$)-$Leu^{12}$-$Leu^{13}$-$NH_2$ Ac-c[$Cys^1$-$Pro^2$-$Ser^3$-$Arg^4$-$Leu^5$-$Pro^6$-c($Asp^7$-$Arg^8$-$Leu^9$-$Cys^{10}$]-$Lys^{11}$)-$Leu^{12}$-$Leu^{13}$-$NH_2$ Ac-c[$Cys^1$-$Pro^2$-$Pro^3$-$Arg^4$-$Leu^5$-$Pro^6$-c($Glu^7$-$Arg^8$-$Leu^9$-$Cys^{10}$]-$Orn^{11}$)-$Leu^{12}$-$Leu^{13}$-$NH_2$ Ac-c[$Cys^1$-$Pro^2$-$Ser^3$-$Arg^4$-$Leu^5$-$Pro^6$-c($Glu^7$-$Arg^8$-$Leu^9$-$Cys^{10}$]-$Orn^{11}$)-$Leu^{12}$-$Leu^{13}$-$NH_2$ Ac-c[$Cys^1$-$Pro^2$-$Pro^3$-$Arg^4$-$Leu^5$-$Pro^6$-c($Lys^7$-$Arg^8$-$Leu^9$-$Cys^{10}$]-$Asp^{11}$)-$Nle^{12}$-$Ile^{13}$-$NH_2$ Ac-c[$Cys^1$-$Pro^2$-$Ser^3$-$Arg^4$-$Leu^5$-$Pro^6$-c($Lys^7$-$Arg^8$-$Leu^9$-$Cys^{10}$]-$Asp^{11}$)-$Nle^{12}$-$Ile^{13}$-$NH_2$ Ac-c[$Cys^1$-$Pro^2$-$Pro^3$-$Arg^4$-$Leu^5$-$Pro^6$-c($Orn^7$-$Arg^8$-$Leu^9$-$Cys^{10}$]-$Glu^{11}$)-$Nle^{12}$-$Ile^{13}$-$NH_2$ Ac-c[$Cys^1$-$Pro^2$-$Ser^3$-$Arg^4$-$Leu^5$-$Pro^6$-c($Orn^7$-$Arg^8$-$Leu^9$-$Cys^{10}$]-$Glu^{11}$)-$Nle^{12}$-$Ile^{13}$-$NH_2$ Ac-c[$Cys^1$-$Pro^2$-$Pro^3$-$Arg^4$-$Leu^5$-$Pro^6$-c($Asp^7$-$Arg^8$-$Leu^9$-$Cys^{10}$]-$Lys^{11}$)-$Nle^{12}$-$Ile^{13}$-$NH_2$ Ac-c[$Cys^1$-$Pro^2$-$Ser^3$-$Arg^4$-$Leu^5$-$Pro^6$-c($Asp^7$-$Arg^8$-$Leu^9$-$Cys^{10}$]-$Lys^{11}$)-$Nle^{12}$-$Ile^{13}$-$NH_2$ Ac-c[$Cys^1$-$Pro^2$-$Pro^3$-$Arg^4$-$Leu^5$-$Pro^6$-c($Glu^7$-$Arg^8$-$Leu^9$-$Cys^{10}$]-$Orn^{11}$)-$Nle^{12}$-$Ile^{13}$-$NH_2$ Ac-c[$Cys^1$-$Pro^2$-$Ser^3$-$Arg^4$-$Leu^5$-$Pro^6$-c($Glu^7$-$Arg^8$-$Leu^9$-$Cys^{10}$]-$Orn^{11}$)-$Nle^{12}$-$Ile^{13}$-$NH_2$ Ac-c[$Cys^1$-$Pro^2$-$Pro^3$-$Arg^4$-$Leu^5$-$Pro^6$-c($Lys^7$-$Arg^8$-$Leu^9$-$Cys^{10}$]-$Asp^{11}$)-$Nle^{12}$-$Leu^{13}$-$NH_2$ Ac-c[$Cys^1$-$Pro^2$-$Ser^3$-$Arg^4$-$Leu^5$-$Pro^6$-c($Lys^7$-$Arg^8$-$Leu^9$-$Cys^{10}$]-$Asp^{11}$)-$Nle^{12}$-$Leu^{13}$-$NH_2$ -continued Ac-c[$Cys^1$-$Pro^2$-$Pro^3$-$Arg^4$-$Leu^5$-$Pro^6$-c($Orn^7$-$Arg^8$-$Leu^9$-$Cys^{10}$]-$Glu^{11}$)-$Nle^{12}$-$Leu^{13}$-$NH_2$ Ac-c[$Cys^1$-$Pro^2$-$Ser^3$-$Arg^4$-$Leu^5$-$Pro^6$-c($Orn^7$-$Arg^8$-$Leu^9$-$Cys^{10}$]-$Glu^{11}$)-$Nle^{12}$-$Leu^{13}$-$NH_2$ Ac-c[$Cys^1$-$Pro^2$-$Pro^3$-$Arg^4$-$Leu^5$-$Pro^6$-c($Asp^7$-$Arg^8$-$Leu^9$-$Cys^{10}$]-$Lys^{11}$)-$Nle^{12}$-$Leu^{13}$-$NH_2$ Ac-c[$Cys^1$-$Pro^2$-$Ser^3$-$Arg^4$-$Leu^5$-$Pro^6$-c($Asp^7$-$Arg^8$-$Leu^9$-$Cys^{10}$]-$Lys^{11}$)-$Nle^{12}$-$Leu^{13}$-$NH_2$ Ac-c[$Cys^1$-$Pro^2$-$Pro^3$-$Arg^4$-$Leu^5$-$Pro^6$-c($Glu^7$-$Arg^8$-$Leu^9$-$Cys^{10}$]-$Orn^{11}$)-$Nle^{12}$-$Leu^{13}$-$NH_2$ Ac-c[$Cys^1$-$Pro^2$-$Ser^3$-$Arg^4$-$Leu^5$-$Pro^6$-c($Glu^7$-$Arg^8$-$Leu^9$-$Cys^{10}$]-$Orn^{11}$)-$Nle^{12}$-$Leu^{13}$-$NH_2$ Ac-c[$Cys^1$-$Pro^2$-$Pro^3$-$Arg^4$-$Leu^5$-$Pro^6$-c($Lys^7$-$Pro^8$-$Leu^9$-$Cys^{10}$]-$Asp^{11}$)-$Leu^{12}$-$Ile^{13}$-$NH_2$ Ac-c[$Cys^1$-$Pro^2$-$Ser^3$-$Arg^4$-$Leu^5$-$Pro^6$-c($Lys^7$-$Pro^8$-$Leu^9$-$Cys^{10}$]-$Asp^{11}$)-$Leu^{12}$-$Ile^{13}$-$NH_2$ Ac-c[$Cys^1$-$Pro^2$-$Pro^3$-$Arg^4$-$Leu^5$-$Pro^6$-c($Orn^7$-$Pro^8$-$Leu^9$-$Cys^{10}$]-$Glu^{11}$)-$Leu^{12}$-$Ile^{13}$-$NH_2$ Ac-c[$Cys^1$-$Pro^2$-$Ser^3$-$Arg^4$-$Leu^5$-$Pro^6$-c($Orn^7$-$Pro^8$-$Leu^9$-$Cys^{10}$]-$Glu^{11}$)-$Leu^{12}$-$Ile^{13}$-$NH_2$ Ac-c[$Cys^1$-$Pro^2$-$Pro^3$-$Arg^4$-$Leu^5$-$Pro^6$-c($Asp^7$-$Pro^8$-$Leu^9$-$Cys^{10}$]-$Lys^{11}$)-$Leu^{12}$-$Ile^{13}$-$NH_2$ Ac-c[$Cys^1$-$Pro^2$-$Ser^3$-$Arg^4$-$Leu^5$-$Pro^6$-c($Asp^7$-$Pro^8$-$Leu^9$-$Cys^{10}$]-$Lys^{11}$)-$Leu^{12}$-$Ile^{13}$-$NH_2$ Ac-c[$Cys^1$-$Pro^2$-$Pro^3$-$Arg^4$-$Leu^5$-$Pro^6$-c($Glu^7$-$Pro^8$-$Leu^9$-$Cys^{10}$]-$Orn^{11}$)-$Leu^{12}$-$Ile^{13}$-$NH_2$ Ac-c[$Cys^1$-$Pro^2$-$Ser^3$-$Arg^4$-$Leu^5$-$Pro^6$-c($Glu^7$-$Pro^8$-$Leu^9$-$Cys^{10}$]-$Orn^{11}$)-$Leu^{12}$-$Ile^{13}$-$NH_2$ Ac-c[$Cys^1$-$Pro^2$-$Pro^3$-$Arg^4$-$Leu^5$-$Pro^6$-c($Lys^7$-$Pro^8$-$Leu^9$-$Cys^{10}$]-$Asp^{11}$)-$Leu^{12}$-$Leu^{13}$-$NH_2$ Ac-c[$Cys^1$-$Pro^2$-$Ser^3$-$Arg^4$-$Leu^5$-$Pro^6$-c($Lys^7$-$Pro^8$-$Leu^9$-$Cys^{10}$]-$Asp^{11}$)-$Leu^{12}$-$Leu^{13}$-$NH_2$ Ac-c[$Cys^1$-$Pro^2$-$Pro^3$-$Arg^4$-$Leu^5$-$Pro^6$-c($Orn^7$-$Pro^8$-$Leu^9$-$Cys^{10}$]-$Glu^{11}$)-$Leu^{12}$-$Leu^{13}$-$NH_2$ Ac-c[$Cys^1$-$Pro^2$-$Ser^3$-$Arg^4$-$Leu^5$-$Pro^6$-c($Orn^7$-$Pro^8$-$Leu^9$-$Cys^{10}$]-$Glu^{11}$)-$Leu^{12}$-$Leu^{13}$-$NH_2$ Ac-c[$Cys^1$-$Pro^2$-$Pro^3$-$Arg^4$-$Leu^5$-$Pro^6$-c($Asp^7$-$Pro^8$-$Leu^9$-$Cys^{10}$]-$Lys^{11}$)-$Leu^{12}$-$Leu^{13}$-$NH_2$ Ac-c[$Cys^1$-$Pro^2$-$Ser^3$-$Arg^4$-$Leu^5$-$Pro^6$-c($Asp^7$-$Pro^8$-$Leu^9$-$Cys^{10}$]-$Lys^{11}$)-$Leu^{12}$-$Leu^{13}$-$NH_2$ Ac-c[$Cys^1$-$Pro^2$-$Pro^3$-$Arg^4$-$Leu^5$-$Pro^6$-c($Glu^7$-$Pro^8$-$Leu^9$-$Cys^{10}$]-$Orn^{11}$)-$Leu^{12}$-$Leu^{13}$-$NH_2$ Ac-c[$Cys^1$-$Pro^2$-$Ser^3$-$Arg^4$-$Leu^5$-$Pro^6$-c($Glu^7$-$Pro^8$-$Leu^9$-$Cys^{10}$]-$Orn^{11}$)-$Leu^{12}$-$Leu^{13}$-$NH_2$ Ac-c[$Cys^1$-$Pro^2$-$Pro^3$-$Arg^4$-$Leu^5$-$Pro^6$-c($Lys^7$-$Pro^8$-$Leu^9$-$Cys^{10}$]-$Asp^{11}$)-$Nle^{12}$-$Ile^{13}$-$NH_2$ Ac-c[$Cys^1$-$Pro^2$-$Ser^3$-$Arg^4$-$Leu^5$-$Pro^6$-c($Lys^7$-$Pro^8$-$Leu^9$-$Cys^{10}$]-$Asp^{11}$)-$Nle^{12}$-$Ile^{13}$-$NH_2$ Ac-c[$Cys^1$-$Pro^2$-$Pro^3$-$Arg^4$-$Leu^5$-$Pro^6$-c($Orn^7$-$Pro^8$-$Leu^9$-$Cys^{10}$]-$Glu^{11}$)-$Nle^{12}$-$Ile^{13}$-$NH_2$ Ac-c[$Cys^1$-$Pro^2$-$Ser^3$-$Arg^4$-$Leu^5$-$Pro^6$-c($Orn^7$-$Pro^8$-$Leu^9$-$Cys^{10}$]-$Glu^{11}$)-$Nle^{12}$-$Ile^{13}$-$NH_2$ Ac-c[$Cys^1$-$Pro^2$-$Pro^3$-$Arg^4$-$Leu^5$-$Pro^6$-c($Asp^7$-$Pro^8$-$Leu^9$-$Cys^{10}$]-$Lys^{11}$)-$Nle^{12}$-$Ile^{13}$-$NH_2$ -continued Ac-c[Cys$^{1}$-Pro$^{2}$-Ser$^{3}$-Arg$^{4}$-Leu$^{5}$-Pro$^{6}$-c(Asp$^{7}$-Pro$^{8}$-Leu$^{9}$-Cys$^{10}$]-Lys$^{11}$)-Nle$^{12}$-Ile$^{13}$-$NH_2$ Ac-c[Cys$^{1}$-Pro$^{2}$-Pro$^{3}$-Arg$^{4}$-Leu$^{5}$-Pro$^{6}$-c(Glu$^{7}$-Pro$^{8}$-Leu$^{9}$-Cys$^{10}$]-Orn$^{11}$)-Nle$^{12}$-Ile$^{13}$-$NH_2$ Ac-c[Cys$^{1}$-Pro$^{2}$-Ser$^{3}$-Arg$^{4}$-Leu$^{5}$-Pro$^{6}$-c(Glu$^{7}$-Pro$^{8}$-Leu$^{9}$-Cys$^{10}$]-Orn$^{11}$)-Nle$^{12}$-Ile$^{13}$-$NH_2$ Ac-c[Cys$^{1}$-Pro$^{2}$-Pro$^{3}$-Arg$^{4}$-Leu$^{5}$-Pro$^{6}$-c(Lys$^{7}$-Pro$^{8}$-Leu$^{9}$-Cys$^{10}$]-Asp$^{11}$)-Nle$^{12}$-Leu$^{13}$-$NH_2$ Ac-c[Cys$^{1}$-Pro$^{2}$-Ser$^{3}$-Arg$^{4}$-Leu$^{5}$-Pro$^{6}$-c(Lys$^{7}$-Pro$^{8}$-Leu$^{9}$-Cys$^{10}$]-Asp$^{11}$)-Nle$^{12}$-Leu$^{13}$-$NH_2$ Ac-c[Cys$^{1}$-Pro$^{2}$-Pro$^{3}$-Arg$^{4}$-Leu$^{5}$-Pro$^{6}$-c(Orn$^{7}$-Pro$^{8}$-Leu$^{9}$-Cys$^{10}$]-Glu$^{11}$)-Nle$^{12}$-Leu$^{13}$-$NH_2$ Ac-c[Cys$^{1}$-Pro$^{2}$-Ser$^{3}$-Arg$^{4}$-Leu$^{5}$-Pro$^{6}$-c(Orn$^{7}$-Pro$^{8}$-Leu$^{9}$-Cys$^{10}$]-Glu$^{11}$)-Nle$^{12}$-Leu$^{13}$-$NH_2$ Ac-c[Cys$^{1}$-Pro$^{2}$-Pro$^{3}$-Arg$^{4}$-Leu$^{5}$-Pro$^{6}$-c(Asp$^{7}$-Pro$^{8}$-Leu$^{9}$-Cys$^{10}$]-Lys$^{11}$)-Nle$^{12}$-Leu$^{13}$-$NH_2$ Ac-c[Cys$^{1}$-Pro$^{2}$-Ser$^{3}$-Arg$^{4}$-Leu$^{5}$-Pro$^{6}$-c(Asp$^{7}$-Pro$^{8}$-Leu$^{9}$-Cys$^{10}$]-Lys$^{11}$)-Nle$^{12}$-Leu$^{13}$-$NH_2$ Ac-c[Cys$^{1}$-Pro$^{2}$-Pro$^{3}$-Arg$^{4}$-Leu$^{5}$-Pro$^{6}$-c(Glu$^{7}$-Pro$^{8}$-Leu$^{9}$-Cys$^{10}$]-Orn$^{11}$)-Nle$^{12}$-Leu$^{13}$-$NH_2$ Ac-c[Cys$^{1}$-Pro$^{2}$-Ser$^{3}$-Arg$^{4}$-Leu$^{5}$-Pro$^{6}$-c(Glu$^{7}$-Pro$^{8}$-Leu$^{9}$-Cys$^{10}$]-Orn$^{11}$)-Nle$^{12}$-Leu$^{13}$-$NH_2$ Ac-c[Cys$^{1}$-Pro$^{2}$-Pro$^{3}$-Tyr$^{4}$-Leu$^{5}$-Pro$^{6}$-C(Lys$^{7}$-Tyr$^{8}$-Leu$^{9}$-Cys$^{10}$]-Glu$^{11}$)-Leu$^{12}$-Ile$^{13}$-$NH_2$ Ac-c[Cys$^{1}$-Pro$^{2}$-Pro$^{3}$-Tyr$^{4}$-Leu$^{5}$-Pro$^{6}$-c(Lys$^{7}$-Tyr$^{8}$-Leu$^{9}$-Cys$^{10}$]-Glu$^{11}$)-Leu$^{12}$-Leu$^{13}$-$NH_2$ Ac-c[Cys$^{1}$-Pro$^{2}$-Pro$^{3}$-Tyr$^{4}$-Leu$^{5}$-Pro$^{6}$-c(Lys$^{7}$-Tyr$^{8}$-Leu$^{9}$-Cys$^{10}$]-Glu$^{11}$)-Nle$^{12}$-Ile$^{13}$-$NH_2$ Ac-c[Cys$^{1}$-Pro$^{2}$-Pro$^{3}$-Tyr$^{4}$-Leu$^{5}$-Pro$^{6}$-c(Lys$^{7}$-Tyr$^{8}$-Leu$^{9}$-Cys$^{10}$]-Glu$^{11}$)-Nle$^{12}$-Leu$^{13}$-$NH_2$ Ac-c[Cys$^{1}$-Pro$^{2}$-Ser$^{3}$-Tyr$^{4}$-Leu$^{5}$-Pro$^{6}$-c(Lys$^{7}$-Tyr$^{8}$-Leu$^{9}$-Cys$^{10}$]-Glu$^{11}$)-Leu$^{12}$-Ile$^{13}$-$NH_2$ Ac-c[Cys$^{1}$-Pro$^{2}$-Ser$^{3}$-Tyr$^{4}$-Leu$^{5}$-Pro$^{6}$-c(Lys$^{7}$-Tyr$^{8}$-Leu$^{9}$-Cys$^{10}$]-Glu$^{11}$)-Leu$^{12}$-Leu$^{13}$-$NH_2$ Ac-c[Cys$^{1}$-Pro$^{2}$-Ser$^{3}$-Tyr$^{4}$-Leu$^{5}$-Pro$^{6}$-c(Lys$^{7}$-Tyr$^{8}$-Leu$^{9}$-Cys$^{10}$]-Glu$^{11}$)-Nle$^{12}$-Ile$^{13}$-$NH_2$ Ac-c[Cys$^{1}$-Pro$^{2}$-Ser$^{3}$-Tyr$^{4}$-Leu$^{5}$-Pro$^{6}$-c(Lys$^{7}$-Tyr$^{8}$-Leu$^{9}$-Cys$^{10}$]-Glu$^{11}$)-Nle$^{12}$-Leu$^{13}$-$NH_2$ Ac-c[Cys$^{1}$-Pro$^{2}$-Pro$^{3}$-Tyr$^{4}$-Leu$^{5}$-Pro$^{6}$-c(Lys$^{7}$-Arg$^{8}$-Leu$^{9}$-Cys$^{10}$]-Glu$^{11}$)-Leu$^{12}$-Ile$^{13}$-$NH_2$ Ac-c[Cys$^{1}$-Pro$^{2}$-Pro$^{3}$-Tyr$^{4}$-Leu$^{5}$-Pro$^{6}$-c(Lys$^{7}$-Arg$^{8}$-Leu$^{9}$-Cys$^{10}$]-Glu$^{11}$)-Leu$^{12}$-Leu$^{13}$-$NH_2$ Ac-c[Cys$^{1}$-Pro$^{2}$-Pro$^{3}$-Tyr$^{4}$-Leu$^{5}$-Pro$^{6}$-c(Lys$^{7}$-Arg$^{8}$-Leu$^{9}$-Cys$^{10}$]-Glu$^{11}$)-Nle$^{12}$-Ile$^{13}$-$NH_2$ Ac-c[Cys$^{1}$-Pro$^{2}$-Pro$^{3}$-Tyr$^{4}$-Leu$^{5}$-Pro$^{6}$-c(Lys$^{7}$-Arg$^{8}$-Leu$^{9}$-Cys$^{10}$]-Glu$^{11}$)-Nle$^{12}$-Leu$^{13}$-$NH_2$ Ac-c[Cys$^{1}$-Pro$^{2}$-Ser$^{3}$-Tyr$^{4}$-Leu$^{5}$-Pro$^{6}$-c(Lys$^{7}$-Arg$^{8}$-Leu$^{9}$-Cys$^{10}$]-Glu$^{11}$)-Leu$^{12}$-Ile$^{13}$-$NH_2$ Ac-c[Cys$^{1}$-Pro$^{2}$-Ser$^{3}$-Tyr$^{4}$-Leu$^{5}$-Pro$^{6}$-C(Lys$^{7}$-Arg$^{8}$-Leu$^{9}$-Cys$^{10}$]-Glu$^{11}$)-Leu$^{12}$-Leu$^{13}$-$NH_2$ Ac-c[Cys$^{1}$-Pro$^{2}$-Ser$^{3}$-Tyr$^{4}$-Leu$^{5}$-Pro$^{6}$-c(Lys$^{7}$-Arg$^{8}$-Leu$^{9}$-Cys$^{10}$]-Glu$^{11}$)-Nle$^{12}$-Ile$^{13}$-$NH_2$ Ac-c[Cys$^{1}$-Pro$^{2}$-Ser$^{3}$-Tyr$^{4}$-Leu$^{5}$-Pro$^{6}$-c(Lys$^{7}$-Arg$^{8}$-Leu$^{9}$-Cys$^{10}$]-Glu$^{11}$)-Nle$^{12}$-Leu$^{13}$-$NH_2$ -continued Ac-c[Cys$^{1}$-Pro$^{2}$-Pro$^{3}$-Tyr$^{4}$-Leu$^{5}$-Pro$^{6}$-c(Lys$^{7}$-Pro$^{8}$-Leu$^{9}$-Cys$^{10}$]-Glu$^{11}$)-Leu$^{12}$-Ile$^{13}$-NH$_2$ Ac-c[Cys$^{1}$-Pro$^{2}$-Pro$^{3}$-Tyr$^{4}$-Leu$^{5}$-Pro$^{6}$-c(Lys$^{7}$-Pro$^{8}$-Leu$^{9}$-Cys$^{10}$]-Glu$^{11}$)-Leu$^{12}$-Leu$^{13}$-NH$_2$ Ac-c[Cys$^{1}$-Pro$^{2}$-Pro$^{3}$-Tyr$^{4}$-Leu$^{5}$-Pro$^{6}$-c(Lys$^{7}$-Pro$^{8}$-Leu$^{9}$-Cys$^{10}$]-Glu$^{11}$)-Nle$^{12}$-Ile$^{13}$-NH$_2$ Ac-c[Cys$^{1}$-Pro$^{2}$-Pro$^{3}$-Tyr$^{4}$-Leu$^{5}$-Pro$^{6}$-c(Lys$^{7}$-Pro$^{8}$-Leu$^{9}$-Cys$^{10}$]-Glu$^{11}$)-Nle$^{12}$-Leu$^{13}$-NH$_2$ Ac-c[Cys$^{1}$-Pro$^{2}$-Ser$^{3}$-Tyr$^{4}$-Leu$^{5}$-Pro$^{6}$-c(Lys$^{7}$-Pro$^{8}$-Leu$^{9}$-Cys$^{10}$]-Glu$^{11}$)-Leu$^{12}$-Ile$^{13}$-NH$_2$ Ac-c[Cys$^{1}$-Pro$^{2}$-Ser$^{3}$-Tyr$^{4}$-Leu$^{5}$-Pro$^{6}$-c(Lys$^{7}$-Pro$^{8}$-Leu$^{9}$-Cys$^{10}$]-Glu$^{11}$)-Leu$^{12}$-Leu$^{13}$-NH$_2$ Ac-c[Cys$^{1}$-Pro$^{2}$-Ser$^{3}$-Tyr$^{4}$-Leu$^{5}$-Pro$^{6}$-c(Lys$^{7}$-Pro$^{8}$-Leu$^{9}$-Cys$^{10}$]-Glu$^{11}$)-Nle$^{12}$-Ile$^{13}$-NH$_2$ Ac-c[Cys$^{1}$-Pro$^{2}$-Ser$^{3}$-Tyr$^{4}$-Leu$^{5}$-Pro$^{6}$-c(Lys$^{7}$-Pro$^{8}$-Leu$^{9}$-Cys$^{10}$]-Glu$^{11}$)-Nle$^{12}$-Leu$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Tyr$^{8}$-Leu$^{9}$-Cys$^{10}$]-Lys$^{11}$)-Leu$^{12}$-Ile$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Tyr$^{8}$-Leu$^{9}$-Cys$^{10}$]-Lys$^{11}$)-Leu$^{12}$-Leu$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Tyr$^{8}$-Leu$^{9}$-Cys$^{10}$]-Lys$^{11}$)-Nle$^{12}$-Ile$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Tyr$^{8}$-Leu$^{9}$-Cys$^{10}$]-Lys$^{11}$)-Nle$^{12}$-Leu$^{13}$-NH$_2$ Ac-c[Cys$^{1}$-Pro$^{2}$-Ser$^{3}$-Tyr$^{4}$-Leu$^{5}$-Pro$^{6}$-c(Glu$^{7}$-Tyr$^{8}$-Leu$^{9}$-Cys$^{10}$]-Lys$^{11}$)-Leu$^{12}$-Ile$^{13}$-NH$_2$ Ac-c[Cys$^{1}$-Pro$^{2}$-Ser$^{3}$-Tyr$^{4}$-Leu$^{5}$-Pro$^{6}$-c(Glu$^{7}$-Tyr$^{8}$-Leu$^{9}$-Cys$^{10}$]-Lys$^{11}$)-Leu$^{12}$-Leu$^{13}$-NH$_2$ Ac-c[Cys$^{1}$-Pro$^{2}$-Ser$^{3}$-Tyr$^{4}$-Leu$^{5}$-Pro$^{6}$-c(Glu$^{7}$-Tyr$^{8}$-Leu$^{9}$-Cys$^{10}$]-Lys$^{11}$)-Nle$^{12}$-Ile$^{13}$-NH$_2$ Ac-c[Cys$^{1}$-Pro$^{2}$-Ser$^{3}$-Tyr$^{4}$-Leu$^{5}$-Pro$^{6}$-c(Glu$^{7}$-Tyr$^{8}$-Leu$^{9}$-Cys$^{10}$]-Lys$^{11}$)-Nle$^{12}$-Leu$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Arg$^{8}$-Leu$^{9}$-Cys$^{10}$]-Lys$^{11}$)-Leu$^{12}$-Ile$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Arg$^{8}$-Leu$^{9}$-Cys$^{10}$]-Lys$^{11}$)-Leu$^{12}$-Leu$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Arg$^{8}$-Leu$^{9}$-Cys$^{10}$]-Lys$^{11}$)-Nle$^{12}$-Ile$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Arg$^{8}$-Leu$^{9}$-Cys$^{10}$]-Lys$^{11}$)-Nle$^{12}$-Leu$^{13}$-NH$_2$ Ac-c[Cys$^{1}$-Pro$^{2}$-Ser$^{3}$-Tyr$^{4}$-Leu$^{5}$-Pro$^{6}$-c(Glu$^{7}$-Arg$^{8}$-Leu$^{9}$-Cys$^{10}$]-Lys$^{11}$)-Leu$^{12}$-Ile$^{13}$-NH$_2$ Ac-c[Cys$^{1}$-Pro$^{2}$-Ser$^{3}$-Tyr$^{4}$-Leu$^{5}$-Pro$^{6}$-c(Glu$^{7}$-Arg$^{8}$-Leu$^{9}$-Cys$^{10}$]-Lys$^{11}$)-Leu$^{12}$-Leu$^{13}$-NH$_2$ Ac-c[Cys$^{1}$-Pro$^{2}$-Ser$^{3}$-Tyr$^{4}$-Leu$^{5}$-Pro$^{6}$-c(Glu$^{7}$-Arg$^{8}$-Leu$^{9}$-Cys$^{10}$]-Lys$^{11}$)-Nle$^{12}$-Ile$^{13}$-NH$_2$ Ac-c[Cys$^{1}$-Pro$^{2}$-Ser$^{3}$-Tyr$^{4}$-Leu$^{5}$-Pro$^{6}$-c(Glu$^{7}$-Arg$^{8}$-Leu$^{9}$-Cys$^{10}$]-Lys$^{11}$)-Nle$^{12}$-Leu$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Pro$^{8}$-Leu$^{9}$-Cys$^{10}$]-Lys$^{11}$)-Leu$^{12}$-Ile$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Pro$^{8}$-Leu$^{9}$-Cys$^{10}$]-Lys$^{11}$)-Leu$^{12}$-Leu$^{13}$-NH$_2$ Ac-c[Cys$^{1}$-Pro$^{2}$-Pro$^{3}$-Tyr$^{4}$-Leu$^{5}$-Pro$^{6}$-c(Glu$^{7}$-Pro$^{8}$-Leu$^{9}$-Cys$^{10}$]-Lys$^{11}$)-Nle$^{12}$-Ile$^{13}$-NH$_2$ -continued Ac-c[$Cys^1$-$Pro^2$-$Pro^3$-$Tyr^4$-$Leu^5$-$Pro^6$-c($Glu^7$-$Pro^8$-$Leu^9$-$Cys^{10}$]-$Lys^{11}$)-$Nle^{12}$-$Leu^{13}$-$NH_2$ Ac-c[$Cys^1$-$Pro^2$-$Ser^3$-$Tyr^4$-$Leu^5$-$Pro^6$-c($Glu^7$-$Pro^8$-$Leu^9$-$Cys^{10}$]-$Lys^{11}$)-$Leu^{12}$-$Ile^{13}$-$NH_2$ Ac-c[$Cys^1$-$Pro^2$-$Ser^3$-$Tyr^4$-$Leu^5$-$Pro^6$-c($Glu^7$-$Pro^8$-$Leu^9$-$Cys^{10}$]-$Lys^{11}$)-$Leu^{12}$-$Leu^{13}$-$NH_2$ Ac-c[$Cys^1$-$Pro^2$-$Ser^3$-$Tyr^4$-$Leu^5$-$Pro^6$-c($Glu^7$-$Pro^8$-$Leu^9$-$Cys^{10}$]-$Lys^{11}$)-$Nle^{12}$-$Ile^{13}$-$NH_2$ Ac-c[$Cys^1$-$Pro^2$-$Ser^3$-$Tyr^4$-$Leu^5$-$Pro^6$-c($Glu^7$-$Pro^8$-$Leu^9$-$Cys^{10}$]-$Lys^{11}$)-$Nle^{12}$-$Leu^{13}$-$NH_2$ The peptides of the embodiments include homologous peptides in which one to several amino acids are deleted, added and/or substituted in the amino acid sequences represented in [1] to [17] above, provided that they have binding activity to VIPR2. When the phrase, "peptides in which one to several amino acids are deleted, added and/or substituted" is used herein, the number of those amino acids is not particularly limited as long as the peptide has VIPR2 binding activity, but preferably from 1 to 5, more preferably 1 or 2. The deletion, addition, and/or substitution may be at the end or in the middle of the peptide, and may be in one or more locations.

In one aspect, as an amino acid sequence in which one to several amino acids are deleted, added, and/or substituted in the above amino acid sequence, such an amino acid sequence is exemplified as those having at least 50%, preferably 70%, even more preferably 80%, and especially preferably 90% or more identity with the amino acid sequence, upon calculation using BLAST (Basic Local Alignment Search Tool at the National Center for Biological Information) or the like (e.g., using default parameters).

It is also known that there are peptides and protein domains with highly similar three-dimensional structures, even if the homology in the primary structure is low. Therefore, peptides having at least 50%, preferably 70%, even more preferably 80%, and especially preferably 90% or more three-dimensional structure homology with the above amino acid sequence and having VIPR2 binding activity are also included in this embodiment. The homology of the three-dimensional structures of peptides can be predicted as follows from the amino acid sequence of a peptide having an unknown three-dimensional structure by using a homology modeling method or the like. For example, when an arbitrary amino acid sequence (target sequence) having a sequence similar to the cyclic peptide of the present embodiment (reference peptide) is given, an alignment (sequence juxtaposition) between the target sequence and the reference sequence is given. Using the alignment calculated by FASTA, PSI-BLAST, LIBRA, etc., the correspondence relationship for each amino acid between the target sequence and the reference sequence can be determined, and based on this relationship, the 3D coordinates for each amino acid on the target sequence are created from the 3D coordinates of the reference peptide. In the construction of the 3D coordinates, there may be structurally inappropriate gaps, collisions, or distortions between amino acid residues, so these structural distortions are resolved by energy minimization calculations. In some modeling software, the structural distortions are resolved in stages rather than simultaneously for all atoms of the peptide. In other words, the alpha carbon atoms that form the backbone of the peptide are first processed, followed by the main chain atoms that contain the alpha carbon atoms, and finally the entire peptide including the side chain atoms. Once the alignment to the target sequence is obtained in this way, the 3D structure can be predicted and constructed. The 3D structure homology index can be compared using RMSD (Root Mean Square Deviation), which is the difference between the XYZ coordinates when they are optimally superimposed.

The peptides of the embodiments also include various derivatives and/or modifications thereof, as long as they solve the aforementioned problem. Such derivatives include but are not limited to those in which the saturated fatty chain of the peptide is replaced by an unsaturated fatty chain; some atoms of the peptide are replaced with other atoms including radioactive or non-radioactive isotope atoms; the amide bond of the peptide is replaced by a thioamide bond (—NH—C(═S)—); the amide bond of the peptide is replaced with an alkene (—C═C—), the amide bond of the peptide is replaced with alkyl (—C—C—); the amide bond of the peptide is replaced with a hydroxyethylene (—C(—OH)—C—); the amide bond of the peptide is replaced with an ester (—O—C(═O)—); the amide bond of the peptide is replaced with an alkene (—C═C—), the amide bond of peptide is replaced with (—C—NH—); or the amide bond of the peptide is replaced with (—C(═O)—C—), and the like. The above modifications include but are not limited to those in which the α-carbon of the peptide is disubstituted; the amide bond of the peptide is N-alkylated; some of the functional groups of the peptide are modified by halogenation, cyanation, nitration, oxoation, hydroxylation, amination, deamination, dehydration, amidation, acetylation, methoxylation, prenylation, alkylation, and the like (for example, some of the amino groups of the peptide are acetylated, formylated, myristoylated, palmitoylated, pyroglutamate, alkylation or deamination; some carboxylic groups of the peptide are N-pyrrolidinylated or N-piperidinylated, amidated (amide, methylamide, ethylamide, p-nitroanilide, β-naphthylamide, and the like) or esters (methyl ester, ethyl ester, thioester, and the like), those in which the S of the peptide is sulfoxide S(═O) or sulfone $S(=O)_2$; peptides are multimerized via chemical linkers, peptides are biotin-labeled, peptides are fluorescence-labeled, peptides are luminescent-labeled, as well as fused peptide with alkyl chains, polyethylene glycols, antibodies, lectins, sugar chains, enzymes, membrane-permeable peptides, low molecular-weight compounds, or molecules that induce ubiquitination of proteins and the like.

The peptides of the embodiments also encompass salts of the peptide. The salts of the peptides can be salts with physiologically acceptable bases or acids, and for example, an addition salt of an inorganic acid (hydrochloric acid, hydrobromic acid, hydroiodic acid, sulfuric acid, phosphoric acid, and the like), addition salts of organic acids (p-toluene sulfonic acid, methane sulfonic acid, oxalic acid, p-bromophenyl sulfonic acid, carboxylic acid, succinic acid, citric acid, benzoic acid, acetic acid, and the like), an addition salt of inorganic bases (ammonium hydroxide or alkali, alkaline earth metal hydroxides, carbonates, bicarbonates, and the like), an addition salt of amino acids or the like.

The peptides of the embodiments may also be prodrugs. A prodrug is a compound that is converted to the inventive peptide by an enzymatic reaction or gastric acid under physiological conditions in vivo, i.e., a compound that is enzymatically oxidized, reduced, or hydrolyzed to the peptide embodiments, or a compound that is hydrolyzed by gastric acid or the like to the peptide of the embodiments.

Examples of the prodrug of the peptide of the embodiments include but are not limited to compounds in which the amino group of the peptide of the embodiments is acylated, alkylated or phosphorylated (for example, compounds in which the amino group of the peptide of the embodiments is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated; compounds in which the hydroxy group of the peptide of the embodiments is acylated, alkylated, phosphorylated, or borylated (e.g., compounds in which the hydroxy group of the peptide of the embodiments is acetylated, palmitoylated, propanoylated, pivaloylated, succinylated, fumarylated, alanylated, or dimethylaminomethylcarbonylated); compounds in which the hydroxy or carboxy groups of the peptides of the embodiments are esterified or amidated (e.g., compounds in which the hydroxy or carboxy groups of the peptides of the embodiments are $C_{1-6}$ alkyl esterified, phenyl esterified, carboxymethyl esterified dimethylaminomethyl esterified, pivaloyloxy methyl esterified, ethoxycarbonyloxy ethyl esterified, phthalidyl esterified, (5-methyl-2-oxo-1,3-dioxolen-4-yl)methylesterified, cyclohexyloxycarbonylethyl esterified, or methylamidated). These compounds can be produced from the peptides of the embodiments by methods known to themselves.

Prodrugs of the inventive peptides may be those transformed into the inventive peptide under physiological conditions as described in Hirokawa Shoten 1990, "Development of Pharmaceuticals", Volume 7, Molecular Design pp. 163-198.

In this specification, prodrugs may form salts, such salts being those exemplified as salts of the peptides of the embodiments.

The peptide may be crystalline, and the peptide is included in the inventive peptide whether in a single crystalline form or in a mixture of crystalline forms. Crystals can be produced by crystallization by applying crystallization methods known per se.

The peptides may be pharmaceutically acceptable co-crystals or co-crystal salts. Co-crystal or co-crystal salt means a crystalline substance composed of two or more unique solids at room temperature, each having different physical properties (e.g., structure, melting point, heat of melting, hygroscopicity, solubility, and stability). Co-crystals or co-crystalline salts can be produced according to co-crystallization methods known per se.

Action and Effect of Cyclic Peptides

As shown in the following Examples, Seq-1 to Seq-10, which are representative examples of the amino acid sequence group of this embodiment, show binding activity to VIPR2-expressing cells, and Seq-1, 6, 9 and 10 have antagonist activity against VIPR2-expressing cells and resistance to protease degradation. The amino acid sequence group described in this embodiment have similar amino acid sequences and structural features to Seq-1 to 10, it is highly likely that they also possess resistance to protease degradation, VIPR2 binding activity and VIPR2 antagonist activity.

The VIPR2 binding activity of the peptides shown in the examples below, indicates the following: (1) C-terminal three residues of VIpep-3 (amino acid residues 14-16: Leu-Arg-Ser) can be deleted without loss of binding activity to VIPR2. (2) VIPR2 binding activity of the peptide is improved by cross-linking at positions 7 and 11. (3) VIpep-3 is cyclized by the S—S bond formed between the cysteine residues at positions 1 and 10. However, the cyclization for VIPR2 binding activity is not limited to the linkage between positions 1 and 10, but can be replaced by the linkage between positions 2 and 10 or positions 3 and 10, by introducing amino acid residues with long side chains at positions 2 and 3 and directly cross-linking to position 10, or indirectly cross-linking them by using linkers of different lengths and structures, in order to bring the interatomic distance between positions 2 and 10 or positions 3 and 10 closer to the interatomic distance between positions 1 and 10. (4) Bicyclic peptides between three amino acid residues also exhibit VIPR2 binding activity, in that the acceptable cross-linking pattern may be any of the combinations 1-7-10, 2-7-10, and 3-7-10. The above (3) and (4) will be explained in more detail. As shown in the examples described below, the cyclic structure formed between the first to 3rd amino acid residue and 10th amino acid residue of VIpep-3: $C\alpha^3—NH—C(=O)—C\alpha^2—NH—C(=O)—C\alpha^1—CH_2—S—S—CH_2—C\alpha^{10}$ can be replaced with, for example, the cyclic structure formed between the 3rd amino acid residue with the side chain of non-natural structure and the 10th amino acid residue: $C\alpha^3—CH_2—CH_2—CH_2—CH_2—CH_2—CH_2—CH_2—S—CH_2—CH_2—C\alpha^{10}$. In other words, the first three amino acid residues of VIpep-3 are not significantly involved in VIPR2 binding activity, suggesting that the ring size regulation of the peptide of the embodiments is important for VIPR2 binding activity. The peptides can be cyclized not only between positions 1 and 10, but also between positions 2 and 10 and between positions 3 and 10, and as long as the ring size of the peptide is within a certain range, a wide range of other forms of chemical structures may be acceptable, such as an amide bond, a disulfide bond, a thioether bond, a C═C bond, a C—C bond, a bond via triazole, a bond via dithiotetrafluorobenzene. This property is also true for the linkage via position 7 (between positions 1-7-10, between positions 2-7-10, and between positions 3-7-10).

The amino acid sequences represented by [1] to [16] above have similar amino acid sequences and structural features to VIpep-3 that has antagonist activity against VIPR2 of human, mouse, and rat, it is highly likely that the amino acid sequences bind to and inhibit the function of VIPR2 in mammals other than humans, such as mice and rats.

Production Method for Cyclic Peptides

The peptides of this embodiment can be produced by known methods of peptide production, such as liquid-phase methods, solid-phase methods, or chemical synthesis methods such as hybrid methods combining liquid-phase and solid-phase methods.

For the solid phase method, commercially available automated synthesizers can be used. For example, an esterification reaction is performed between the hydroxyl group of a resin having a hydroxyl group and the carboxyl group of a primary amino acid (usually the C-terminal amino acid of the peptide of interest) whose α-amino group is protected by a protecting group such as the Fmoc group. As an esterification catalyst, known dehydration and condensation agents such as 1-mesitylenesulfonyl-3-nitro-1,2,4-triazole (MSNT), dicyclohexylcarbodiimide (DCC), and diisopropylcarbodiimide (DIPCDI) can be used. Next, the protecting group of the α-amino group of the first amino acid is deprotected and a second amino acid, in which all functional groups except the carboxy group of the main chain are protected, is added to activate the carboxy group and bind the first and second amino acids together. Furthermore, the α-amino group of the second amino acid is deprotected, and a third amino acid, in which all functional groups except the carboxy group of the main chain are protected, is added to activate the carboxy group, and the second and third amino acids are combined. This process is repeated to synthesize a peptide of the desired length. The linear peptide is cleaved from the resin, and after purification, the functional group for cyclizing the peptide is deprotected according to the standard method.

Solid-phase synthesis resins include Merrifield resin, MBHA resin, Cl-Trt resin, SASRIN resin, Wang resin, Rink amide resin, HMFS resin, Amino-PEGA resin (Merck), HMPA-PEGA resin (Merck) and the like. These resins may be washed with a solvent (dimethylformamide (DMF), 2-propanol, methylene chloride, etc.) before use. The protective group for the α-amino group includes a benzyloxycarbonyl (Cbz) group, a tert-butoxycarbonyl (Boc) group, a fluorenylmethoxycarbonyl (Fmoc) group, a benzyl group, an allyl group, an allyloxycarbonyl (Allloc) group and the like. The Cbz group can be deprotected by hydrofluoric acid, hydrogenation, and the like. The Boc group can be deprotected by trifluoroacetic acid (TFA), and the Fmoc group can be deprotected by treatment with piperidine. The α-carboxy group can be protected by methyl ester, ethyl ester, benzyl ester, tert-butyl ester, cyclohexyl ester, etc. Other functional groups of amino acids, such as hydroxy groups of serine and threonine can be protected by benzyl or tert-butyl groups, and hydroxy groups of tyrosine can be protected by 2-bromobenzyloxycarbonyl or tert-butyl groups. Side chain amino groups such as lysine, and carboxy groups such as glutamic acid and aspartic acid can be protected in the same way as alpha-amino groups and alpha-carboxy groups.

Activation of the carboxy group can be carried out using a condensing agent. Examples of condensing agents are dicyclohexylcarbodiimide (DCC), diisopropylcarbodiimide (DIPCDI), 1-ethyl-3-(3-dimethylaminopropyl) carbodiimide (EDC or WSC), (1H-benzotriazol-1-yloxy)tris(dimethylamino)phosphonium hexafluorophosphate (BOP) bis(dimethylamino)methyl]-1H-benzotriazolium-3-oxide hexafluorophosphate (HBTU), and the like. Cleavage of the peptide chain from the resin can be carried out by treatment with acids such as TFA and hydrogen fluoride (HF).

The peptide of this embodiment is cyclized in one aspect. In the present specification, cyclization means the covalent linkage of two or more amino acids separated by one or more amino acids within a peptide, either directly or indirectly via a linker to form one or more cyclic structure in the molecule. Cyclization can be performed in accordance with the methods described in Non-Patent Literature 9, Non-Patent Literature 10, and Non-Patent Literature 11. For example, an amide bond between an amino group and a carboxy group, a disulfide bond between a thiol group and a thiol group, a thioether bond between a thiol group and a halogen group, a thioether bond between a thiol group and an allyl group by thiol-ene reaction, a C═C bond by olefin metathesis reaction between an allyl group and an allyl groups (the C═C bond may be converted to a C—C bond by a reduction reaction) (The C═C bond may be converted to a C—C bond by a reduction reaction), a triazole-mediated bond by a click reaction between an alkynyl group and an azido group, a thioether bond between a linker with a halogen group and two thiol groups, and the like. Direct or indirect covalent bonds for cyclization via linkers can be main-chain-to-main-chain, main-chain-to-side-chain, side-chain-to-main-chain, or side-chain-to-side-chain.

For example, the following bonds (linkages) can be used for the cyclization of the peptides of one embodiment, (1) a disulfide bond formed between the thiol groups of cysteine, D-cysteine, homocysteine, and D-homocysteine with thiol groups as amino acids 1 and 2, respectively; (2) a thioester bond formed between amino acid 1 having a nucleophilic halogen atom (chloro, bromo, or iodo) (such as 3-chloroalanine) or a carboxylic acid having a halogen atom (chloro, bromo, or iodo) (e.g., 3-chloropropanoic acid) and amino acid 2 having a thiol group; (3) a thioether bond formed between amino acids 1 and 2 having a thiol group and a linker having a halogen atom (chloro, bromo, or iodo) as a nucleophilic group, (e.g., 1,3-diiodopropane, 1,4-diiodobutane, 1,5-diiodopentane, 1,5-diiodopropane, 1,5-diiodopentane, 1,6-diiodohexane, 1,2-bis(bromomethyl)benzene, 1,3-bis(bromomethyl)benzene, 1,4-bis(bromomethyl)benzene, and the like); (4) a triazole-mediated covalent bond formed by a click reaction between β-azido alanine with an azido group as amino acid 1, and 2-amino-5-hexinic acid with an alkynyl group as amino acid 2; (5) a thioether bond formed by a thiol-ene reaction between an amino acid with an allyl group (e.g., allylglycine, D-allylglycine, homoallylglycine, D-homoallylglycine, etc.), or a carboxylic acid with an allyl group (e.g., 3-butenic acid) as amino acid 1, and amino acid 2 with a thiol group; (6) a C═C bond formed by olefin metathesis reaction between allyl groups of amino acid 1 and amino acid 2, each having an allyl group or a carboxylic acid having an allyl group; (7) a C—C bond formed by reduction of the C═C bond formed by olefin metathesis reaction; (8) an amide bond between amino acid 1 having an amino group (e.g., 2,3-diaminopropanoic acid, 2,4-diaminobutanoic acid, ornithine, lysine, and their D-amino acids, etc.) and amino acid 2 having a carboxy group (e.g., aspartic acid, glutamic acid, their D-amino acids, etc.) or C-terminal carboxy group; (9) an amide bond between an N-terminal amino group (such as beta-alanine and gamma-aminobutyric acid) and an amino acid with a carboxy group. Either of these amino acids 1 or 2 can come to the N-terminal side. Furthermore, (10) a thioether bond can be formed between amino acid 1, amino acid 2, and amino acid 3 having a thiol group and a linker (e.g., 1,3,5-tris(bromomethyl)benzene) having a halogen atom (chloro, bromo, or iodo) as a nucleophilic group. Amino acid 1, amino acid 2, and amino acid 3 can either come on the N-terminal side.

Pharmaceuticals, Diagnostics and Research Reagents Containing Cyclic Peptides The pharmaceutical composition of the embodiments contains, as an active ingredient, the amino acid sequences described above, wherein the peptides bind to VIPR2, thereby inhibiting the binding of the natural ligand to VIPR2 and suppressing VIPR2-mediated signal transduction. The mode of administration of the above pharmaceutical compositions is not particularly limited and may be administered orally or parenterally. Parenteral administration includes, for example, transmucosal (nasal, oral, ocular, pulmonary, vaginal, or rectal), injection (intravenous, subcutaneous, intramuscular, etc.), and percutaneous administration. Peptides in pharmaceutical compositions can be modified in various ways in view of their metabolic and excretory properties. For example, alkyl chains, polyethylene glycol, or sugar chains can be added to the peptides to increase their residence time in the blood or decrease their antigenicity. In addition, emulsions prepared with biodegradable polymeric compounds such as polylactic acid and glycol (PLGA), porous hydroxyapatite, liposomes, surface-modified liposomes, unsaturated fatty acids Nanoparticles, nanospheres, etc. may be used as sustained release substrates and the peptides may be encapsulated in them. For transdermal administration, a weak electric current may be applied to the skin surface to penetrate the stratum corneum (iontophoresis method).

The above pharmaceutical compositions may be used as the active ingredients as they are, or they may be formulated by adding pharmaceutically acceptable carriers, excipients, additives, etc. Examples of dosage forms include liquids (e.g., injections), dispersants, suspensions, tablets, rounds, powders, suppositories, sprays, fine granules, granules, capsules, syrups, lozenges, inhalants, ointments, eye drops, nasal drops, ear drops, and poultice preparations. These formulations may be controlled release formulations (e.g., sustained release microcapsules), such as fast or sustained release formulations. Formulation can be carried out according to conventional methods using, for example, excipients, binders, disintegrants, lubricants, dissolving agents, dissolution aids, coloring agents, taste and odor correcting agents, stabilizers, emulsifiers, absorption enhancers, surfactants, pH adjusters, preservatives, antioxidants, and the like. Examples of ingredients used in formulation include but are not limited to purified water, saline solution, phosphate buffer solution, dextrose, glycerol, ethanol and other pharmaceutically acceptable organic solvents, animal and vegetable oils, lactose, mannitol, glucose, sorbitol, crystal cellulose, hydroxypropyl cellulose, starch, corn starch, silicic acid, aluminum silicate magnesium, collagen, polyvinyl alcohol, poliovinylpyrrolidone, carboxyvinyl polymer, sodium carboxymethyl cellulose, sodium polyacrylate, sodium alginate, water-soluble dextran, sodium carboxymethyl starch, pectin methylcellulose, ethylcellulose, xanthan gum, gum arabic, tragacanth, casein, agar, polyethylene glycol, diglycerin, glycerin, propylene glycol, vaseline, paraffin, octyldodecyl myristate, isopropyl myristate, higher alcohols, stearyl alcohol, stearic acid, human serum albumin, and the like. If peptides are not readily absorbed by the transmucosal membrane, absorption enhancers that improve the absorption of poorly absorbed drugs include surfactants such as polyoxyethylene lauryl ethers, sodium lauryl sulfate, and saponin; bile salts such as glycocholic acid, deoxycholic acid, and taurocholic acid; chelating agents such as EDTA and salicylic acid; and caproic acid. Chelating agents; fatty acids such as caproic acid, capric acid, lauric acid, oleic acid, linoleic acid, mixed micelles, etc.; enamine derivatives, N-acyl collagen peptides, N-acylamino acids, cyclodextrins, chitosans, nitric oxide donors, and the like may also be used.

Round or tablet formulations can also be coated with sugar-coated, gastric- or enteric-soluble substances. Injectable formulations can contain distilled water for injection, saline, propylene glycol, polyethylene glycol, vegetable oils, alcohols, etc. In addition, wetting agents, emulsifying agents, dispersing agents, stabilizing agents, dissolving agents, dissolution aids, and preservatives can be added. If necessary, additives such as ordinary preservatives, antioxidants, coloring agents, sweetening agents, adsorbents, wetting agents, etc. can also be used in appropriate amounts.

The pharmaceutical compositions of the embodiments are useful for the prevention and/or treatment of central nervous system diseases involving VIPR2 activation, but are not limited to such as, mental disorders (schizophrenia, schizoaffective disorder, schizophreniform, delusional disorder, etc.), pediatric mental disorders (attention deficit disorder, attention-deficit/hyperactivity disorder, conduct disorder, autism, etc.), neurodegenerative disorders, neural stem cell disorders, neural precursor disorders, ischemic disorders, neurotraumatic disorders, affective disorders, psychomotor disorders, sleep disorders (hypersomnia, circadian rhythm sleep disorders, insomnia, abnormal sleep behavior, sleep deprivation, etc.) mental disorders such as anxiety (acute stress disorder, generalized anxiety disorder, social anxiety disorder, panic disorder, posttraumatic stress disorder, square fear, obsessive-compulsive disorder, etc.), false psychiatric disorders (acute hallucinatory mania, etc.), impulse control disorders (compulsive gambling, intermittent explosive disorder, etc.), mood disorders (bipolar I type I disorder, bipolar II disorder, mania, mixed affective states, etc.), major depression, chronic depression, seasonal depression, psychotic depression, seasonal depression, cognitive disorders (amnesia, geriatric dementia, HIV-related dementia, Alzheimer's disease, Alzheimer's disease, etc.) HIV-related dementia, Alzheimer's disease, Huntington's disease, dementia with Lewy bodies, vascular dementia, drug-related dementia, late onset dyskinesia, clonic muscle spasms, dystonia, delirium, Pick's disease, Creutzfeldt-Jakob disease, HIV disease, Gilles de la Tourette syndrome, epilepsy, muscle spasticity, mild cognitive impairment, etc.), mental lability (spasticity, Down syndrome, fragile X syndrome, etc.); premenstrual syndrome (PMS), premenstrual dysphoric mood disorder (PDD), postpartum depression, neuronal damage disorders (eye damage, retinopathy or macular degeneration of the eye, tinnitus, hearing Parkinson's disease, Parkinson's-like disorder, migraine, epilepsy, Alzheimer's disease, brain injury, stroke, cerebrovascular disease (cerebral atherosclerosis, cerebral amyloid angiopathy, hereditary cerebral hemorrhage, cerebral hypoxia-ischemia, etc.), drug addiction (drug addiction, alcoholism, amphetamine dependence, cocaine addiction, nicotine dependence, drug withdrawal syndrome, etc.), and eating disorders (anorexia, bulimia, distracted eating disorder, polyphagia, obesity, compulsive eating disorder, ice eating disorder, etc.). Additional diseases include, but are not limited to, inhibition of the growth of VIPR2-expressing cancers and use in the activation of immunity through inhibition of VIPR2 function, and the like.

The pharmaceutical compositions may be used in combination with other drugs and therapies such as various types of chemotherapy, surgical treatment, and radiation therapy useful for the above diseases.

When the pharmaceutical composition of the embodiments is administered to mammals (e.g., humans, mice, rats, guinea pigs, rabbits, dogs, horses, monkeys, pigs, etc.), especially humans, the dosage varies depending on the symptoms, patient age, sex, weight, susceptibility difference, administration method, administration interval, type of active ingredient, and type of formulation, and is not particularly limited. For example, 30 μg to 1000 mg, 100 μg to 500 mg, or 100 μg to 100 mg can be administered once or divided into several doses.

The following examples are merely illustrative and are intended only to explain the invention in detail together with the above-described embodiments and are not intended to limit the invention. Those skilled in the art may modify the invention in various ways without departing from the significance of the invention, and such modifications are also included in the scope of the invention.

EXAMPLES

Abbreviations used herein have the following meanings

VIPR2: Vasoactive intestinal peptide receptor 2
VIP: Vasoactive intestinal peptide
BSA: Bovine serum albumin
RP-HPLC: Reverse-phase high performance liquid chromatography
HRP: Horseradish peroxidase
SA: Streptavidin
HBSS: Hank's balanced salt solution
ELISA: Enzyme-linked immunosorbent assay
Ac: Acetyl
Cys: L-Cysteine
hmC: L-homocysteine
Mpa: 3-mercaptopropanoic acid
Pro: L-Proline
Tyr: L-Tyrosine
Leu: L-Leucine
Ile: L-Isoleucine
Arg: L-Arginine
Asp: L-Aspartic acid
Glu: L-Glutamic acid
Dap: (S)-2,3-Diaminopropanonic acid
Dab: (S)-2,4-Diaminobutanoic acid
Tyr(Ome): O-methyl-L-Tyrosine
4aF: 4-amino-L-Phenylalanine
4AcF: 4-acetyl-L-Phenylalanine
4amdF: 4-amide-L-Phenylalanine
3hF: 3-hydroxy-L-Phenylalanine
3(Ome)F: 3-methoxy-L-Phenylalanine
4amF: 4-aminomethyl-L-Phenylalanine
4fF: 4-fluoro-L-Phenylalanine
Gly: Glycine
Ala: L-Alanine
Aze: L-Azetidine carboxylic acid
thioP: L-Thioproline
Dhp: 3,4-dehydro-L-Proline
Pip: L-Pipecolic acid
Val: L-Valine
Nle: L-Norleucine
Ahep: (S)-2-Aminoheptanonic acid
Aoc: (S)-2-Aminooctanonic acid
Anon: (S)-2-Aminononic acid
CprA: L-Cyclopropylalanine
CbuA: L-Cyclobutylalanine
βhmLeu: β-homo-L-Leucine
M6a: 6-Mercaptohexanoic acid
M8a: 8-Mercaptooctanoic acid
DIBut: 1,4-Diiodobutane
DIPen: 1,5-Diiodopentane
DIHex: 1,6-Diiodohexane
DBoXy: 1,2-Bis(bromomethyl)benzene
DBmXy: 1,3-Bis(bromomethyl)benzene
DBpXy: 1,4-Bis(bromomethyl)benzene
TBMB: 1,3,5-Tris(bromomethyl)benzene
Nme-X: N-methylated amino acid X
αMe-X: α-methylated amino acid X
$^{D}$X: D-amino acid X
c[XY], c(XY): Cyclization between amino acid X to amino acid Y

Peptide Synthesis

The chemical synthesis of all peptides used in this example was outsourced to Scrum Inc. (Tokyo, Japan) and was carried out using a standard solid-phase synthesis method using 9-fluorenylmethoxycarbonyl group (Fmoc group) as a protecting group for the α-amino group on an automated synthesizer SyroII (Biotage Japan Ltd). A side-chain-protected amino acid-resin located at the C-terminus was placed in the synthesis column and the apparatus was set up. To the next amino acids protected with Fmoc group was added 1-[bis(dimethylamino)methylene]-1H-1,2,3-triazolo[4,5-b]pyridinium 3-oxide hexafluorophosphate (HATU)/diisopropylethylamine (DIEA) to activate and placed in a column. After completion of the coupling reaction, the column was washed and the Fmoc group was deprotected using 20% piperidine. The peptide chain was extended by repeating this process, and after deprotection of the Fmoc group of the final amino acid, the peptide resin was removed from the device.

The cyclization of peptides was based on the methods described in Non-Patent Literature 8, Non-Patent Literature 9, Non-Patent Literature 10 and Non-Patent Literature 11. As an example, the cyclization of Seq-1, 6 and 9 is shown below. For Seq-1 and Seq-6, the side-chain protected linear peptide resins were swollen with dimethylformamide (DMF). The protective groups on the lysine side chain (Dde) and the protective group on the aspartic acid side chain (ODmab) were deprotected by reacting in 2% hydrazine solution for 5 to 10 minutes, and the coupling reagent Oxima Pure and diisopropylcarbodiimide (DIC) were added, and the reaction was carried out at 5° C. for 3 hours. After washing the resin, TFA was added to deprotect the protecting group of the thiol group and simultaneously cut the monocyclic peptide from the resin. The monocyclic peptides were purified by RP-HPLC using a SunFire C18 column (10×150 mm) (Waters) and lyophilized.

For Seq-1, the monocyclic peptide was dissolved in a mixture of Tris-HCl buffer (pH8.5) and acetonitrile, then DMSO was added, and the peptides were cyclized by disulfide bonds by stirring at room temperature for 36 hours. For Seq-6, the monocyclic peptides were dissolved in dimethyl sulfoxide (DMSO) and dissolved in DMF in 3 equivalents of 1,3-bisbromomethylbenzene, and 10 mM tris(2-carboxyethyl) phosphine (TCEP), and 0.1M $NaHCO_3$ and acetonitrile, and reacted overnight at room temperature. The peptide was cyclized by the thioether bond between the thiol group and the alkyl halide linker. Seq-1 and 6 were purified by RP-HPLC using a SunFire C18 column (10×150 mm) (Waters) and lyophilized. The molecular weights of the final peptides were determined by microflex (Bruker) and the target product was identified.

Figure 10:
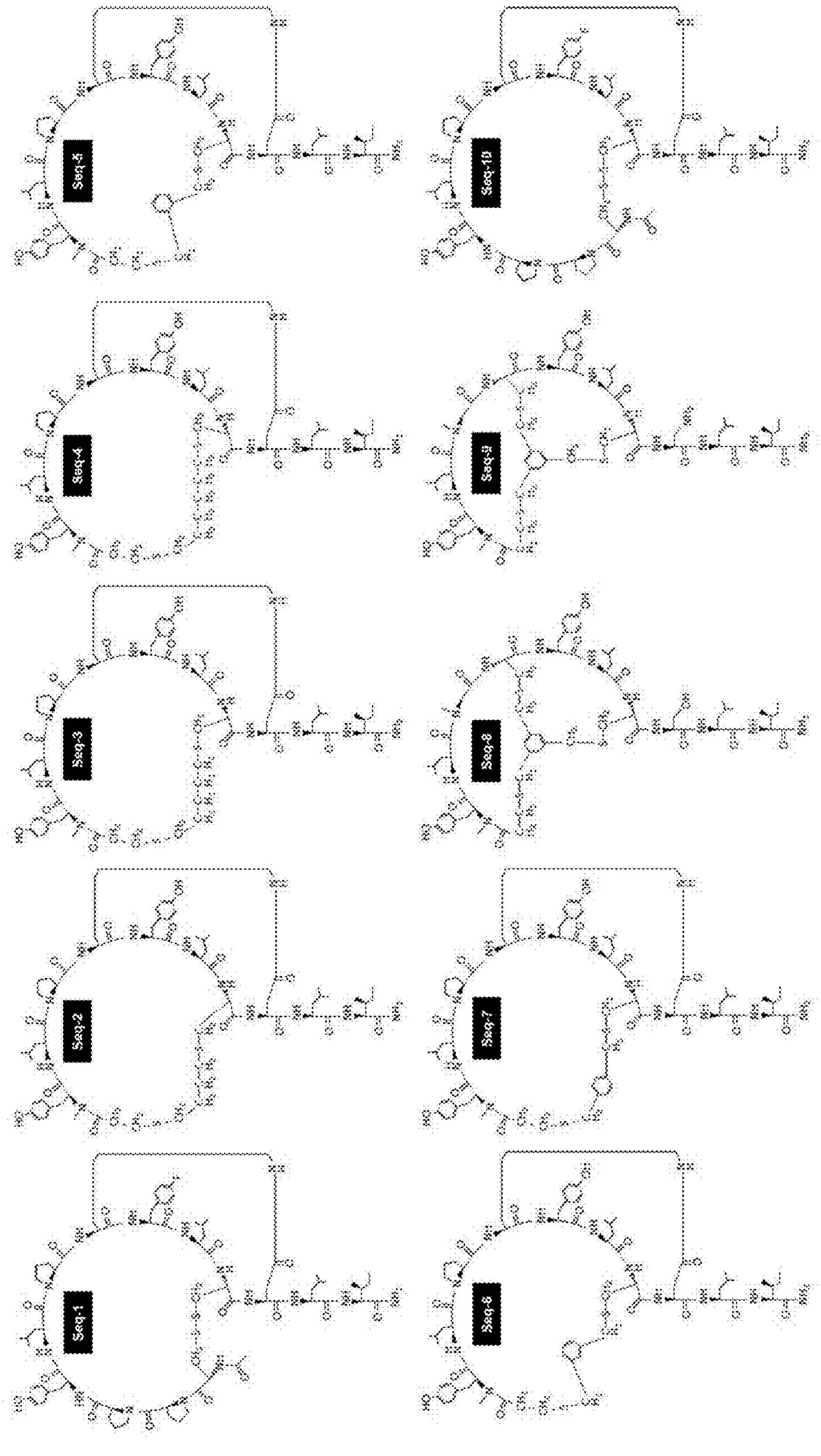
FIG. 10 shows the structural formulas of representative examples of the peptide embodiments used in the example.

For Seq-9, after washing the resin, TFA was added to deprotect the thiol protection group, and the linear peptide was cut out from the resin and then purified by RP-HPLC using a SunFire C18 column (10×150 mm) (Waters) and lyophilized. The linear peptide was dissolved in dimethyl sulfoxide (DMSO) and added with three equivalents of 1,3,5-tris(bromomethyl) benzene (TBMB) dissolved in DMF, 10 mM tris(2-carboxyethyl) phosphine (TCEP) containing 0.1M $NaHCO_3$, and acetonitrile, and reacted at 80° C. for 3 hours. The peptide was cyclized by the thioether bond between the thiol group and the alkyl halide linker. The bicyclic peptides were purified by RP-HPLC using a Sun- Fire C18 column (10×150 mm) (Waters) and lyophilized. The molecular weights of the final peptides were determined by microflex (Bruker) and the target product was identified. The theoretical molecular weight, the measured molecular weight, purity, cyclization type, and sequence of the peptides synthesized in this study are listed in Table 1. In addition, the amino acid sequences of Seq-1 through Seq-10 among them are shown below and their structural formulas are shown in FIG. 10. In Table 1 and the amino acid sequences below, amino acids without D-body notation indicate the L-body.

TABLE 1-1

| Name | Calcd MW | Obsvd MW | Voltage polarity | Purity (%) | Cycli-zation | Sequence |
|---|---|---|---|---|---|---|
| Biotin-Vlpep-3 | 2125.7 | 2125.456 | POS | 98.11 | S-S(1-10) | Biotin-c(Cys-Pro-Pro-Tyr-Leu-Pro-Arg-Arg-Leu-Cys)-Thr-Leu-Leu-Leu-Arg-Ser-OH |
| Vlpep-3 (SEQ ID No. 11) | 1941.4 | 1941.954 | POS | 97.52 | S-S(1-10) | Ac-c(Cys-Pro-Pro-Tyr-Leu-Pro-Arg-Arg-Leu-Cys)-Thr-Leu-Leu-Leu-Arg-Ser-OH |
| 3d-COOH | 1506.6 | 1506.582 | POS | 109 | S-S(1-10) | Ac-c(Cys-Pro-Pro-Tyr-Leu-Pro-Dap-Tyr-Leu-Cys)-Dap-Leu-Ile-OH |
| d-NH2 | 1505.8 | 1505.422 | POS | 100 | S-S(1-10) | Ac-c(Cys-Pro-Pro-Tyr-Leu-Pro-Dap-Tyr-Leu-Cys)-Dap-Leu-Ile-$NH_2$ |
| 3d-7-$^{D}$Dap | 1505.8 | 1505.361 | POS | 100 | S-S(1-10) | Ac-c(Cys-Pro-Pro-Tyr-Leu-Pro-Dap-Tyr-Leu-Cys)-Dap-Leu-Ile-$NH_2$ |
| 3d-11-$^{D}$Dap | 1505.8 | 1505.361 | POS | 100 | S-S(1 10) | Ac-c(Cys-Pro-Pro-Tyr-Leu-Pro-Dap-Tyr-Leu-Cys)-$^{D}$Dap-Leu-Ile-$NH_2$ |
| 3d-7/11-$^{D}$Dap/$^{D}$Dap | 1505.8 | 1505.254 | NEG | 100 | S-S(1-10) | Ac-c(Cys-Pro-Pro-Tyr-Leu-Pro-$^{D}$Dap-Tyr-Leu-Cys)-$^{D}$Dap-Leu-Ile-$NH_2$ |
| 3-11-Dab | 1519.9 | 1519.738 | POS | 100 | S-S(1-10) | Ac-c(Gys-Pro-Pro-Tyr-Leu-Pro-Dap-Tyr-Leu-Cys)-Dab-Leu-Ile-$NH_2$ |
| 3d-7/11-$^{D}$Dap/Dab | 1519.9 | 1519.847 | POS | 100 | S-S(1-10) | Ac-c(Cys-Pro-Pro-Tyr-Leu-Pro-$^{D}$Dap-Tyr-Leu-Cys)-Dab-Leu-Ile-$NH_2$, |
| 3d-11-$^{D}$Dap | 1519.9 | 1519.056 | NEG | 100 | S-S(1-10) | Ac-c(Cys-Pro-Pro-Tyr-Leu-Pro-Dap-Tyr-Leu-Cys)-$^{D}$Dab-Leu-Ile-$NH_2$ |
| 3d-7/11-$^{D}$Dap/Dap | 1519,9 | 1519.591 | NEG | 98.28 | S-S(1-10) | Ac c(Cys-Pro-Pro-Tyr-Leu Pro-Dap Tyr-Leu Cys)-$^{D}$Dab Leu-Ile-$NH_2$ |
| 3d-7-Dab | 1519.9 | 1513.376 | NEG | 100 | S-S(1-10) | Ac-c(Cys-Pro-Pro-Tyr-Leu-Pro-Dab-Tyr-Leu-Cys)-Dap-Leu-Ile-$NH_2$ |
| 3d-7/11-Dab/$^{D}$Dap | 1519,9 | 1519.841 | NEG | 100 | S-S(1-10) | Ac-c(Cys-Pro-Pro-Tyr-Leu-Pro-Dab-Tyr-Leu-Cys)-$^{D}$Dap-Leu-Ile-$NH_2$ |
| 3d-7-$^{D}$Dab | 1519.9 | 1519,907 | POS | 100 | S-S(1-10) | Ac-c(Cys-Pro-Pro-Tyr-Leu-Pro-$^{D}$Dab-Tyr-Leu-Cys)-Dap-Leu-Ile-$NH_2$ |
| 3d-7/11-$^{D}$Dap/$^{D}$Dap | 1519.9 | 1519.802 | POS | 100 | S-S(1-10) | Ac-c(Cys-Pro-Pro-Tyr-Leu-Pro-$^{D}$Dab-Tyr-Leu-Cys)-$^{D}$Dap-Leu-Ile-$NH_2$ |
| 3d-7/11-Dab/Dab | 1533.9 | 1533.096 | NEG | 100 | S-S(1-10) | Ac-c(Cys-Pro-Pro-Tyr-Leu-Pro-Dab-Tyr-Leu-Cys)-Dab-Leu-Ile-$NH_2$ |
| 3d-7/11-Dab/$^{D}$Dap | 1533.9 | 1533.087 | NEG | 100 | S-S(1-10) | Ac-c(Cys-Pro-Pro-Tyr-Leu-Pro-Dab-Tyr-Leu-Cys)-$^{D}$Dab-Leu-Ile-$NH_2$ |
| 3d-7/11-$^{D}$Dap/Dab | 1533.9 | 1533.611 | POS | 100 | S-S(MO) | Ac-C(Cys-Pro-Pro-Tyr-Leu-Pro-$^{D}$Dab-Tyr-Leu-Cys)-Dab-Leu-Ile-$NH_2$ |
| 3d-7/11-$^{D}$Dap/Dap | 1533.9 | 1533.817 | POS | 95.86 | S-S(1-10) | Ao-c(Cys-Pro-Pro-Tyr-Leu-Pro-$^{D}$Dab-Tyr-Leu-Cys)-Dab-Leu-Ile-$NH_2$ |
| 3d-7/11-Lys/Asp | 1576.9 | 1576.047 | POS | 100 | S-S(1-10) | Ac-c(Cys-Pro-Pro-Tyr-Leu-Pro-Lys-Tyr-Leu-Cys)Asp-Leu-Ile-$NH_2$ |
| 3d-4-NmeTyr | 1519.9 | 1519.586 | POS | 100 | S-S(I-IO) | Ac-c(Cys-Pro-Pro-NmeTyr-Leu-Pro-Dap-Tyr-Leu-Cys)-Dap-Leu-Ile-$NH_2$ |
| 3d-4-Tyr(Ome) | 1519.9 | 1519.748 | POS | 100 | S-S(1-10) | Ac-c(Cys-Pro-Pro-Tyr(OMe)-Leu-Pro-Dap-Tyr-Leu-Cys)-Dap-Leu-Ile-$NH_2$ |
| 3d-4-4aF | 1504.9 | 1504.568 | NEG | 100 | S-S(1-W) | Ac-c(Cys-Pro-Pro-4aF-Leu-Pro-Dap-Tyr-Leu-Cys)-Dap-Leu-Ile-$NH_2$ |
| 3d-4-4AcF | 1531.9 | 1531.271 | POS | 100 | s-sn-w) | Ac-c(cys-Pro-Pro-4AcF-Leu-Pro-Dap-Tyr-Leu-Cys)-Dap-Leu-Ile-$NH_2$ |

TABLE 1-1-continued

| Name | Calcd MW | Obsvd MW | Voltage polarity | Purity (%) | Cycli-zation | Sequence |
|---|---|---|---|---|---|---|
| 3d-4-4amideF | 1532.9 | 1532.892 | POS | 99.07 | S-S(1-10) | Ac-c(Cys-Pro-Pro-4amideF-Leu-Pro-Dap-Tyr-Leu-Cys)-Dap-Let-Ile-$NH_2$ |
| 3-4-3hF | 1505.8 | 1506.663 | POS | 100 | S-S(1-10) | Ac-c(Cys-Pro-Pro-3hF-Leu-Pro-Dap-Tyr-Leu-Cys)-Dap-Leu-Ile-$NH_2$ |
| 3d-4-3(Ome)F | 1519.9 | 1519.737 | POS | 100 | S-S(1-10) | Ac-e(Cys-Pro-Pro-3(Ome)F-Leu-Pro-Dap-Tyr-Leu-Cys)-Dap-Leu-Ile-$NH_2$ |
| 3d-4-4amF | 1513.9 | 1518.458 | NEG | 95.32 | S-Sd-10) | Ac-c(Cys-Pro-Pro-4amF-Leu-Pro-Dap-Tyr-Leu-Cys)-Dap-Leu-Ile-$NH_2$ |
| 3d-4-4fF | 1507.8 | 1507.071 | NEG | 98.74 | S-S(1-10) | Ac-c(Cys-Pro-Pro-4fF-Leu-Pro-Dap-Tyr-Leu-Cys)-Dap-Leu-Ile-$NH_2$ |
| 3d-4-aMeTyr | 1519.6 | 1520.386 | POS | 100 | S-Sd-W) | Ac-c(Cys-Pro-Pro-aMeTyr-Leu-Pro-Dap-Tyr-Leu-Cys)-Dap-Leu-Ile-$NH_2$ |
| 3d-5-NmeLeu | 1519.9 | 1519.611 | POS | 97.04 | S-S(1-10) | Ac-c(Cys-Pro-Pro-Tyr-NmeLeu-Pro-Dap-Tyr-Leu-Cys)-Dap-Leu-Ile-$NH_2$ |
| 3d-5-aMeLeu | 1519.9 | 1520.669 | POS | 100 | S-S(MO) | Ac c(Cys-Pro-Pro-TyraMeLeu-Pro-Dap-Tyr-Leu-Cys)-Dap-Leu-Ile-$NH_2$ |
| 3d-6-Aze | 1491.8 | 1491.034 | POS | 100 | S-S(1-10) | Ac-c(Cys-Pro-Pro-Tyr-Leu-Aze-Dap-Tyr-Leu-Cys)-Dap-Leu-Ile-$NH_2$ |
| 3d-6-Pip | 1519.9 | 1519.756 | POS | 100 | S-S(1-10) | Ac-c(Cys-Pro-Pro-Tyr-Leu-Pip-Dap-Tyr-Leu-Cys)-Dap-Leu-Ile-$NH_2$ |
| 3d-6-NmeAla | 1493.8 | 1493.784 | POS | 100 | S-S(1-11) | Ac-C(Cys-Pro-Pro-Tyr-Leu-NmeAla-Dap-Tyr-Leu-Cys)-Dap-Leu-Ile-$NH_2$ |

TABLE 1-2

| Name | Calcd MW | Obsvd MW | Voltage polarity | Purity (%) | Cycli-zation | Sequence |
|---|---|---|---|---|---|---|
| 3d-6-Nme$^D$Ala | 1493.8 | 1493.628 | POS | 190 | S-S(1-11) | Ac-c(Cys-Pro-Pro-Tyr-Leu-Nme$^D$Ala-Dap-Tyr-Leu-Cys)-Dap-Leu-Ile-$NH_2$ |
| 3d-6-NmeGly | 1479.8 | 1479.987 | PCS | 190 | S-S(1-10) | Ac-c(Cys-Pro-Pro-Tyr-Leu-NmeGly-Dap-Tyr-Leu-Cys)-Dap-Len-Ile-$NH_2$ |
| 3d-8-Tyr(OMe) | 1519.9 | 1519.827 | POS | 190 | S-S(1-10) | Ac-c(Cys-Pro-Pro-Tyr-Leu-Pro-Dap-Tyr(OMe)-Leu-Cys)-Dap-Leu-Ile-$NH_2$ |
| 3d-8-4af | 1504.9 | 1504 578 | POS | 100 | S-S(1-10) | Ac-c(Cys-Pro-Pro-Tyr-Leu-Pro-Dap-4aF-Leu-Cys)-Dap-Leu-Ile-$NH_2$ |
| 3d-8-4AcF | 1531.9 | 1531.715 | POS | 97.44 | S-S(1-10) | Ac-c(Cys-Pro-Pro-Tyr-Leu-Pro-Dap-4AcF-Leu-Cys)-Dap-Leu-Ile-$NH_2$ |
| 3d-8-4amideF | 1532.9 | 1532.592 | POS | 99.22 | S-S(1-10) | Ac-c(Cys-Pro-Pro-Tyr-Leu-Pro-Dap-4amideF-Leu-Cys)-Dap-Leu-Ile-$NH_2$ |
| 3d-8-3hf | 1505.8 | 1505.396 | PCS | 100 | S-S(1-10) | Ac-c(Cys-Pro-Pro-Tyr-Leu-Pro-Dap-3hF-Leu-Cys)-Dap-Leu-Ile-$NH_2$ |
| 3d-8-3(Ome)F | 1519.9 | 1519.651 | POS | 190 | S-S(1-10) | Ac-c(Cys-Pro-Pro-Tyr-Leu-Pro-Dap-3(Ome)F-Leu-Cys)-Dap-Leu-Ile-$NH_2$ |
| 3d-8-4amF | 1518.9 | 1518.436 | POS | 100 | S-S(1-10) | Ac-c(Cys-Pro-Pro-Tyr-Leu-Pro-Dap-4amF-Leu-Cys)-Dap-Leu-Ile-$NH_2$ |
| 3-8-4fF | 1507.8 | 1507.222 | POS | 100 | S-S(1-10) | Ac-c(Cys-Pro-Pro-Tyr-Leu-Pro-Dap-4fF-Lsu-Cys)-Dap-Leu-Ile-$NH_2$ |
| 3d-8-aMeTyr | 1519.8 | 1520.992 | POS | 190 | S-S(1-10) | Ac-c(Cys-Pro-Pro-Tyr-Leu-Pro-Dap-aMeTyr-Leu-Cys)-Dap-Leu-Ile-$NH_2$ |
| 3d-9-aMeLeu | 1519.9 | 1520.624 | POS | 100 | S-S(1-10) | Ac-c(Cys-Pro-Pro-Tyr-Leu-Pro-Dap-Tyr-aMeLeu-Cys)-Dap-Leu-Ile-$NH_2$ |
| 3d-12-Nle | 1505.8 | 1505.361 | POS | 99.91 | S-S(1-10) | Ac-c(Cys-Pro-Pro-Tyr-Leu-Pro-Dap-Tyr-Leu-Cys)-Dap-Nle-Ile-$NH_2$ |
| Sd-12-Ahep | 1519.9 | 1619.178 | NEG | 100 | S-S(1-10) | Ac-c(Cys-Pro-Pro-Tyr-Leu-Pro Dap-Tyr-Leu Cys)-Dap-Ahep-Ile-$NH_2$ |
| 30-12-Aoc | 1533.9 | 1533.526 | POS | 100 | S-S(1-10) | Ac-c(Cys-Pro-Pro-Tyr-Leu-Pro-Dap-Tyr-Leu-Cys)-Dap-Aoc-Ile-$NH_2$ |
| 3d-12-Anon | 1547.9 | 1547.484 | POS | 98.54 | S-S(1-10) | Ac-C(Cys-Pro-Pro-Tyr-Leu-Pro-Dap-Tyr-Leu-Cys)-Dap-Anon-Ile-$NH_2$ |
| 3d-12-CpA | 1503.8 | 1503.131 | NEG | 100 | S-S(1-10) | Ac-c(Cys-Pro-Pro-Tyr-Leu-Pro-Dap-Tyr-Leu-Cys)-Dap-CprA-Ile-$NH_2$ |
| 3d-12-CbuA | 1517.9 | 1518.632 | POS | 99.79 | S-S(1-10) | Ac-c(Cys-Pro-Pro-Tyr-leu-Pro-Dap-Tyr-Leu-Cys)-Dap-CbuA-Ile-$NH_2$ |
| 3d-12-aMeLeu | 1519.9 | 1519.697 | POS | 98.8 | S-S(1-10) | Ac-C(Cys-Pro-Pro-Tyr-Leu-Pro-Dap-Tyr-Leu-Cys)-Dap-aMeLeu-Ile-$NH_2$ |
| 3d-13-Leu | 1505.8 | 1505.379 | POS | 100 | S-S(1-10) | Ac-c(Cys-Pro-Pro-Tyr-Leu-Pro-Dap-Tyr-Leu-Cys)-Dap-Leu-Leu-$NH_2$ |
| Sd-13-aMeLeu | 1519.9 | 1520 279 | POS | 95.46 | S-S(1-10) | Ac-C(Cys-Pro-Pro-Tyr-Leu-Pro-Dap-Tyr-Leu-Cys)-Dap-Leu-aMdeLeu-$NH_2$ |
| 3d-13-βhmLeu | 1519.9 | 1519.758 | POS | 100 | S-S(1-10) | Ac-c(Cys-Pro-Pro-Tyr-Leu-Pro-Dap-Tyr-Leu-Cys)-Dap-Leu-βhmLeu-$NH_2$ |
| 3d-M6a/Cys | 1296.4 | 1296.696 | POS | 190 | S-S(1-8) | c(M6a-Tyr-Leu-Pro-Dap-Tyr-Leu-Cys)-Dap-Leu-Ile-$NH_2$ |
| 3d-M6a/hmC | 1310.4 | 1310.348 | POS | 97.95 | S-S(1-8) | c(M6a-Tyr-Leu-Pro-Dap-Tyr-Leu-hmC)-Dap-Leu-Ile-$NH_2$ |

TABLE 1-2-continued

| Name | Calcd MW | Obsvd MW | Voltage polarity | Purity (%) | Cycli-zation | Sequence |
|---|---|---|---|---|---|---|
| 3d-M8a/Cys | 1324.4 | 1324.458 | POS | 100 | S-5(1-8) | c(M8a-Tyr-Leu-Pro-Dap-Tyr-Leu-Cys)-Dap-Leu-Ile-$NH_2$ |
| 3d-M8a/hmC | 1338.4 | 1338 621 | POS | 100 | S-S(1-8) | c(M8a-Tyr-Leu-Pro-Dap-Tyr-Leu-hmC)-Dap-Leu-Ile-$NH_2$ |
| Seq-1 (SEQ ID No. 1) | 1508.8 | 1508.781 | NEG | 95.85 | S-S(1-10)/ amide(7-11) | c(Mpa-Pro-Pro-Tyr-Leu-Pro-c[Lys-Tyr-Leu-Cys)-Asp]-Leu-Ile-$NH_2$ |
| Seq-2 (SEQ ID No. 2) | 1377.7 | 1377 767 | POS | 100 | DlBut(1-8)/ amide(5-9) | c(Mpa-NmeTyr-Lsu-Pro-c[Lys-Tyr-Leu-Cys)-Asp]-Leu-Ile-$NH_2$ |
| Seq-3 (SEQ ID No. 3) | 1301.7 | 1391.884 | POS | 100 | DlPen(1-8)/ amide(5-9) | c(Mpa-NmeTyr-Leu-Pro-c[Lys-Tyr-Leu-Cys)-Asp]-Leu-Ile-$NH_2$ |
| Seq-4 (SEQ ID No. 4) | 1405.7 | 1405.871 | POS | 98.23 | DlHex(1-8)/ amide(5-9) | c(Mpa-NmeTyr-Leu-Pro-c[Lys-Tyr-Leu-Cys)-Asp]-Leu-Ile-$NH_2$ |
| Seq-5 (SEQ ID No. 5) | 1425.7 | 1425.499 | POS | 98.04 | DBoXy(1-8)/ amide(5-9) | c(Mpa-NmeTyt-Leu-Pro-c[Lys-Tyr-Leu-Cys)-Asp]-Leu-Ile-$NH_2$ |
| Seq-6 (SEQ ID No. 8) | 1425.7 | 1425.975 | POS | 100 | DBmXy(1-8)/ amide(5-9) | c(Mpa-NmeTyr-Leu-Pro-c[Lys-Tyr-Leu-Cys)-Asp]-Leu-Ile-$NH_2$ |
| Seq-7 (SEQ ID No. 7) | 1425.7 | 1425.712 | POS | 98.18 | DBpXy(1-8)/ amide(5-9) | c(Mpa-NmeTyr-Leu-Pro-c[Lys-Tyr-Leu-Cys)-Asp]-Leu-Ile-$NH_2$ |
| Seq-8 (SEQ ID NO. 8) | 1376.7 | 1376.482 | NEG | 96.87 | TBMB(1-5-8) | c(Mpa-NmeTyr-Leu-NmeGly-c(Cys)-Tyr-Leu-Cys)-Ser-Leu-Ile-$NH_2$ |
| Seq-9 (SEQ ID No. 9) | 1374.7 | 1374.703 | POS | 95.3 | TBMB(1-5-8) | c(Mpa-NmeTyr-Leu-NmeGly-c(Cys)-Tyr-Leu-Cys)-Dap-Leu-Ile-$NH_2$ |
| Seq-10 (SEQ ID No. 10) | 1558.8 | 1558.705 | NEG | 100 | S-S(1-10)/ amide(7-11) | Ac-c(Cys-Pro-Pro-Tyr-Leu-Pro-c[Lys-Tyr-Leu-Cys)-Asp]-Leu-Ile-$NH_2$ |

Seq-1:
(SEQ ID No. 1)
c(Mpa-Pro-Pro-Tyr-Leu-Pro-c[Lys-Tyr-Leu-Cys)-Asp]-Leu-Ile-$NH_2$

Seq-2:
(SEQ ID No. 2)
c(Mpa-NmeTyr-Leu-Pro-c[Lys-Tyr-Leu-Cys)-Asp]-Leu-Ile-$NH_2$

Seq-3:
(SEQ ID No. 3)
c(Mpa-NmeTyr-Leu-Pro-c[Lys-Tyr-Leu-Cys)-Asp]-Leu-Ile-$NH_2$

Seq-4:
(SEQ ID No. 4)
c(Mpa-NmeTyr-Leu-Pro-c[Lys-Tyr-Leu-Cys)-Asp]-Leu-Ile-$NH_2$

Seq-5:
(SEQ ID No. 5)
c(Mpa-NmeTyr-Leu-Pro-c[Lys-Tyr-Leu-Cys)-Asp]-Leu-Ile-$NH_2$

Seq-6:
(SEQ ID No. 6)
c(Mpa-NmeTyr-Leu-Pro-c[Lys-Tyr-Leu-Cys)-Asp]-Leu-Ile-$NH_2$

Seq-7:
(SEQ ID No. 7)
c(Mpa-NmeTyr-Leu-Pro-c[Lys-Tyr-Leu-Cys)-Asp]-Leu-Ile-$NH_2$

Seq-8:
(SEQ ID No. 8)
c(Mpa-NmeTyr-Leu-NmeGly-c(Cys)-Tyr-Leu-Cys)-Ser-Leu-Ile-$NH_2$

Seq-9:
(SEQ ID No. 9)
c(Mpa-NmeTyr-Leu-NmeGly-c(Cys)-Tyr-Leu-Cys)-Dap-Leu-Ile-$NH_2$

Seq-10:
(SEQ ID No. 10)
Ac-c[$Cys^1$-$Pro^2$-$Pro^3$-$Tyr^4$-$Leu^5$-$Pro^6$-c($Lys^7$-$Tyr^8$-$Leu^9$-$Cys^{10}$]-$Asp^{11}$)-$Leu^{12}$-$Ile^{13}$-$NH_2$

Seq-1 and Seq-10 are peptides produced by removing C-terminal three residues (Leu-Arg-Ser) from VIpep-3 and by forming the bicyclic ring of an S—S bond between position 1 and position 10 and an amide bond between position 7 and position 11. Seq-2 to Seq-7 are produced by removing N-terminal two residues (Cys-Pro) and C-terminal three residues (Leu-Arg-Ser) from VIpep-3, and forming the bicyclic ring of a thioether bond via a chemical linker between position 3 and position 10, and an amide bond between position 7 and position 11, and Seq-8 and Seq-9 are produced by removing N-terminal two residues (Cys-Pro) and C-terminal three residues (Leu-Arg-Ser) from VIpep-3, and forming the bicyclic ring of a thioether bond via a TBMB linker between positions 3, 7, and 10.

Construction of Competitive Binding Assay by Cell-Based ELISA

Figure 3:
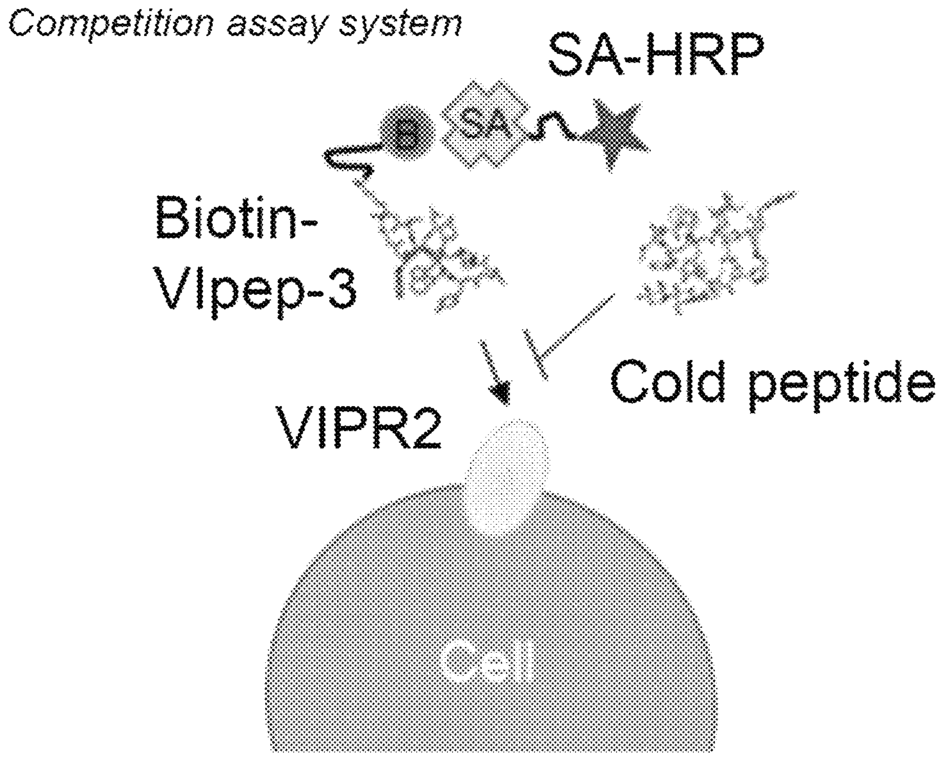
FIG. 3 shows an overview of the competitive binding assay by cell-based ELISA used to confirm the binding activity of peptides with substituted amino acid residues to VIPR2. In the figure, SA indicates streptavidin, B indicates biotin, and HRP indicates horseradish peroxidase.

To confirm the binding activity of the amino acid substituted peptides to VIPR2, a competitive binding assay was constructed using the cell-based ELISA method shown in FIG. 3. The following is a brief description of this cell-based ELISA method. Human VIPR2-expressing cell line (Catalog No. HTS079RTA, manufactured by EUROFINS) was spread in a 96-well plate using the culture medium provided by the manufacturer, and cultured overnight at 37° C. in a $CO_2$ incubator. After washing the plates with HBSS containing 0.1% BSA, the mixtures containing Biotin-VIpep-3 (1000 nM) and any concentration of amino acid substituted peptide or VIpep-3 were prepared and added at 50 μL/well. After reaction on ice for 60 minutes, the plate was washed with 0.1% BSA containing HBSS. Biotin-VIpep-3 bound to VIPR2-expressing cells adhering to the plate was detected with SA-HRP (catalog no. ab7403, Abcam). For HRP quantification, SuperSignal ELISA Pico Chemiluminescent Substrate (Catalog No. 37070, ThermoFisher) was used to measure chemiluminescence values. The binding of Biotin-VIpep-3 to the cell-surface VIPR2 competes with the binding of the amino acid substituted peptides and VIpep-3 coexisting in the solution to VIPR2, and therefore, is inhibited in a concentration-dependent manner of the amino acid substituted peptides and VIpep-3. In other words, the binding activity of amino acid substituted peptides and VIpep-3 to VIPR2 is detected as a competitive inhibitory activity against Biotin-VIpep-3 binding. Assuming the luminescence value of the well without VIpep-3 indicates 100% inhibitory activity, and the luminescence value of the well without the amino acid substituted peptide or VIpep-3 indicates 0% inhibitory activity, 50% inhibitory activity values of amino acid substituted peptides and VIpep-3 were calculated. Then, using the 50% inhibitory activity value of VIpep-3 as 1, the relative inhibitory activity values of the amino acid-substituted peptides were calculated.

Evaluation of the Binding Activity of Amino Acid Substituted Peptides to VIPR2

Figure 4:
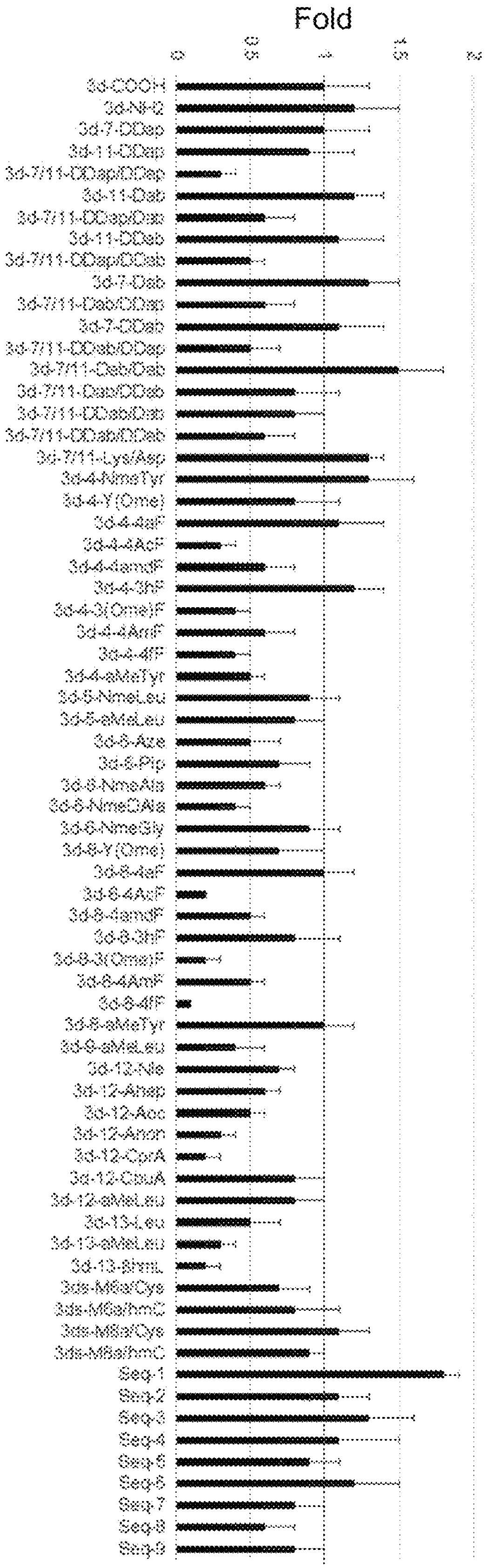
FIG. 4 shows a group of peptide sequences subjected to the amino acid residue substitution study, and binding activities of such representative examples of the inventive peptides to VIPR2 are shown in comparison with that of the parent peptide VIpep-3.

FIG. 4 shows the results of the competitive binding assay against VIPR2-expressing cells with N=4. Representative examples of the inventive peptides (Seq-1 through Seq-9) were all competitive against Biotin-VIpep-3. These results indicate that the inventive peptides with amino acid substitutions and bicyclization have VIPR2 binding activity. In particular, the binding activities of Seq-1 to 4 and Seq-6 were equal to or higher than those of VIpep-3.

Evaluation of the Antagonist Activity of the Inventive Peptide Against VIPR2

One of the downstream signals of VIPR2 is known to be changes in intracellular calcium concentration. Human VIPR2-expressing cell line (Catalog No. HTS079RTA, manufactured by Eurofins) was treated with Scree Quest™ Fluo-8 No Wash Calcium Assay Kit (Catalog No. 36315, AAT Bioquest) to introduce Fluo-8, an indicator reagent to measure changes in intracellular calcium concentration by fluorescence. The natural ligand VIP (150 nM final concentration) and VIpep-3 (final concentration 750 nM) or representative examples of the peptides of the embodiments (Seq-1, Seq 5-9) (final concentration 750 nM) were co-added and changes in fluorescence intensity were observed over time using fluorescence microscopy. The difference between the fluorescence intensity before the addition of VIP and the strongest fluorescence intensity after the addition of VIP was taken as 100% and compared to the difference in fluorescence intensity when VIpep-3 or the inventive peptide was co-added.

Figure 5:
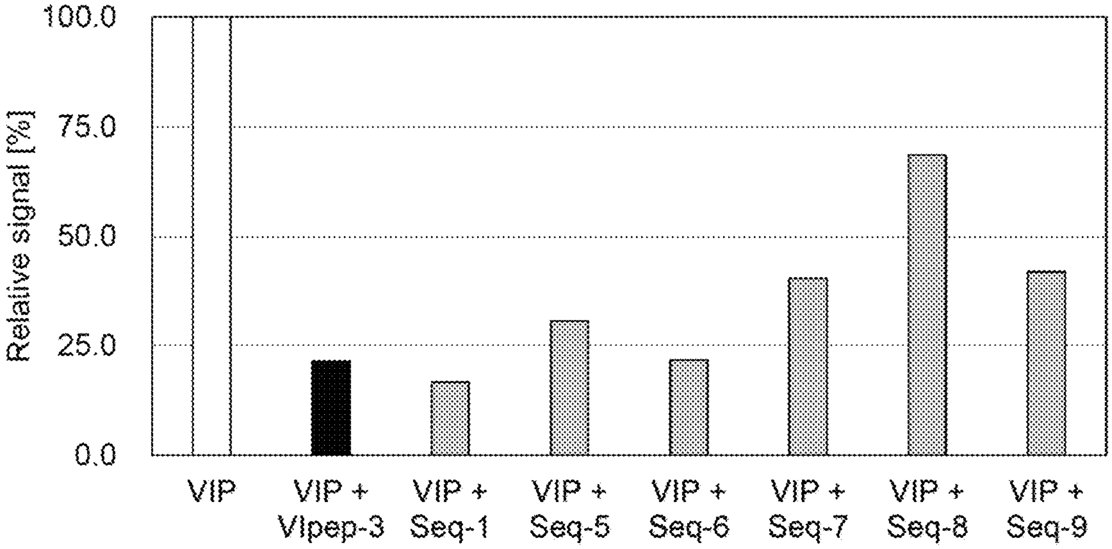
FIG. 5 shows the results of the evaluation of changes in intracellular calcium concentration, one of the downstream signals of VIPR2 in VIPR2-expressing cells added with representative examples of the present peptides and VIP.

As shown in FIG. 5, VIpep-3 and representative examples of the peptide embodiments (Seq-1, 5-9) were found to inhibit the receptor-activating activity of VIP on VIPR2. In particular, the inhibitory activities of Seq-1 and Seq-6 were similar to or greater than that of VIpep-3.

Evaluation of the Resistance of the Inventive Peptides to Protease Degradation

Figure 6:
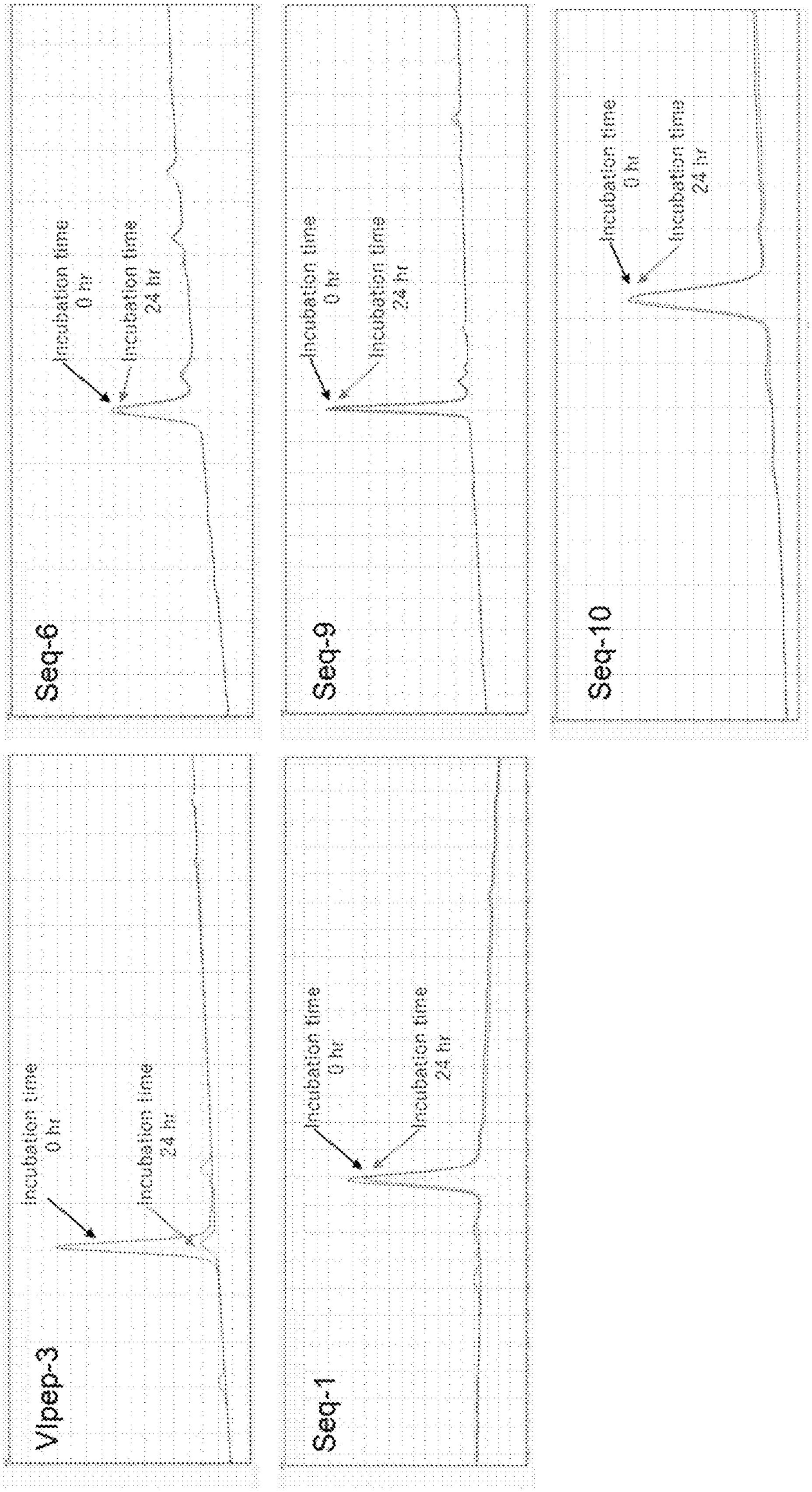
FIG. 6 shows the comparative results of the resistance to protease degradation of VIpep-3 and representative examples of the peptides of the embodiments, both of which were mixed with rat plasma.

To confirm that the peptides of the embodiments are resistant to protease degradation compared to VIpep-3, VIpep-3 or representative peptides of the embodiments (Seq-1, Seq-6, Seq-9, or Seq-10) were mixed in rat plasma, and after a certain incubation time, the residual amount of the peptide was evaluated by the presence or absence of peaks on RP-HPLC. To 1 μL of each 10 mM peptide, 20 μL of rat plasma was added, and incubated at 37° C. for an arbitrary time (0 or 24 hours). Then, for VIpep-3, 80% acetonitrile, for the other peptides, 200 μL each of acetonitrile was added, mixed well, placed on ice for 10 minutes, and centrifuged at 15,000 rpm at 4° C. for 10 minutes to remove plasma proteins. The supernatant was collected and transferred to a SunFire C18 column (5 μm, 4.6×150 mm) using RP-HPLC (liquid A: 0.1% TFA/water, liquid B: 0.1% TFA/acetonitrile, 80% solution A to 10% solution A at 1 mL/min. (20 min gradient) to detect the remaining amount of peptides. As shown in FIG. 6, the VIpep-3-derived peak was greatly reduced after 24 hours of incubation, suggesting that any parts in the sequence underwent protease degradation. On the other hand, the peaks derived from representative peptides of the embodiments (Seq-1, Seq-6, Seq-9, and Seq-10) remained almost the same after 24 hours of incubation compared to 0 hours of incubation. These results indicate that the peptides of the embodiments with amino acid substitutions and bicyclization are resistant to protease degradation.

Evaluation of the Selective Antagonist Activity of the Inventive Peptide Against VIPR2

A representative example of any concentration of the inventive peptide (Seq-10) was added to cells expressing VIPR1-expressing cells, VIPR2-expressing cells, or PAC1-expressing cells all of which have been transfected with intracellular calcium concentration indicator and incubated for 30 minutes. Then, VIPR1 cells and VIPR 2 cells were treated with VIP (25 nM and 150 nM, respectively), and PAC1 cells were treated with PACAP (35 nM). The change in intracellular calcium concentration for 2 minutes immediately after the addition thereof was measured by FLIPR Tetra. The inhibition rate of the antagonist peptides was calculated, assuming that the change in intracellular calcium concentration when only the ligand for VIP or PACAP was added was defined as 0% inhibition, and the change in intracellular calcium concentration when both the antagonist peptide and the ligand were not added was defined as 100%.

Figure 7:
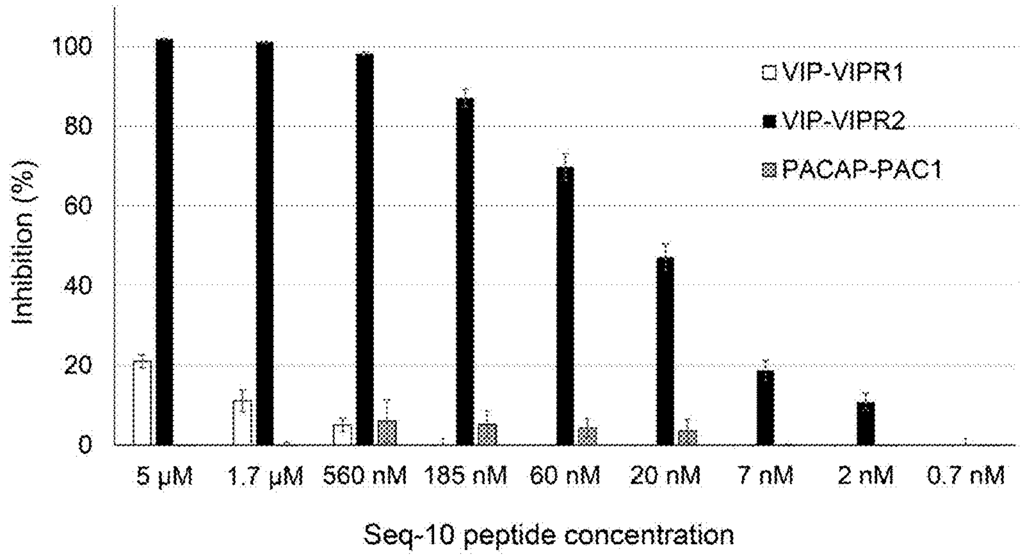
FIG. 7 shows the results of evaluation of changes of intracellular calcium concentration, one of the downstream signals of VIPR1 in VIPR1-expressing cells after addition of representative examples of the inventive peptides and VIP, the results of evaluation of changes of intracellular calcium concentration, one of the downstream signals of VIPR2 in VIPR2-expressing cells after addition of representative examples of the inventive peptides and VIP, and the results of evaluation of changes of intracellular calcium concentration, one of the downstream signals of PAC1 in PAC1-expressing cells after addition of representative examples of the inventive peptides and PACAP.

As shown in FIG. 7, the antagonist activity of the representative example of inventive peptide (Seq-10) was significantly strong against VIP-VIPR2 interaction than those against VIP-VIPR1 or PACAP-PAC1 interactions.

Evaluation VIPR2 Antagonist Activity of the Inventive Peptide In Vivo

Ro25-1553 (Peptide Institute, Inc.) which is an analog of VIP and a selective agonist for VIPR2, was dissolved in PBS (0.4 nmol/g body weight), and then mixed at 9:1 with the representative example of the inventive peptide (Seq-10) dissolved in DMSO (1 nmol/g body weight or 10 nmol/g body weight) or DMSO (vehicle group) (at a final concentration of DMSO is 10%). These solutions were administered subcutaneously to ICR mice (12 days old, male). 1 hour later, brains were removed, prefrontal cortex was dissected, and the phosphorylation of intracellular cyclic AMP response sequence-binding protein (CREB) (one of the downstream signals of VIPR2) in the cells was evaluated by Western blotting. The antibodies used for Western blotting were anti-phosphorylated CREB antibody (#9198) and anti-CREB antibody (#9197) purchased from Cell Signaling Technology.

Figure 8:
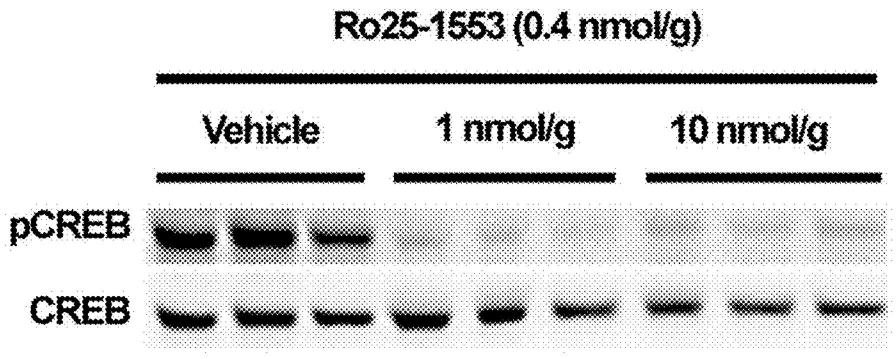
FIG. 8 shows the evaluated results of phosphorylation of cAMP response element binding protein (CREB) (one of the downstream signals of VIPR2) in cells of the prefrontal cortex of the brain, after subcutaneous administration to ICR mice (12 days old) of an analog of VIP, Ro25-1553, which is a selective agonist for VIPR2, (indicated in the figure as Vehicle), or a mixture of representative example of the peptide embodiments and Ro25-1553 (indicated in the figure as peptide concentration 1 nmol/g or 10 nmol/g).

As shown in FIG. 8, phosphorylation of CREB was clearly inhibited in the presence of Seq-10, indicating that the representative example of the present peptide has an antagonist activity against VIPR2 in vivo.

Figure 9:
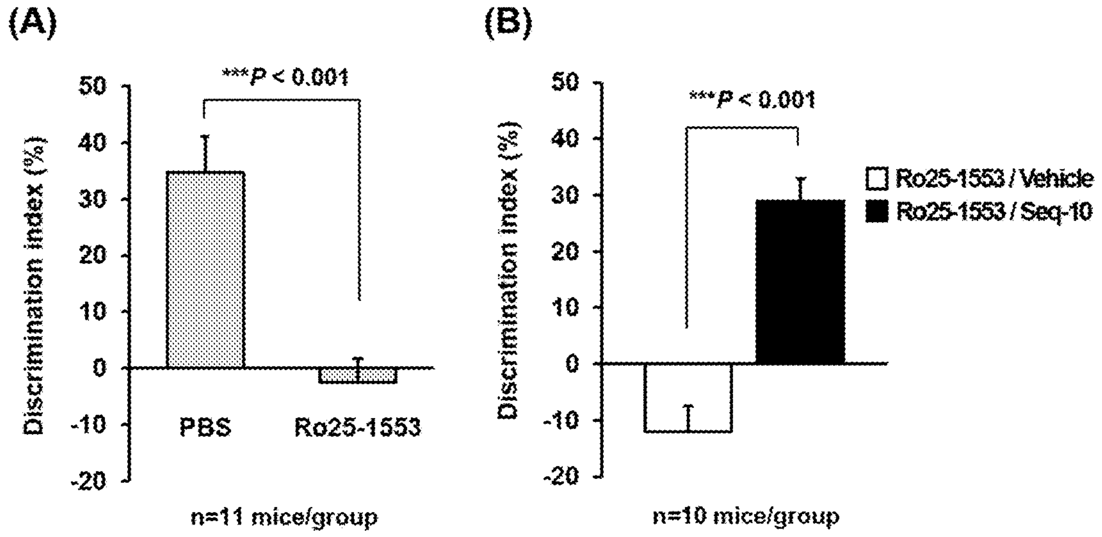
FIG. 9A shows the results of the evaluation of recognition function to novel objects in mice treated with an analog of VIP, Ro25-1553, which is a selective agonist of VIPR2.
FIG. 9B shows the results of the evaluation of recognition function to novel objects in mice treated with Ro25-1553 alone or a mixture of Ro25-1553 and a representative example of the inventive peptide.

Evaluation of Improvement of Recognition Function to Novel Objects in Mice by Administration of the Inventive Peptide As reported in Non-Patent Literature 12, the recognition function to novel objects was clearly reduced in mice (8 weeks old) that were continuously bred and grown after the administration of Ro25-1553 subcutaneously on day 1 of birth for 14 days (FIG. 9A). We evaluated whether the peptide could improve the recognition function to novel objects, which is reduced by the activation of VIPR2. Ro25-1553 (Peptide Institute, Inc.) an analog of VIP and a selective agonist for VIPR2, was dissolved in PBS (0.07 nmol/g body weight), and then mixed at 99:1 with a representative example of the inventive peptide (Seq-10) dissolved in DMSO (1 nmol/g body weight) or DMSO (Vehicle group) (1% final concentration of DMSO). These solutions were administered subcutaneously once daily to male ICR mice on postnatal day 1 for 14 days, the mice were continuously bred and subjected to a novel object recognition test at 8 weeks of age. The novel object recognition test was conducted during the light period (8:00-20:00) according to Non-Patent Literature 12. First, test cages (30 cm×30 cm×35 cm) made of acrylic-modified polyvinyl chloride were placed in a soundproofed laboratory at an illumination level of 30 lux and covered only with wooden sterilized soft chips (Sankyo Lab Service Co.). Two different objects were placed at a distance of 8 cm from the wall (Objects a and b were randomly selected from a golf ball, a Lego block, a plastic cylinder and an electrical outlet) were placed at 8 cm from the wall and allowed to explore freely for 10 minutes (training trial). Twenty-four hours later, object b was replaced by a novel object c in the test cage and allowed to explore freely for 5 minutes (test trial). The animals' behavior during the training and test trials was video-recorded, and the search time for each of the two objects was measured. The discrimination index was calculated as the ratio (%) of the search time difference between object c and object a to the total search time in the test trial.

As shown in FIG. 9B, Ro25-1553-treated mice showed a clear decrease in recognition function to novel objects. On the other hand, mice treated with a mixture with the representative example of the present peptide (Seq-10) showed a significant improvement in recognition of novel objects (p-value by Student's t-test was less than 0.001). And their recognition function was almost the same as that of normal mice. This result indicates that administration of the peptide can significantly prevent and improve the impairment of recognition function to novel objects in mice due to activation of VIPR2.

INDUSTRIAL APPLICABILITY

The peptides of the embodiments are resistant to protease degradation, and peptide binding to VIPR2 results in inhibition of natural ligand-mediated VIPR2 signaling. Therefore, the peptide may be useful for the prevention and treatment of diseases involving VIPR2 activation, such as schizophrenia and autism spectrum disorders.

The peptides of the embodiments can not only be used as drugs themselves, but also as delivery molecules to VIPR2-expressing tissues and can also be used as a molecule to detect the expression of VIPR2.

Furthermore, the peptides are expected to be more effective in the prevention and treatment of schizophrenia and autism spectrum disorders when used in combination with drugs and therapies that have other mechanisms of action.

The invention claimed is:

1. A cyclic peptide comprising an amino acid sequence represented by formula (17):

$$c[X^1\text{-Pro-}X^3\text{-Tyr}^4\text{-Leu}^5\text{-Pro}^6\text{-}c(X^7\text{-}X^8\text{-Leu}^9\text{-Cys}^{10}]\text{-}X^{11})\text{-}X^{12}\text{-}X^{13} \quad (17)$$

wherein $X^1$ denotes cysteine, Mpa (3-mercaptopropionic acid), or D-cysteine;

$X^3$ denotes N-methylglycine, N-methylalanine, 2-azetidine-2-carboxylic acid, proline, hydroxyproline, 3,4-dehydroprolone, pipecolic acid, serine, or lysine;

$X^8$ denotes tyrosine, proline, or arginine;

$X^7$ and $X^{11}$ denotes any combination of lysine and aspartic acid, ornithine and glutamic acid, aspartic acid and lysine, glutamic acid and ornithine, lysine and glutamic acid, or glutamic acid and lysine;

$X^{12}$ and $X^{13}$, each independently denotes leucine, isoleucine, or norleucine;

$X^1$ and $Cys^{10}$ form a disulfide bond between their side chains, and $X^7$ and $X^{11}$ form an amide bond between their side chains, thereby forming two cyclic structures in a molecule of the peptide of formula (17); and an N-terminal amino group and a C-terminal carboxyl group may be modified;

or a pharmaceutically acceptable salt thereof.

2. The cyclic peptide according to claim 1, or a pharmaceutically acceptable salt thereof, wherein $X^1$ denotes cysteine;

$X^3$ denotes proline or serine;

$X^7$ denotes lysine;

$X^8$ denotes tyrosine;

$X^{11}$ denotes aspartic acid;

$X^{12}$ and $X^{13}$, each independently denotes leucine, isoleucine or norleucine; and an N-terminal amino group is acetylated, and a C-terminal carboxyl group is amidated.

3. The cyclic peptide according to claim 1, wherein the cyclic peptide is resistant to protease degradation.

4. The cyclic peptide according to claim 1, wherein the cyclic peptide is biotin-labeled, fluorescence-labeled, or luminescent-labeled.

5. A pharmaceutical, diagnostic, and/or research reagent comprising the cyclic peptide according to claim 1.

6. A prodrug comprising the cyclic peptide according to claim 1, wherein one or more amino groups in the cyclic peptide are acylated, alkylated or phosphorylated, or a pharmaceutically acceptable salt of the prodrug.

7. A cyclic peptide having an amino acid sequence represented by any one of SEQ ID NOs.1 to 10, or a pharmaceutically acceptable salt thereof.

* * * * *